US010053734B2

(12) United States Patent
Behrens et al.

(10) Patent No.: US 10,053,734 B2
(45) Date of Patent: Aug. 21, 2018

(54) METHODS FOR TREATING, DIAGNOSING, AND MONITORING LUPUS

(71) Applicant: Genentech, Inc., South San Francisco, CA (US)

(72) Inventors: Timothy W. Behrens, Burlingame, CA (US); Robert R. Graham, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/040,949

(22) Filed: Feb. 10, 2016

(65) Prior Publication Data

US 2016/0273044 A1   Sep. 22, 2016

Related U.S. Application Data

(63) Continuation of application No. 13/501,448, filed as application No. PCT/US2010/051589 on Oct. 6, 2010, now abandoned.

(60) Provisional application No. 61/278,510, filed on Oct. 7, 2009.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/118* (2013.01); *C12Q 2600/156* (2013.01)

(58) Field of Classification Search
CPC ............ C12Q 1/6883; C12Q 2600/106; C12Q 2600/156
See application file for complete search history.

(56) References Cited

U.S. PATENT DOCUMENTS

| | | | |
|---|---|---|---|
| 4,657,760 | A | 4/1987 | Kung et al. |
| 4,683,195 | A | 7/1987 | Mullis et al. |
| 4,683,203 | A | 7/1987 | Anton et al. |
| 4,816,567 | A | 3/1989 | Cabilly et al. |
| 5,206,344 | A | 4/1993 | Katre et al. |
| 5,225,212 | A | 7/1993 | Martin et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 6,027,889 | A | 2/2000 | Barany et al. |
| 6,900,016 | B1 | 5/2005 | Venter et al. |
| 7,205,106 | B1 | 4/2007 | Mirel et al. |
| 2003/0119004 | A1 | 6/2003 | Wenz et al. |
| 2003/0162180 | A1 | 8/2003 | Pricop |
| 2007/0031848 | A1 | 2/2007 | Cargill et al. |
| 2007/0269827 | A1 | 11/2007 | Harley |

FOREIGN PATENT DOCUMENTS

| | | |
|---|---|---|
| CA | 2 019 559 C | 12/1980 |
| EP | 0 332 435 B1 | 9/1989 |
| EP | 0 332 435 B2 | 9/1989 |
| EP | 0 404 097 B1 | 12/1990 |
| EP | 0 404 097 B2 | 12/1990 |
| JP | 2003-061677 A | 3/2003 |
| JP | 5937008 B2 | 6/2016 |
| RU | 2009/147281 A | 6/2011 |
| WO | WO-91/10741 A1 | 7/1991 |
| WO | WO-93/01161 A1 | 1/1993 |
| WO | WO-96/33735 A1 | 10/1996 |
| WO | WO-96/34096 A1 | 10/1996 |
| WO | WO-98/24893 A2 | 6/1998 |
| WO | WO-2001/011084 A1 | 2/2001 |
| WO | WO-01/92579 A2 | 12/2001 |
| WO | WO-01/92579 A3 | 12/2001 |
| WO | WO-2002/018414 A2 | 3/2002 |
| WO | WO-2002/018414 A3 | 3/2002 |
| WO | WO-2002/057414 A2 | 7/2002 |
| WO | WO-2002/057414 A3 | 7/2002 |
| WO | WO-2005/086872 A2 | 9/2005 |
| WO | WO-2005/086872 A3 | 9/2005 |
| WO | WO-2006/079463 A1 | 8/2006 |
| WO | WO-2007/019219 A2 | 2/2007 |
| WO | WO-2007/019219 A3 | 2/2007 |
| WO | WO-2007/109052 A2 | 9/2007 |
| WO | WO-2007/109052 A3 | 9/2007 |
| WO | WO-2008/033239 A2 | 3/2008 |
| WO | WO-2008/033239 A8 | 3/2008 |

(Continued)

OTHER PUBLICATIONS

Miretti et al. "A High-Resolution Linkage-Disequilibrium Map of the Human Major Histocompatibility Complex and First Generation of Tag Single-Nucleotide Polymorphisms," *Am. J. Hum. Genet.* 76:634-646, (2005, e-pub. Mar. 1, 2005).

Slegen et al. "Genome-Wide Association Scan in Women With Systemic Lupus Erythematosus Identifies Susceptibility Variants in *ITGAM, PXK, KIAA1542* and Other Loci," *Nature Genetics* 40(2):204-210, (Feb. 2008, e-pub. Jan. 20, 2008).

Abbas, A.R. et al. (Jun. 2005, e-pub. Mar. 24, 2005). Immune Response in Silico (IRIS) Immune-Specific Genes Identified From a Compendium of Microarray Expression Data. *Genes Immun.* 26(4):319-331.

Anonoymous. (Oct. 27, 2005). "A Haplotype Map of the Human Genome," *Nature* 437(7063):1299-1320.

(Continued)

*Primary Examiner* — Steven Pohnert
(74) *Attorney, Agent, or Firm* — Morrison & Foerster LLP

(57) ABSTRACT

Methods of identifying, diagnosing, and prognosing lupus, including certain subphenotypes of lupus, are provided, as well as methods of treating lupus, including certain subpopulations of patients. The methods provided are based on a set of alleles associated with systemic lupus erythematosus (SLE) risk loci including BLK, TNIP1, PRDM1, JAZF1, UHRF1BP1, IL10, IFIH1, CFB, CEC16A, IL12B and SH2B3 that contribute to SLE risk. Also provided are methods for identifying effective lupus therapeutic agents and predicting responsiveness to lupus therapeutic agents.

22 Claims, 12 Drawing Sheets

(56) References Cited

FOREIGN PATENT DOCUMENTS

| WO | WO-2008/087647 A2 | 7/2008 |
|---|---|---|
| WO | WO-2008/144761 A2 | 11/2008 |
| WO | WO-2008/144761 A3 | 11/2008 |
| WO | WO-2009/015087 A2 | 1/2009 |
| WO | WO-2009/065132 A1 | 5/2009 |
| WO | WO-2009/117122 A2 | 9/2009 |
| WO | WO-2010/03960 A2 | 4/2010 |
| WO | WO-2010/03960 A3 | 4/2010 |
| WO | WO-2010/03960 A8 | 4/2010 |
| WO | WO-2010/036960 A2 | 4/2010 |
| WO | WO-2011/044205 A1 | 4/2011 |

OTHER PUBLICATIONS

Arbuckle, M.R. et al (Oct. 16, 2003). "Development of Autoantibodies Before the Clinical Onset of Systemic Lupus Erythematosus," *N. Engl. J. Med.* 349(16):1526-1533.

Arita et al. "Recognition of hemi-methylated DNA by the SRA protein UHRF1 by a base-flipping mechanism," *Nature* 455:818-821. (Oct. 2008).

Baechler, E.C. et al. (Dec. 2004, e-pub. Oct. 1, 2004). "The Emerging Role of Interferon in Human Systemic Lupus Erythematosus," *Curr Opin Immunol* 16(6):801-807.

Baechler, E.C. et al. (Mar. 4, 2003). "Interferon-Inducible Gene Expression Signature in Peripheral Blood Cells of Patients with Severe Lupus," *Proc Nat. Acad. Sci. USA* 100(5):2610-2615.

Banchereau, J. et al. (Sep. 2006). "Type I Interferon in Systemic Lupus Erythematosus and Other Autoimmune Diseases," *Immunity* 25(3):383-92.

Barbas, C.F. et al. (Apr. 1994). "In Vitro Evolution of a Neutralizing Human Antibody to Human Immunodeficiency Virus Type 1 to Enhance Affinity and Broaden Strain Cross-Reactivity," Proc Nat. Acad. Sci. USA 91:3809-3813.

Barrett et al. "Haploview: Analysis and Visualization of LD and Haplotype Maps," *Bioinformatics* 21(2):263-265 (2005).

Barrett et al. "Genome-Wide Association Defines More Than 30 Distinct Susceptibility Loci for Crohn's Disease," Nature Genet 41(6):70-707 (Jun. 2009).

Bauer, J.W. et al. (Dec. 2006). "Elevated Serum Levels of Interferon-Regulated Chemokines are Biomarkers for Active Human Systemic Lupus Erythematosusm" *PLoS Medicine* 3(12)(:e491):2274-2284.

Bell, J. (May 27, 2004). "Predicting Disease Using Genomics," *Nature* 429(6990):453-456.

Benner et al "Evolution, Language and Analogy in Functional Genomics," *Trends in Genetics* 17(7):414-418 (Jul. 2001).

Bennett, L. et al. (Mar. 17, 2003). "Interferon and Graulopoiesis Signatures in Systemic Lupus Erythermatosus Blood," *J. Exp. Med.* 197(6):711-723.

Boerner, P. et al.,(Jul. 1, 1991). "Production of Antigen-Specific Human Monoclonal Antibodies from In Vitro-Primed Human Splenocytes," *J. Immunol.* 147(1):86-95.

Brodeur, B.R. et al.(1987). *Monoclonal Antibody Production Techniques and Applications*, L.B. Schook, ed., Marcel Dekker, Inc., New York, NY, pp. 55-93.

Brüggemann, M. et al. (1993). "Designer Mice: The Production of Human Antibody Repertoires in Transgenic Animals," *Year in Immunol.* 7:33-40.

Burton, P.R. et al. (Jun. 2007). "Genome-Wide Association Study of 14,000 Cases of Seven Common Diseases and 3,000 Shared Controls," 447(7145):661-678.

Buyon, J.P. et al. (1988). "Surface Expression of Gp 165/95, the Complement Receptor CR3, as a Marker of Disease Activity in Systemic *Lupus Erythematosus,*" *Clin Immunol Immunopathol* 46(1):141-149.

Cambridge, G. et al. (2008, e-pub. Oct. 25, 2007). "B Cell Depletion Therapy in Systemic Lupus Erythaematosus: Relationship Among Serum B Lymphocyte Stimulator Levels, Autoantibody Profile and clinical Response," *Ann Rheum Dis* 67:10011-1016.

Cariello, N.F. et al. (May 1988). "Resolution of a Missense Mutant in Human Genomic DNA by Denaturing Gradient Gel Electrophoresis and Direct Sequencing Using in Vitro DNA Amplification: HPRT$_{Munich}$," *Human Genetic* 42(5):726-734.

Carlson, C.S. et al. (May 27, 2004). "Mapping Complex Disease Loci in Whole-Genome Association Studies," *Nature* 429(6990):446-452.

Chen, Y. et al. (Nov. 1999). "Selection and Analysis of an Optimized Anti-VEGF Antibody: Crystal Structure of an Affinity-Matured Fab in Complex with Antigen," *J. Mol. Biol.* 293(4):865-881.

Chen, J. et al. (Apr. 2000). "A Microsphere-Based Assay for Multiplexed Single Nucleotide Polymorphism Analysis Using Single Base Chain Extension," *Genome Res.* 10(4):549-557.

Cheung, V.G. et al. (Oct. 27, 2005). "Mapping Determinants of Human Gene Expression by Regional and Genome-Wide Association," *Nature* 437(7063):1365-1369.

Chong et al. "Association of interleukin-10 promoter polymorphisms with systemic lupus erythematosus," Genes and Immunity 5:484-492 (2004).

Clackson, T. et al. (Aug. 15, 1991). "Making Antibody Fragments Using Phage Libraries," *Nature* 352(6336): 624-628.

International Search Report on Patentability for International Patent Application No. PACT;US2010/051589.

Cornall, R.J, (1998). "B Cell Antigen Receptor Signalling in the Balance of Tolerance and Immunity," *Novartis Foundation Symposium* 215:21-40.

Cotton, R.G. et al. (Jun. 1988). "Reactivity of Cytosine and Thymine in Single-Base Pair Mismatches with Hydroxylamine and Osmium Tetroxide and its Application to the Study of Mutations," *Proc. Natl. Acad. Sci. USA* 85(12):4397-4401.

Couzin-Frankel. "As Questions Grow, Duke Halts Trials, Launches Investigation," *Science* 329:614-615, (Aug. 2010).

Criswell, L.A. et al. (2005). "Analysis of Families in the Multiple Autoimmune Disease Genetics Consortium (MADGC) Collection: the PTPN22 620W Allele Associates with Multiple Autoimmune Phenotypes," *Am J Hum Genet* 76(4):561-571.

Crow, M.K. (Feb. 28, 2008). "Collaboration, Genetic Associations, and Lupus Erythematosus," *New England J. Med.* 358(9):956-961.

Cunninghame Graham, D.D. et al. (Nov. 1, 2006). "Evidence for Unique Association Signals in SLE at the CD28-CTLA4-ICOS Locus in a Family-Based Study," *Human Molecular Genetics* 15(21):3195-3205.

D'Cruz, D.P. et al. (Feb. 17, 2007). "Systemic Lupus Erythermoatosus," *Lancet* 369(9561):587-596.

De Bakker, P.I.W. et al. (Oct. 2006, e-pub. Sep. 24, 2006). "A High-Resolution HLA and SNP Haplotype Map for Disease Association Studies in the Extended Human MHC," *Nat Genet* 38(10):1166-1172.

De Bakker, P.I.W. et al. (Nov. 2005, e-pub. Oct. 23, 2005). "Efficency and Power in Genetic Association Studies," *Nat Genet* 37(11):1217-1223.

De La Vega, F.M. et al. (Jun. 2002). "New Generation Pharmacogenomic Tools: A SNP Linkage Disequilibrium Map, Validated SNP Assay Resource, and High-Throughput Instrumentation System for Large-Scale Genetic Studies," *BioTechniques* 32(Supp, 6):S48-S50, S52, S54.

Delpech, A. et al. (1993). "Antibodies to Sm, RNP and SSB Detected by Solid-Phase ELISAs Using Recombinant Antigens: A Comparision Study With Counter Immunoelectrophoresis and Immunoblotting," *Journal of Clinical Laboratory Analysis* 7:197-202.

Delgado-Vega et al. "Fine mapping and conditional analysis identify a new mutation in the autoimmunity susceptibility gene BLK that leads to reduced half-life of the BLK protein," 71(7):1219-1226 (Jun. 13, 2012).

Del-Pozo et al. "Lack of evidence of a role of XBP1 and PRDM1 polymorphisms in Spanish patients with immunoglobulin A Deficiency" Hum Immunol 70:950-952 (2009).

Demirci, F.Y.K. et al. (2007). "Association of a Common Interferon Regulatory Factor 5 (*IRF5*) Variant with Increased Risk of Systemic Lupus Erythematosus (SLE)," *Ann Hum Genet* 71(Pt 3):308-311.

(56) References Cited

OTHER PUBLICATIONS

Deshmukh, H. et al. : Replication of the BANK1 genetic association with systemic lupus erythematosus in a European-derived population, BMC Proceedings, Bio Central Ltd. London UK, 3(7):531, (Dec. 15, 2009).
Duerr et al. "A genome-wide association study identifies IL23R as an inflammatory bowel disease gene," Science 314:1461-1463 (Dec. 1, 2006).
Deveu et al. "Cytokines that regulate autoimmunity," Curr Opin Immunol. 20:663-668 (2008).
Devlin, B et al. (2000). "Genomic Control for Association Studies: a Semiparametric Test to Detect Excess-Haplotype Sharing," *Biostatistics* 1(4):369-387.
Dewan, A, et al. (Nov. 10, 2006, e-pub. Oct. 19, 2006). "*HTRA1* Promoter Polymporphism in Wet Age-Related Macular Degeneration," *Science* 314(5801):989-992.
Dixon A.L. et al. (Oct. 2007, e-pub. Sep. 16, 2007). A Genome-Wide Association Study of Global Gene Expression, *Nat Genet* 39(10):1202-1207.
Dunne, J.L. et al. (2003). "Mac-1, but not LFA-1, Uses Intercellular Adhesion Molecule-1 to Mediate Slow Leukocyte Rolling in TNF-α-Induced Inflammation," *J Immunol* 171(11):6105-6111.
Dymecki, S.M. et al. (Mar. 5, 1992). "Structure and Developmental Regulation of the B-Lymphoid Tyrosine Kinase Gene blk," *J Biol Chem* 267(7):4815-4823.
Edberg, J.C. et al. (Apr. 15, 2008, E-Pub. Jan. 8, 2008). "Genetic Variation in the CRP Promoter: Association With Systemic Lupus Erythematosus," Hum Mol Genet 17(8):1147-1155.
Ehirchiou, D. et al. (Jul. 9, 2007, E-Pub. Jun. 11, 2007). "CD11LB Facilitates the Development of Peripheral Tolerance by Suppressing TH17 Differentiation," J Exp Med 204(7):1519-1524.
European Search Report dated Apr. 24, 2013, for European Patent Application No. 10822583.0, Filed on Oct. 6, 2010, 14 pages.
Evans, W.E. et al. (May 27, 2004). "Moving Towards Individualized Medicine with Pharmacogenomics," *Nature* 429(6990):464-468.
Faham, M. et al. (Aug. 1, 2001). "Mismatch Repair Detection (MRD): High-Throughput Scanning for DNA Variations," *Hum. Mol. Genet.* 10(16):1657-1664.
Faham, M. et al. (Oct. 11, 2005, e-pub. Oct. 3, 2005). "Multiplexed Variation Scanning for 1,000 Amplicons in Hundreds of Patients Using Mismatch Repair Detection (MRD) on Tag Arrays," *Proc. Natl Acad. Sci. USA* 102(41):14717-14722.
Falush, D. et al. (Aug. 2003). "Inference of Population Structure Using Multilocus Genotype Data: Linked Loci and Correlated Allele Frequencies," *Genetics* 164(4):1567-1587.
Falush, D. et al. (Jul. 2007). "Inference of Population Structure Using Multilocus Genotype Data: Dominant Markers and Null Alleles," *Molecular Ecology Notes* 7(4):574:578.
Fan, J-B. et al. (Jun. 2000). "Parallel Genotyping of Human SNPs Using Generic High-Density Oligonucleotide Tag Arrays," *Genome Res.* 10(6):853-860.
Fellouse, F.A. et al. (Aug. 24, 2004, e-pub. Aug. 11, 2004). "Synthetic Antibodies from a Four-Amino-Acid Code: A Dominant Role for Tyrosine in Antigen Recognition," Proc. Natl. Acad. Sci. USA 101(34):12467-12472.
Fernando, M.M.A, et al. (Nov. 3, 2007). "Identification of Two Independent Risk Factors for Lupus Within the MHC in United Kingdom Families," *PLoS Genet* 3(11):e192:2109-2121.
Fishwild, D.M. et al. (Jul. 1996). "High-Avidity Human IgGκ Monoclonal Antibodies From a Novel Strain of Minilocus Transgenic Mice," *Nature Biotechnol.* 14(7): 845-851.
Franke et al. "Sequence variants in IL10, ARPC2 and multiple other loci contribute to ulcerative colitis susceptibility," Nature Genetics 40(11):1319-1323 (Nov. 2008).
Frazer, K.A. et al. (Oct. 18, 2007). "A Second Generation Human Haplotype Map of Over 3.1 Million SNPs," *Nature* 449(7164). 851-861, Author Manuscript 30 pages.
Fu, Q. et al. (2008, e-pub. Sep. 15, 2008). "Association Elevated Transcript Levels of Interferon-Inducible Chemokines With Disease Activity and Organ Damage in Systemic Lupus Erythematosus Patients," *Arthritis Research & Therapy* 10(5)(R112):1-10.
Fung et al. "Analysis of 17 autoimmune disease-associated variants in type 1 diabetes identifies 6q23/TNFAIP3 as a susceptibility locus," Genes Immun 10:188-191 (2009).
Gaffney, P.M. et al. (Dec. 1988). "A Genome-Wide Serach for Susceptibility Genes in Human Systemic Lupus Erythematosus Sib-Pair Families," *Proc. Natl. Acad. Sci. USA* 95:14875-14879.
Gateva et al. "A large-scale replication study identifies TNIP1, PRDM1, JAZF1, UHRF1BP1 and IL10 as risk loci for systemic lupus erythematosus," Nature Genetics 41(11):1228-1233 (Nov. 2009).
Ge et al. "Global patterns of cis variation in human cells revealed by high-density allelic expression analysis," *Nature Genetics* 41(11):1216-1222.
Gibson et al. "Novel single nucleotide polymorphisms in the distal IL-10 promoter affect IL-10 production and enhance the risk of systemic lupus erythematosus," J Immunol 166:3915-3922 (2001).
Giglio, S. et al. (2001, e-pub. Feb. 26, 2001). "Olfactory Receptor-Gene Clusters, Genomic-Inversion Polymorphisms, and Common Chromosome Rearrangements," *Am J Hum Genet* 68(4):874-883.
Gill, J.M. et al. (Dec. 1, 2003). "Diagnosis of Systemic Lupus Erythematosus," *American Family Physician* 68(11):2179-2186.
Gold et al. "Variation in factor B (BF) and complement component 2 (C2) genes is associated with age-related macular degeneration," Nat Genet 38*4)?458-462 (Apr. 2006).
Goldberg, M.A. et al. (Mar.-Apr. 1976). "Histocompatibility Antigens in Systemic Lupus Erythematosus," *Arthritis Rheum* 19(2):129-132.
Graham, R.R. et al. (2001, e-pub. Jul. 17, 2001). "Genetic Linkage and Transmission Disequilibrium of Marker Haplotypes at Chromosome 1q41 in Human Systemic Lupus Erythematosus," *Arthritis Research* 3(5):299-305.
Graham, R.R. et al. (2002). "Visualizing Human Leukocyte Antigen Class II Risk Haplotypes in Human Systemic Lupus Erythematosus," *Am J Hum Genet* 71(3):543-553.
Graham, R.R. et al. (May 2006, e-pub. Apr. 16, 2006). "A Common Haplotype of Interferon Regulatory Factor 5 (*IRF5*) Regulates Splicing and Expression and is Associated with Increased Risk of Systemic Lupus Erythematosus," *Nat Genet* 38(5):550-555.
Graham, R.R. et al. (Apr. 17, 2007). "Three Functional Variants of IFN Regulatory Factor 5 (*IRF5*) Define Risk and Protective Haplotypes for Human Lupus," *Proc Natl Acad Sci U S A* 104(16):6758-6763.
Graham, R.R. et al. (2007). "Specific Combinations of HLA-DR2 and DR3 Class II Haplotypes Contribute Graded Risk for Disease Susceptibility and Autoantibodies in Human SLE," *Eur J Hum Genet* 15(8):823-830.
Graham, D.S.C. et al. (Jan. 2008, e-pub. Dec. 2, 2007). "Polymorphism at the TNF Superfamily Gene *TNFSF4* Confers Susceptibility to Systemic Lupus Erythematosus," *Nature Gentics* 40(1):83-89.
Graham, R.R. et al. (Sep. 2008, Aug. 1, 2008). "Genetic Variants Near TNFAIP3 on 6q23 are Associated with Systemic Luus Erythematosus," *Nature Genetics* 40(9):1059-1061.
Graham, R.R. et al. (2009). Review of Recent Genome-Wide Association Scans in Lupus, *Journal of Internal Medicine* 265:680-688.
Grossman, P.D. et al. (Oct. 25, 1994). "High-Density Multiplex Detection of Nucleic Acid Sequences: Oligonucleotide Ligation Assay and Sequence-Coded Separation," *Nuc. Acids Res.* 22(21):4527-4534.
Gunderson, K.L. et al. (2006). "Whole-Genome Genotyping," *Methods Enzymol* 410:359-376.
Hammerberg, C. et al. (Apr. 6, 1998). "Activated Complement Component 3 (C3) is Required for Ultraviolet Induction of Immunosuppression and Antigenic Tolerance," *J Exp Med* 187(7):1133-1138.
Hampe, J. et al. (Feb. 2007, e-pub. Dec. 31, 2006). "A Genome-Wide Association Scan of Nonsynonymous SNPs Identifies a Susceptibility Variant for Crohn Disease in *ATG16L1*," *National Genet.* 39(2):207-211.
Harley, J.B. et al. (1998). "The Genetics of Human Systemic Lupus Erythematosus," *Current Opinion in Immunology* 10:690-696.

(56) References Cited

OTHER PUBLICATIONS

Harley, J.B. et al. (Feb. 2008, e-pub. Jan. 20, 2008). "Genome-Wide Association Scan in Women with Systemic Lupus Erythematosus Identifies Susceptibility Variants in *ITGAM, PXK, KIAA1542* and Other Loci," *Nature Genetics* 40(2):204-210.

Harris, W.J. (Nov. 1995). "Production of Humanized Monoclonal Antibodies for in Vivo Imaging and Therapy," *Biochem. Soc. Transactions* 23(4):1035-1038.

Hartung, K. et al. (Oct. 1992). "Major Histocompatibility Complex Haplotypes and Complement C4 Alleles in Systemic Lupus Erythematosus. Results of a Multicenter Study," *J Cl in. Invest.* 90(4):1346-1351.

Hawkins, R.E. et al (Aug. 5, 1992). "Selection of Phage Antibodies by Binding Affinity. Mimicking Affinity Maturation," *J. Mol. Biol.* 226(3):889-896.

Heyninck et al. "Structure-function analysis of the A20-binding inhibitor of NF-kappa B activation, ABIN-1," FEBS Lett 536:135-140 (2003).

Hirschhorn et al. "A Comprehensive Review of Genetic Association Sutdies," *Genetics in Medicine* 4(2):45-61, ( Mar. 2002).

Hirschhorn, J.N, et al. (Feb. 2005). "Genome-Wide Association Studies for Common Diseases and Complex Traits," *Nature Reviews* 6(2):95-108.

Hochberg. M.G. (Sep. 1997). "Updating the American College of Rheumatology Revised Criteria for the Classification of Systemic Lupus Erythematosus," *Arthritis Rheum* 40(9):1725.

Hollinger, P. et al. (Jul. 15, 1993). "'Diabodies': Small Bivalent and Bispecific Antibody Fragments," *Proc. Natl. Acad. Sci. USA* 90(14):6444-6448.

Holman, H.R. (Jun. 1965). "Partial Purification and Characterization of an Extractible Nuclear Antigen Which Reacts with SLE Sera," *Annals New York Academy of Sciences* pp. 800-806.

Hom, G. et al. (Feb. 28, 2008, e-pub. Jan. 20, 2008). "Association of Systemic Lupus Erythematosus with *C8orf13-BLK* and *ITGAM-ITGAX*," *N Engl J Med* 358(9):900-909.

Hoogenboom, H.R. et al.(Aug. 11, 1991). "Multi-Subunit Proteins on the Surface of Filamentous Phage: Methodologies for Displaying Antibody (Fab) Heavy and Light Chains," *Nuci. Acids Res.* 19(15):4133-4137.

Hsu, T.M. et al. (Sep. 2001). "Universal SNP Genotyping Assay with Fluorescence Polarization Detection," *Biotechniques* 31(3):560.

Hudson, P.J. et al. (Jan. 2003). "Engineered Antibodies," *Nat. Med.* 9(1):129-134.

Hurle, M.R. et al. (Aug. 1994). "Protein Engineering Techniques for Antibody Humanization," *Curr. Op. Biotech.* 5(4):428-433.

Hynes, R.O. (Apr. 3, 1992). "Integrins: Versatility, Modulation, and Signaling in Cell Adhesion," *Cell* 69(1):11-25.

Illei, G.G. et al. (Jun. 2004). "Biomarkers in Systemic Lupus Erythematosus. 1. General Overview of Biomarkers and Their Applicability," *Arthritis & Rheumatism* 50(6):1709-1720.

International Multiple Sclerosis Genetics Consortium (IMSGC), "The expanding Genetic Overlap Between Multiple Slerosis and Type I diabetes" Genes and Immunity 10:11-14 (2009).

International Search Report dated May 26, 2009, for PCT Application No. PCT/US2008/064430, filed on May 21, 2008, ten pages.

International Search Report dated Jul. 29, 2010, for PCT Application No. PCT/US2009/058478, filed on Sep. 25, 2009, seven pages.

Ioannidis et al. "Replication Validity of Genetic Association Studies," Nature Genetics 29:306-309, (Nov. 2001, e-pub. Oct. 15, 2001).

Ito et al "Replication of the association between the C8orf13-BLK region and systemic lupus erythematosus in a Japanese population," Arthritis & Rheumatism 60(2):553-558, (Feb. 1, 2009).

Jackson, J.R. et al. (Apr. 1, 1995). "In Vitro Antibody Maturation. Improvement of a High Affinity, Neutralizing Antibody Againist IL-1 β," *J. Immunol.* 154(7):3310-3319.

Jackson et al. "Noise Amidst the Silence: Off-Target Effects of siRNAs?," *Trends in genetics* 20(11):521-524, (2004).

Jacob, C.O. et al. (Dec. 2007). "Identification of Novel Susceptiblity Genes in Childhood-Onset Systemic Lupus Erythematosus Using a Uniquely Designed Candidate Gene Pathway Platform," *Arthritis Rheum* 56( 12):4164-4173.

Jacob et al. "Identification of IRAK1 as a risk gene with critical role in the pathogenesis of systemic lupus erythematosus," PNAS USA 106(15):6256-6261 (Apr. 14, 2009).

Jakobovits, A. et al. (Mar. 1993). "Analysis of Homozygous Mutant Chimeric Mice: Deletion of the Immunoglobin Heavy-Chain Joining Region Blocks B-Cell Development and Antibody Production," *Proc. Natl. Acad. Sci. USA* 90(6):2551-2555.

Jakobovits, A. et al. (Mar. 18, 1993). "Germ-Line Transmission and Expression of a Human-Derived Yeast Artficial Chromosome," Nature 362(6417):255-258.

Johnansson et al. "Common Variants in the JAZF1 Gene Associated With Height Identified by Linkage and Genome-Wide Association Analysis," Hum Mol Genet 18(2):373-380 (2008).

Jones, P.T. et al. (May 29, 1986). "Replacing the Complementarity-Determining Region in a Human Antibody with Those from a Mouse," *Nature* 321(6069):522-525.

Juven-Gershon et al. "Regulation of gene expression via the core promoter and the basal transcriptional machinery," Dev Biol 339:225-229 (2010).

Khan, W.N. et al. (1995). "Defective B Cell Development and Function in Btk-Deficient Mice," *Immunity* 3(3):283-299.

Klein et al. "Continuous lymphoid cell lines with characteristics of B cells (bone-marrow-derived), lacking the Epstein-Barr virus genome and derived from three human lymphomas," Proc Natl Acad Aci USA 71(8):3283-3286 (Aug. 1974).

Kohler, G. et al. (Aug. 7, 1975). "Continuous Cultures of Fused Cells Secreting Antibody of Predefined Specificity," *Nature* 256(5517):495-497.

Kosoy et al. "Ancestry informative marker sets for determining continental origin and admixture proportions in common populations in America," Hum MUTAT 30:69-78 (2009).

Kozbor, D. et al. (Dec. 1984). "A Human Hybrid Myeloma for Production of Human Monoclonal Antibodies," *J. Immunol* 133(6):3001-3005.

Kozyrev, S.V. et al. (Feb. 2008, e-pub. Jan. 20, 2008). "Functional Variants in the B-Cell Gene *BANK1* are Associated with Systemic Lupus Erythematosus," *Nat Genet* 40(2)211-216, Corrigedna (Apr. 2008). "Corrigendum: Functional Variants in the B-Cell Gene *BANK1* are Associated with Systemic Lupus Erythematosus," *Nat Genet* 40(4)484.

Kuhn, R.M. et al., (Jan. 2007, e-pub. Nov. 16, 2006). "The UCSC Genome Browser Database: Update 2007," 35(database issue):D668-673.

Kumar, K.R. et al. (Jun. 16, 2006). "Regulation of B Cell Tolerance by the Lupus Susceptibility Gene *Ly108*," *Science* 12(5780):1665-1669.

Kyogoku, C. et al. (Sep. 2004, e-pub. Jul. 23, 2004). "Genetic Association of the R62W Polymorphism of Protein Tyrosine Phosphatase PTPN," *Am J Hum Genet* 75(3)504-507.

Lee, C.V. et al. (Jan. 2004). "Bivalent Antibody Phage Display Mimics Natural Immunoglobulin," *J Immunol. Methods* 284(1-2): 119-132.

Lee, C.V. et al. (Jul. 23, 2004). "High-Affinity Human Antibodies From Phage-Displayed Synthetic Fab Libraries With Single Framework Scaffold," *J. Mol. Biol.* 340(5):1073-1093.

Lee, Y.H. et al. (Jan. 2007, e-pub. Jun. 7, 2006). "The PTPN22 C1858T Functional Polymorphism and Autoimmune Diseases—A Meta-Analysis," *Rheumatology* 46(1):49-56.

Lerner, M.R. et al. (Nov. 1979). "Antibodies to Small Nuclear RNAs Complexed With Proteins are Produced With Systemic Lupus Erythematosus," *PNAS USA* 76(11):5495-5499.

Lerner, M.R. et al. (Jan. 23, 1981). "Two Novel Classes of Small Ribonucleoproteins Detected by Antibodies Associated With Lupus Erythematosus," *Science* 211:400-402.

Lettre, G. et al. (May 2008, e-pub. Apr. 6, 2008). "Identification of Ten Loci Associated with Height Highlights New biological Pathways in Human Growth," *Nat Genet* 40(5):584-591, 21 pages.

(56) References Cited

OTHER PUBLICATIONS

Li et al. "Mach 1.0: Rapid Haplotype Reconstruction and Missing Genotype Inference," ASHG Annual Meeting 2006, S79, Program Nr. 2290, abstract only, 1 page, (2006).
Lin et al. "Transcription of the blk Gene in Human B Lymphocytes is Controlled by Two Promoters," J Biol Chem 270(43):25968-25975 (Oct. 27, 1995).
Liu et al. "IFIH1 polymorphisms are significantly associated with type 1 diabetes and IFIH1 gene expression in peripheral blood mononuclear cells," Hum Molec Genet 18(2);358-365 (2009).
Loannidis et al. "Replication Validity of Genetic Association Studies," *Nature Genetics* 29:306-309, (Nov. 2001).
Lonberg, N. et al. (Apr. 28, 1994). "Antigen-Specific Human Antibodies from Mice Comprising Four Distinct Genetic Modifications," *Nature* 368(6474):856-859.
Lonberg, N. et al. (1995). "Human Antibodies from Transgenic Mice," *Int. Rev. Immunol.* 13(1):65-93.
Lu, H. et al. (Mar. 1997). "LFA-1 is Sufficient in Mediating Neutrophil Emigration in Mac-I-Deficient Mice," *J Clin Invest* 99(6):1340-1350.
Maller, J. et al. (Sep. 2006, e-pub. Aug. 27, 2006). "Common Variation in Three Genes, Including a Noncoding Variant in CFH, Strongly Infuences Rish of Age-Related Macular Degeneration," *Nat Genet* 38(9):1055-1059.
Marchini et al. "A new multipoint method for genome-wide association studies by imputation of genotypes," Nat Genet 39:906-913 (2007).
Marks, J.D. et al. (Dec. 5, 1991). "By-Passing Imunization. Human Antibodies From V-Gene Libraries Displayed on Phage," *J Mol. Biol.* 222(3):581-597.
Marks, J..D. et al. (Jul. 1992). "By-Passing Immunication: Building High Affinity Human Antibodies by Chain Shuffling," *Bio. Technology* 10(7): 779-783.
Marshak-Rothstein, A. et al.. (2007, e-pub. Dec. 19, 2006). "Immunologically Active Autoantigens: The Role of Toll-Like Receptors in the Development of Chronic Inflammatory Disease," Annu. Rev. Immunol. 25:419-441.
Matarin, M. et al. (May 2007, e-pub. Mar. 30, 2007). "A Genome-Wide Genotyping Study in Patients with Ischaemic Stroke: Initial Analysis and Data Release," *Lancet Neurology* 6(5):414-420.
May et al "How Many Species are There on Earth?," Science 241:1441-1449, (Sep. 16, 1988).
McClay, J.L. et al. (Feb. 2002). "High-Throughput Single-Nucleotide Polymorphism Genotyping by Fluorescent Competitive Allele-Specific Polymerase Chain Reaction (SNiPTag)," *Analytical Biochem.* 301(2):200-206.
Mhlanga, M.M. et al. (Dec. 2001). "Using Molecular Beacons to Detect Single-Nucleotide Polymorphisms with Real-Time PCR," *Methods* 25(4):463-471.
Mitchell, M.K. et al. (2004). "The New York Cancer Project: Rationale, Organization, Design, and Baseline Characteristics.," *J Urban Health* 81(2):301-310.
Miyagi, T. et al. (Oct. 1, 2007, e-pub. Sep. 10, 2007). "High Basal STAT4 Balanced by STAT1 Induction to Control Type 1 Interferon Effects in Natural Killer Cells," *J Exp Med* 204(10):2383-2396.
Moffatt, M.F. et al. (Jul. 26, 2007). "Genetic Variants Regulating *ORMDL3* Expression Contribute to the Risk of Childhood Asthma," *Nature* 448(7152):470-474.
Mordenti, J. et al. (Nov. 8, 1991). "Interspecies Scaling of Clearance and Volume of Distribution Data for Five Therapeutic Proteins," *Pharmaceut. Res* 8(11):1351-1359.
Morrison, S.L. et al. (Nov. 1984). "Chimeric Human Antibody Molecules: Mouse Antigen-Binding Domains with Human Constant Region Domains," *Proc. Natl. Acad. Sci. USA* 81(20):6851-9855.
Morrison, S.L. (Apr. 28, 1994). "Immunology. Success in Specification," *Nature* 368(6474):812-813.
Musone, S.I. et al. (Sep. 2008, e-pub. Aug. 1, 2008). "Multiple Polymorphisms in the *TNFAIP3* Region are Independently Associated With Systemic Lupus Erythematosus," *Nature Genetics* 40(9):1062-1064.

Myers, R.M. et al. (Feb. 7-13, 1985) "Detection of Single Base Substitutions in Total Genomic DNA," *Nature* 313(6002):495-498.
Myers, R.M. et al. (Dec. 13, 1985). "Detection of Single Base Substitutions by Ribonuclease Cleavage at Mismatches in RNA:DNA Duplexes," Science 230(4731):1242-1246.
Nair et al. "Genome-Wide Scan Reveals Association of Psoriasis With IL-23 and NF-KAPPAB Pathways," Nat Genet 41(2):199-204 (Feb. 2009).
Nath, S.K. et al. (Dec. 2004, e-pub. Oct. 1, 2004). "Genetics of Human Systemic Lupus Erythematosus: the Emerging Picture," *Curr Opin Immunol* 16(6):794-800.
Nath, S.K. et al. (Feb. 2008, e-pub. Jan. 20, 2008). "A Nonsynonymous Functional Variant in Integrin-$\alpha_M$ (Encoded by *ITGAM*) is Associated with Systemic Lupus Erythematosus," *Nat Genet* 40(2):152-154.
Nath et al. "Polymorphisms of complement receptor 1 and interleukin-10 genes and systemic lupus erythematosus: a meta-analysis," Hum Genet 118:225-234 (2005).
NCBI "Db SNP ss 24482749, dbsNP Short Gene Variations," located at <http://www.ncbi.nlm.nih.gov/projects/SNP/snp_ss.cgi?subsnp_id=24482749>, last visited on Jul. 3, 2013, 2 pages, (Aug. 21, 2004).
NCBI SNP Database No. ss3203424, last updated Sep. 5, 2001, located at <http://www.ncbi.nlm.nih.gov/projects/SNP/snp_ss.cgi?subsnp_idCB20324,> last visited on May 10, 2013, one page.
NCBI SNP Database No. ss38786888, located at <http://www.ncbi.nlm.nih.gov/projects/SNP/snp_ss.cgi?subsnp_id=378688,> last visited on Oct. 9, 2012, seven pages.
NCBI SNP Database No. rs922483, located at <http://www.ncbi.nlm.nih.gov/projects/SNP/snp_ref.cgi?r=rs6568431,> last visited on Oct. 4, 2013, two pages.
NCBI SNP Database No. rs6568431, located at <http://www.ncbi.nlm.nih.gov/projects/SNP/snp_ref.cgi?r=rs6568431,> last visited on Nov. 7, 2011, two pages.
NCBI SNP Database No. rs2187668, located at <http://www.ncbi.nlm.nih.gov/projects/SNP/snp_ref.cgi?r=rs2187668,> last visited on Nov. 7, 2011, three pages.
NCBI SNP Database No. ss66547003, located at http://www.ncbi.nlm.nih.gov/projects/SNP/snp_ss.cgi?subsnp_id=66547003, last visited on Mar. 19, 2013.
Nemazee D. et al. (Jun. 5, 2000). "Revising B Cell Receptors," *J Exp Med* 191(11):1813-1817.
Neuberger, M. (Jul. 1996). "Generating High-Avidity Human Mabs in Mice," *Nature Biotechnol.* 14(7):826.
Newton, C.R. et al. (Apr. 11, 1989). "Analysis of any Point Mutation in DNA. The Amplification Refractory Mutation System (ARMS)," *Nucleic Acids Research*, 17(7):2503-2516.
Ng, K.P. et al. (2007). "B Cell Depletion Therapy in Systemic Lupus Erythematosus: Long-Term Follow-Up and Predictors of Response," *Ann Rheum Dis* 66:1259-1262.
Oishi, T et al. (2008, e-pub. Jan. 25, 2008). "A Functional SNP in the NKX2.5-Binding Site of ITPR3 Promoter is Associated with Susceptibility to Systemic Lupus Erythematosus in Japanese Population," *J Hum Genet* 53(2):151-162.
Olsson, L.M. et al. "Allelic Imbalance of BLK Detected in CD4 T Cells Suggesting That BLK Acts Via T Cell Pathways in Autoimmune Pathogenesis," The 2009 ACR/ARHP Annual Scientific Meeting Philadelphia Oct. 16-21, 2009.
Orita, M. et al. (Apr. 1989). "Detection of Ploymorphisms of Human DNA by Gel Electrophoresis as Single-Strand Conformation Polymorphisms," *Proc. Natl. Acad. Sci. USA* 86(8):2766-2770.
Orita, M, et al. (Nov. 1989). "Rapid and Sensitive Detection of Point Mutations and DNA Polymorphisms Using the Polymerase Chain Reaction," Genomics 5(4):874-879.
Pääbo, S. (Jan. 23, 2003). "The Mosaic That is Our Genome," Nature 421(6921):409-412.
Palomino-Morales, R.J. et al. (2008, e-pub. Apr. 24. 2008). "*STAT4* but not *TRAF1/C5* Variants Influence the Risk of Developing Rheumatoid Arthritis and Systemic Lupus Erythematosus in Colombians," *Genes and Immunity* 9:379-382.
Pastinen, T. et al. (Jun. 1997) "Minisequencing: A Specific Tool for DNA Analysis and Diagnostics on Oligonucleotide Arrays," *Genome Res.* 7(6):606-614.

(56) References Cited

OTHER PUBLICATIONS

Pe'er I, et al. (Jun. 2006, e-pub. May 21, 2006). "Evaluating and Improving Power in Whole-Genome Association Studies Using Fixed Marker Sets," *Nat Genet* 38(6):663-667.
Peiffer et al. "SNP-CGH Technologies for Genomic Profiling of LOH and Copy Number," *Clin. Lab Int.*, pp. 1-3, (May 2006).
Plenge, R.M. et al. (Sep. 20, 2007, e-pub. Sep. 5, 2007). "*TRAF1-C5* as a Risk Locus for Rheumatoid Arthritis—A Genomewide Study," *N Engl J Med* 357(12):1199-1209.
Pourmand, N. et al. (1999). "Ro/SSA and La/SSB Specific IgA Autoantibodies in Serum of Patients with Sjögren's Syndrome and Systemic Lupus Erythematosus," *Ann Rheum Dis* 58:623-629.
Prahalad et al. "Variants in TNFAIP3, STAT4, and C12orf30 loci associated with multiple autoimmune diseases are also associated with juvenile idiopathic arthritis," Arthritis and Rheumatism 60(7):2124-2130 (Jul. 2009).
Presta, L. G. (Aug. 1992). "Antibody Engineering," *Curr. Op. Struct. Biol.* 2(4):593-596.
Price A.L. et al. (Aug. 2006, e-pub. Jul. 23, 2006). "Principal Components Analysis Corrects for Stratification in Genome-Wide Association Studies," *Nat Genet* 38(8):904-909.
Pritchard, J.K. et al. (Jun. 2000). "Inference of Population Structure Using Multilocus Genotype Data," *Genetics* 155(2):945-959.
Prokunina, L. et al., (Dec. 20, 2002, e-pub. Oct. 28, 2002). "A Regulatory Polymorphism in *PDCD1* is Associated with Susceptibility to Systemic Lupus Erythematosus in Humans," *Nat Genet* 32(4):666-669.
Purcell S. et al. (Sep. 2007, e-pub. Jul. 25, 2007). "A Tool Set for Whole-Genome Association and Population-Based Linkage Analyses," *Am J Hum Genet* 81(3):559-575.
Ranade, K. et al. (Jul. 2001). "High-Throughput Genotyping With Single Nucleotide Polymorphisms," *Genome Res.* 11(7):1262-1268.
Reddy, M.V. et al. (Dec. 2005). "The R620W C/T Polymorphism of the Gene PTPN22 is Associated With SLE Independently of the Association of PDCD1," *Genes and Immunity* 6(8):659-662.
Remmers, E.F. et al. (Sep. 6, 2007). "*STAT4* and the Risk of Rheumatoid Arthritis and Systemic Lupus Erythematosus," *N Engl J Med* 357(10):977-986.
Riechmann, L. et al. (Mar. 24, 1988). "Reshaping Human Antibodies for Therapy," *Nature* 332(6162):323-327.
Rönnblom, L. et al. (Dec. 17, 2001). "A Pivotal Role for the Natural Interferon α-Producing Cells (Plasmacytoid Dendritic Cells) in the Pathogenesis of Lupus," *J Exp Med* 194(12):F59-F63.
Ruano, G. et al. (Oct. 1989). "Direct Haplotyping of Chromosomal Segments From Multiple Heterozygotes Via Allele-Specific PCR Amplification," *Nucleic Acids Research* 17(20):8392.
Saiki, R.K. et al. (Jan. 29, 1988). "Primer-Directed Enzymatic Amplication of DNA with Thermostable DNA Polymerase," *Science* 239(4839):487-491.
Sawalha, A.H. et al. (Mar. 5, 2008). "Common Variants Within MECP2 Confer Risk of Systemic Lupus Erythematosus," *Plos One* 3(3)(e1727):1-7.
Saxena, R. et al. (Jun. 1, 2007, e-pub. Apr. 26, 2007). "Genome-Wide Association Analysis Identifies Loci for Type 2 Diabetes and Triglyceride Levels," *Science* 316(5829):1331-1336.
Schier, R. et al.(Mar. 9, 1996). "Identification of Functional and Structural Amino-Acid Residues by Parsimonious Mutagenesis," *Gene* 169(2):147-155.
Scott, L.J. et al. (Jun. 1, 2007, e-pub. Apr. 26, 2007). "A Genome-Wide Association Study of Type 2 Diabetes in Finns Detects Multiple Susceptibility Variants," *Science* 316(5829):1341-1345.
Scuteri A. et al. (Jul. 2007). "Genome-Wide Association Scan Shows Genetic Variants in the FTO Gene are Associated with Obesity-Related Traits," *PLoS Genet* 3(7)(e115)1200-1210.
Seligman, V.A. et al. (Mar. 2001). "The Fcγ Receptor IIIA-158F Allele is a Major Risk Factor for the Development of Lupus Nephritis Among Caucasians but not Non-Caucasians," *Arthritis Rheum* 44(3):618-625.
Sestack et al. "Current status of Lupus Genetics," *Arthritis Research & Therapy* 9(210):1-9, (2007, e-pub. May 17, 2007).

Shen, R. et al. (Mar. 15, 2003). "Optimization of Production-Scale Genotyping," *Genetic Engineering News* 23:34-38.
Shenk, T.E. et al. (Mar. 1975). "Biochemical Method for Mapping Mutational Alterations in DNA with S1 Nuclease: The Location of Deletions and Temperature-Sensitive Mutations in Simian Virus 40," *Proc. Natl. Acad. Sci. USA*, 72(3):989-993.
Shi, M.M. (Feb. 2001). "Enabling Large-Scale Pharmacogenetic Studies by High-Throughput Mutation Detection and Genotyping Technologies," *Clin. Chem.* 47(2):164-172.
Sidhu, S.S. et al. (Apr. 23, 2004). "Phage-Displayed Antibody Libraries of Synethitic Heavy Chain Complementarity Determining Regions," *J. Mol. Biol.* 338(2):299-310.
Sigurdsson, S. et al. (2005, e-pub. Jan. 18, 2005). "Polymorphisms in the Tyrosine Kinase 2 and Interferon Regulatory Factor 5 Genes are Associated With Systemic Lupus Erythematosus," *Am J Hum Genet* 76(3):528-537.
Sigurdsson, S. et al. (2008, e-pub. Dec. 6, 2007). "Comprehensive Evaluation of the Genetic Variants of Interferon Regulatory Factor 5 (IRF5) Reveals a Novel 5 Bp Length Polymorphism as Strong Risk Factor Systemic Lupus Erythematosus," *Human Molecular Genetics* 17(6):872-881.
Sladek, R. et al. (Feb. 22, 2007, e-pub. Feb. 11, 2007). "A Genome-Wide Association Study Identifies Novel Risk Loci for Type 2 Diabetes," *Nature* 445(7130):881-828.
Smyth et al. "A genome-wide association study of nonsynonymous SNPs identifies a type 1 diabetes locus in the interferon-induced helicase (IFIH1) region," Nat Genet 38(6):617-619 (Jun. 2009).
Sohn, J.H. et al. (2003). "Tolerance is Dependent on Complement C3 Fragment iC3b Binding to Antigen-Presenting Cells," *Nat Med* 9(2):206-212, Author Manuscript 15 pages.
Sticherling et al. "Diagnostic Approach and Treatment of Cutaneous Lupus Erythematosus," *JDDG* 6:48-61, (2008).
Stranger, B.E. et al. (Oct. 2007, e-ub. Sep. 16, 2007). "Population Genomics of Human Gene Expression," *Nat Genet* 39(10):1217-1224.
Sugawara, H et al. (2003). "Complex Low-Copy Repeats Associated With a Common Polymorphic Inversion at Human Chromosome 8p23," *Genomics* 82(2):238-244.
Sutherland et al. "Genomic polymorphism at the interferon-induced helicase (IFIH1) locus contributes to Graves' disease susceptibility," J Clin Endocrinol Metab 92(8):3338-3341 (2007).
Tan, E.M. et al.(1982). "The—1982 Revised Criteria for the Classification of Systemic Lupus Erythematosus" *Arth Rheum* 25:1271-1277.
Texido O. et al. (2000). "The B-Cell-Specific Src-family Kinase Blk is Dispensable for B-Cell Development and Activation," *Mol Cell Biol* 20(4):1227-1233.
Thomas et al. "Multiple loci identified in a genome-wide association study of prostate cancer," Nat Genet 40(3):310-315 (Mar. 2008).
Thorburn et al. Association of PDCD1 Genetic Variation With Risk and Clinical Manifestations of Systemic Lupus Erythematosus in a Multiethnic Cohort, Genes Immun 8:279-287 (2007).
Tian et al. "Analysis and Application of European Genetic Substructure Using 300 K SNP Information," Plos Genet 4(1):E4 (0029-0039) (2008).
Tsukada, S. et al. (Jan. 29, 1993). "Deficient Expression of a B Cell Cytoplasmic Tyrosine Kinase in Human X-Linked Agammaglobulinemia," *Cell* 72(2):279-290.
Turner, J. G. et al. (2001). "Anti-CD40 Antibody Induces Antitumor and Antimetastastic Effects: The Role of NK Cells," *The Journal of Immunology* 166:89-94.
Tyagi, S. et al. (Jan. 1998). "Multicolor Molecular Beacons for Allele Discrimination," *Nature Biotech.* 16(1):49-53.
Unoki et al. "ICBP90, an E2F-1 target, recruits HDAC1 and binds to methyl-CpG through its SRA domain," Oncogene 23:7601-7610 (2004).
Vaswani, S.K. et al. (Aug. 1998). "Humanized Antibodies as Potential Therapeutic Drugs," *Ann. Allergy, Asthma & Immunol.* 81(2):105-119.
Wakeland, E.K. et al. (Sep. 2001). "Delineating the Genetic Basis of Systemic Lupus Erythematosus," *Immunity* 15(3):397-408.

(56) References Cited

OTHER PUBLICATIONS

Wasserman, R. et al. (1995). "Differential Expression of the Blk and Ret Tyrosine Knases During B Lineage Development is Dependent on Ig Rearrangement," *J Immunol* 155(2):644-651.

Watts, G.M. et al. (2005). "Manifestations of Inflammatory Arthritis are Critically Dependent on LFA-1," *J Immunol* 174(6):3668-3675.

Wellcome Trust Case Control Consortium. (Jun. 2007). "Genome-Wide Association Study of 14,000 Cases of Seven Common Diseases and 3,000 Shared Controls," *Nature* 447 (7145):661-678.

Winter, E. et al. (Nov. 1985). "A Method to Detect and Characterize Point Mutations in Transcribed Genes: Amplification and Overexpression of the Mutant c-Ki-ras Allele in Human Tumor Cells," *Proc. Natl. Acad. Sci. USA* 82(22):7575-7579.

Written Opinion dated May 26, 2009, for PCT Application No. PCT/US2008/064430, filed on May 21, 2008, twelve pages.

Written Opinion dated Jul. 29, 2010, for PCT Application No. PCT/US2009/058478, filed on Sep. 22, 2009, seven pages.

Wu, D.Y. et al. (May 1989). "The Ligation Amplification Reaction (LAR)—Amplification of Specific DNA Sequences Using Rounds of Template-Dependent Ligation," *Genomics* 4(4):560-569.

Yang, W. et al. ":Population differences in SLE susceptibility genes: STAT4 and BLK, but not PXK, are associated with systemic lupus erythematosus in Hong Kong Chinese," Genes and Immunity 10(3):219-226.

Yao, Z. et al. (Aug. 1993). "DNA Typing for HLA-DPB1-Alleles in German Patients with Systemic Lupus Erythematosus Using the Polymerase Chaing Reaction and DIG-ddUTP-Lablelled Oligonucleotide Probes. Members of SLE Study Group," *Eur J Immunogenet* 20(4):259-266.

Ye, F. et al. (Apr. 2001). "Flurorscent Microsphere-Based Readout Technology for Multiplexed Human Single Nucleotide Polymorphism Analysis and Bacterial Indentification," *Hum. Mut.* 17(4):305-316.

Yelton, D.E. et al. (Aug. 1995). "Affinity Maturation of the BR96 Anti-Carcinoma Antibody by Condon-Based Mutagenesis," *J. Immunol.* 155(4):1994-2004.

Zeggini, E. et al. (Jun. 1, 2007, e-pub. Apr. 26, 2007). "Replication of Genome-Wide Association Signals in UK Samples Reveals Risk Loci for Type 2 Diabetes," *Science* 316(5829):1336-1341.

Zhernakova et al. "Detecting Shared Pathogenesis From the Shared Genetics of Immune-Related Diseases," Nat Rev Gent 10:43-55 (Jan. 2009).

Alfonso, S.D. et al. (Jan. 1, 2002). "Association Test With Systemic Lupus Erythematosus (SLE) of L10 Markers Indicate a Direct Involvement of a CA Repeat in the 5' Regulatory Region," *Genes and Immunity* 3(8):454-463.

Carr, E.J. et al. (Dec. 1, 2009). "Confirmation of the Genetic Association of CTLA4 and PTPN22 With ANCA-Associated Vasculitis," *BMS Medical Genetics* 10(1):121.

Chen, R. et al. (Dec. 5, 2008). "FitSNPS: Highly Differentially Expressed Genes are More Likely to Have Variants Associated With Disease," *Genome Biology* 9(12):R170.

Hall, M.A. et al. (Feb. 1, 2000). "Genetic Polymorphism of IL-12 p40 Gene in Immune-Mediated Disease," *Genes and Immunity.* 1(3):219-224.

Han, J-W. et al. (Nov. 1, 2009). "Genome-Wide Association Study in a Chinese Han Population Identifies Nine New Susceptibility Loci for Systemic Lupus Erythematosus," *Nature Genetics* 41(11):1234-1237.

Hirankarn, N. et al. (Nov. 25, 2008). "Association of IL-18 Gene Polymorphism (−137C) with Arthritis Manifestations in SLE: Combined Effect with IFN Gamma Gene Polymorphism (+874A)," *Clinical Rheumatology* 28(2):219-223.

Kawasaki, A. et al. (Sep. 17, 2010). "Association of TNFAIP3 Interacting Protein 1, TNIP1 With Systemic Lupus Erythematosus in a Japanese Population: A Case-Control Association Study," *Arthritis Research and Therapy* 12(5):R174.

Lazarus, M. et al. (Dec. 1, 1997). "Genetic Variation in the Interleukin 10 Gene Promoter and Systemic Lupus Erythematosus," *Journal of Rheumatology* 24(12):2314-2317.

Mehrian, R. et al. (Apr. 1998). Synergistic Effect Between *IL-10* and *bcl-2* Genotypes in Determining Susceptibility to Systemic Lupus Erythematosus, *Arthritis & Rheumatism* 41(4):596-602.

Mok, C.C. et al. (Jun. 1, 1998). "Interleukin-10 Promoter Polymorphisms in Southern Chinese Patients With Systemic Lupus Erythematosus," *Arthritis & Rheumatism* 41(6):1090-1095.

Porcel, J.M. et al. (Jan. 1, 1985). "The Value of Complement Activation Products in the Assessment of Systemic Lupus Erythematosus Flares," *Clinical Immunology and Immunopathology* 74(3):283-288.

Sánchez, E. et al. (Sep. 1, 2005). "Interleukin 12 (IL12B), Interleukin 12 Receptor (IL12RB1) and Interleukin 23 (IL23A) Gene Polymorphism in Systemic Lupus Erythematosus," *Rheumatology* 44(9):1136-1139.

Seldin, M.F. et al. (Jan. 1, 2009). "Shared Susceptibility Variations in Autoimmune Diseases: A Brief Perspective on Common Issues," *Genes and Immunity* 10(1):1-4.

Sobkowiak, A. et al. (Dec. 10, 2008). "Genetic Variation in the Interleukin-10 Gene Promoter in Polish Patients With Systemic Lupus Erythematosus," *Rheumatology International* 29(8):921-925.

Vinusea, C.G. et al. (Jan. 13, 2009). "Logic and Extent of miRNA-Mediated Control of Autoimmune Gene Expression," *International Reviews of Immunology* 28(3-4):112-138.

Wong, C.K. et al. (Jun. 1, 2008). "Hyperproduction of IL-23 and IL-17 in Patients With Systemic Lupus Erythematosus: Implications for Th17-Mediated Inflammation in Auto-Immunity," *Clinical Immunology* 127(3):385-393.

Extended European Search Report dated Dec. 13, 2017, for European Patent Application No. 17158497.2, filed on Oct. 6, 2010, 42 pages.

Guo, L. et al. (2009, e-pub. Apr. 2, 2009). "Replication of the BANK1 Genetic Association With Systemic Lupus Erythematosous in a European-Derived Population," *Genes and Immunity* 10:531-538.

Wain, H.M. et al. (Apr. 2002). "Guidelines for Human Gene Nomenclature," *Genomics* 79(4):464-470.

Zeggini et al. (2008). "Meta-Analysis of Genome-Wide Association Data and Large-Scale Replication Identifies Additional Susceptibility Loci for Type 2 Diabetes," *Nat. Genet.* 40(5):638-645.

rs922483:

CTCTGATCGCAGACCGGGGGTGCTGC[C/T]ACCTCTGTCTGCT
GCCGGCAGAAAG (SEQ ID NO: 13)

SEQUENCE LISTING

<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccacctctct tccgcctttc tcat                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttcatggct tgtggctttc tgcc                                            24

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatccaagac tatgaagaga aagagagag cccac                                 35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgggctctc tcttctctct tcatagtctt ggatc                                35

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccagacacca ctcacccctc tagatgttgg gat                                  33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcccaacat ctagaggggt gagtggtgtc tgg                                  33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccagacacca ctcaccgctc tagatgttgg gat                                    33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atcccaacat ctagagcggt gagtggtgtc tgg                                    33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccagacacca ctcaccactc tagatgttgg gat                                    33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atcccaacat ctagagtggt gagtggtgtc tgg                                    33

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgggggtgct gctacctctg tctgc                                             25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcagacagag gtagcagcac ccccg                                             25

```
<210> SEQ ID NO 13
<211> LENGTH: 52
<212> TYPE: DNA
<213> ORGANISM: Homo sapiens

<400> SEQUENCE: 13
ctctgatcgc agaccggggg tgctgcyacc tctgtctgct gccggcagaa ag          52

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgtgtgtgt gtgtgtgtgt gtgtgtgtgt gtgtgt                             36

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtgtgtgtgt gtgtgtgtgt gtgtgtgtgt gtgtgtgtgt gtgt                    44
```

METHODS FOR TREATING, DIAGNOSING, AND MONITORING LUPUS

CROSS REFERENCE TO RELATED APPLICATIONS

This application is a continuation of co-pending U.S. application Ser. No. 13/501,448, which is a U.S. National Phase Application under 35 U.S.C. § 371 based on International Application PCT/US2010/051589 filed Oct. 6, 2010, which claims the benefit under 35 U.S.C. § 119(e) of priority provisional U.S. Application No. 61/278,510 filed Oct. 7, 2009, all of which are hereby incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 146392016801SeqList.txt, date recorded: Feb. 8, 2016, size: 4 KB).

FIELD

Methods of identifying, diagnosing, prognosing, and assessing risk of developing lupus are provided, as well as methods of treating lupus. Also provided are methods for identifying effective lupus therapeutic agents and predicting responsiveness to lupus therapeutic agents.

BACKGROUND

Lupus is an autoimmune disease that is estimated to affect nearly 1 million Americans, primarily women between the ages of 20-40. Lupus involves antibodies that attack connective tissue. The principal form of lupus is a systemic one (systemic lupus erythematosus; SLE). SLE is a chronic autoimmune disease with strong genetic as well as environmental components (See, e.g., Hochberg M C, Dubois' Lupus Erythematosus. 5th ed., Wallace D J, Hahn B H, eds. Baltimore: Williams and Wilkins (1997); Wakeland E K, et al., Immunity 2001; 15(3):397-408; Nath S K, et al., Curr. Opin. Immunol. 2004; 16(6):794-800; D'Cruz et al., Lancet (2007), 369:587-596). Various additional forms of lupus are known, including, but not limited to, cutaneous lupus erythematosus (CLE), lupus nephritis (LN), and neonatal lupus.

Untreated lupus can be fatal as it progresses from attack of skin and joints to internal organs, including lung, heart, and kidneys (with renal disease being the primary concern), thus making early and accurate diagnosis of and/or assessment of risk of developing lupus particularly critical. Lupus mainly appears as a series of flare-ups, with intervening periods of little or no disease manifestation. Kidney damage, measured by the amount of proteinuria in the urine, is one of the most acute areas of damage associated with pathogenicity in SLE, and accounts for at least 50% of the mortality and morbidity of the disease.

Clinically, SLE is a heterogeneous disorder characterized by high-affinity autoantibodies (autoAbs). AutoAbs play an important role in the pathogenesis of SLE, and the diverse clinical manifestations of the disease are due to the deposition of antibody-containing immune complexes in blood vessels leading to inflammation in the kidney, brain and skin. AutoAbs also have direct pathogenic effects contributing to hemolytic anemia and thrombocytopenia. SLE is associated with the production of antinuclear antibodies, circulating immune complexes, and activation of the complement system. SLE has an incidence of about 1 in 700 women between the ages of 20 and 60. SLE can affect any organ system and can cause severe tissue damage. Numerous autoAbs of differing specificity are present in SLE. SLE patients often produce autoAbs having anti-DNA, anti-Ro, and anti-platelet specificity and that are capable of initiating clinical features of the disease, such as glomerulonephritis, arthritis, serositis, complete heart block in newborns, and hematologic abnormalities. These autoAbs are also possibly related to central nervous system disturbances. Arbuckle et al. described the development of autoAbs before the clinical onset of SLE (Arbuckle et al, N. Engl. J. Med. 349(16): 1526-1533 (2003)). Definitive diagnosis of lupus, including SLE, is not easy, resulting in clinicians resorting to a multi-factorial signs and symptoms-based classification approach (Gill et al., American Family Physician 68(11): 2179-2186(2003)).

One of the most difficult challenges in clinical management of complex autoimmune diseases such as lupus is the accurate and early identification of the disease in a patient. Over the years, many linkage and candidate gene studies have been performed to identify genetic factors contributing to SLE susceptibility. Haplotypes carrying the HLA Class II alleles DRB1*0301 and DRB1*1501 are clearly associated with disease as well as the presence of antibodies to nuclear autoantigens. See, e.g., Goldberg M A, et al., Arthritis Rheum. 19(2):129-32 (1976); Graham R R, et al., Am J Hum Genet. 71(3):543-53 (2002); and Graham R R, et al., Eur J Hum Genet. 15(8):823-30 (2007). More recently, variants of Interferon Regulatory Factor 5 (IRF5) and Signal Transducer and Activator of Transcription 4 (STAT4) were discovered to be significant risk factors for SLE. See, e.g., Sigurdsson S, et al., Am J Hum Genet. 76(3):528-37 (2005); Graham R R, et al., Nat Genet. 38(5):550-55 (2006); Graham R R, et al., Proc Natl Acad Sci USA 104(16):6758-63 (2007); and Remmers E F, et al., N Engl J Med. 357(10): 977-86 (2007). The identification of IRF5 and STAT4 as SLE risk genes provides support for the concept that, in certain instances, the type I interferon (IFN) pathway plays an important role in SLE disease pathogenesis. Type I IFN is present in serum of SLE cases, and production of IFN is linked to the presence of Ab and nucleic acid containing immune complexes reviewed in Ronnblom et al., J Exp Med 194:F59 (2001); see also Baechler E C, et al., Curr Opin Immunol. 16(6):801-07 (2004); Banchereau J, et al., Immunity 25(3):383-92 (2006); Miyagi et al., J Exp Med 204(10): 2383-96 (2007)). The majority of SLE cases exhibit a prominent type I IFN gene expression 'signature' in blood cells (Baechler et al., Proc Natl Acad Sci USA 100:2610 (2003); Bennett et al., J Exp Med 197:711 (2003)) and have elevated levels of IFN-inducible cytokines and chemokines in serum (Bauer et al., PLoS Med 3:e491 (2006)). Immune complexes containing native DNA and RNA stimulate toll-like receptors (TLRs) 7 and 9 expressed by dendritic cells and B cells to produce type interferon which further stimulates immune complex formation (reviewed in (Marshak-Rothstein et al., Annu Rev Immunol 25, 419 (2007)).

In addition, a number of studies have been performed to identify reliable biomarkers for diagnostic and prognostic purposes. No clinically validated diagnostic markers, however, e.g., biomarkers, have been identified that enable clinicians or others to accurately define pathophysiological aspects of SLE, clinical activity, response to therapy, prognosis, or risk of developing the disease, although a number of candidate genes and alleles (variants) have been identified that are thought to contribute to SLE susceptibility. For example, at least 13 common alleles that contribute risk for SLE in individuals of European ancestry have been reported (Kyogoku et al., Am J Hum Genet 75(3):504-7 (2004); Sigurdsson et al., Am J Hum Genet 76(3):528-37 (2005); Graham et al., Nat Genet 38(5):550-55 (2006); Graham et al., Proc Natl Acad Sci USA 104(16):6758-63 (2007); Remmers et al., N Engl J Med 357(10):977-86 (2007); Cunninghame Graham et al., Nat Genet 40(1):83-89 (2008); Harley et al., Nat Genet 40(2):204-10 (2008); Horn et al., N Engl J Med 358(9):900-9 (2008); Kozyrev et al., Nat Genet 40(2): 211-6 (2008); Nath et al., Nat Genet 40(2):152-4 (2008); Sawalha et al., PLoS ONE 3(3):e1727 (2008)). The putative causal alleles are known for HLA-DR3, HLA-DR2, FCGR2A, PTPN22, ITGAM and BANK1 (Kyogoku et al., Am J Hum Genet 75(3):504-7 (2004); Kozyrev et al., Nat Genet 40(2):211-6 (2008); Nath et al., Nat Genet 40(2): 152-4 (2008)), white the risk haplotypes for IRF5, TATSF 4 and BLK likely contribute to SLE by influencing mRNA and protein expression levels (Sigurdsson et al., Am J Hum Genet 76(3):528-37 (2005); Graham et al., Nat Genet 38(5): 550-55 (2006); Graham et al., Proc Natl Acad Sci USA 104(16):6758-63 (2007); Cunninghame Graham et al., Nat Genet 40(1):83-89 (2008); Horn et al., N Engl J Med 358(9):900-9 (2008)). The causal alleles for STAT4, KIAA1542, IRAK1, PXK and other genes, such as BLK, have not been determined (Remmers et al., N Engl J Med 357(10):977-86 (2007); Harley et al., Nat Genet 40(2):204-1.0 (2008); Hom et al., N Engl J Med 358(9000-9 (2008); Sawalha et al., PLoS ONE 3(3):e1727 (2008)). These and other genetic variations associated with lupus are also described in Int'l Pat. Appl. No. PCT/US2008/064430 (Int'l Pub. No. WO 2008/144761). While the contribution of such genetic variation to various aspects of SLE risk and disease that has been described to date has been important, more information about the contribution of genetic variation to, for example, the significant clinical heterogeneity of SLE remains to be determined.

It would therefore be highly advantageous to have additional molecular-based diagnostic methods that can be used to objectively identify the presence of and/or classify the disease in a patient, define pathophysiologic aspects of lupus, clinical activity, response to therapy, prognosis, and/or risk of developing lupus. In addition, it would be advantageous to have molecular-based diagnostic markers associated with various clinical and/or pathophysiological and/or other biological indicators of disease. Thus, there is a continuing need to identify new risk loci and polymorphisms associated with lupus as well as other autoimmune disorders. Such associations would greatly benefit the identification of the presence of lupus in patients or the determination of susceptibility to develop the disease. Such associations would also benefit the identification of pathophysiologic aspects of lupus, clinical activity, response to therapy, or prognosis. In addition, statistically and biologically significant and reproducible information regarding such associations could be utilized as an integral component in efforts to identify specific subsets of patients who would be expected to significantly benefit from treatment with a particular therapeutic agent, for example where the therapeutic agent is or has been shown in clinical studies to be of therapeutic benefit in such specific lupus patient subpopulation.

The invention described herein meets above-described needs and provides other benefits.

All references cited herein, including patent applications and publications, are incorporated by reference in their entirety for any purpose.

SUMMARY

The methods provided are based, at least in part, on the discovery of a set of novel loci that are associated with SLE and that contribute disease risk (SLE risk loci). In addition, a set of alleles associated with these SLE risk loci are provided. Also included is the causal allele within the BLK locus that is associated with biological effects that increase SLE risk. In addition, risk loci associated with other autoimmune diseases and increased SLE risk are provided.

In one aspect, a method of identifying lupus in a subject is provided, the method comprising detecting in a biological sample derived from the subject the presence of a variation in a SLE risk locus, wherein the SLE risk locus is BLK, wherein the variation in the BLK locus occurs at a nucleotide position corresponding to the position of a single nucleotide polymorphism (SNP), wherein the SNP is rs922483 (SEQ ID NO: 13), wherein the variation is thymine at chromosomal location 11389322 on human chromosome 8, and wherein the subject is suspected of suffering from lupus. In one embodiment, the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

In another aspect, a method of identifying lupus in a subject is provided, the method comprising detecting in a biological sample derived from the subject the presence of a variation in at least one SLE risk locus as set forth in Table 4, wherein the variation in the at least one locus occurs at a nucleotide position corresponding to the position of a SNP for the at least one locus as set forth in Table 4, and wherein the subject is suspected of suffering from lupus. In certain embodiments, a variation is detected in at least two loci, or at least three loci, or at least four loci, or at least five loci, or at least ten loci, or at least 13 loci, or at 26 loci. In one embodiment, the at least one locus is selected from TNIP1, PRDM1 JAZF1, UHRF1BP1, and IL10. In one embodiment, the variation in the at least one locus comprises a SNP as set forth in Table 4. In certain embodiments, the presence of a variation in at least one SLE risk locus as set forth in Table 4, wherein the variation in the at least one locus occurs at a nucleotide position corresponding to the position of a SNP for the at least one locus as set forth in Table 4, is detected in combination with the presence of a variation in the BLK SLE risk locus, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8. In one embodiment, the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

In still another aspect, a method of identifying lupus in a subject is provided, the method comprising detecting in a biological sample derived from the subject the presence of a variation in at least one SLE risk locus as set forth in Table 6, wherein the variation in the at least one locus occurs at a nucleotide position corresponding to the position of a SNP for the at least one locus as set forth in Table 6, and wherein the subject is suspected of suffering from lupus. In certain embodiments, a variation is detected in at least two loci, or at least three loci, or at least four loci, or at five loci. In one embodiment, the at least one locus is selected from IFIH1, CFB, CLEC16A, 1L12B, and SH2B3. In one embodiment, the variation in the at least one locus comprises a SNP as set forth in Table 6. In certain embodiments, the presence of a variation in at least one SLE risk locus as set forth in Table 6, wherein the variation in the at least one locus occurs at a nucleotide position corresponding to the position of a SNP for the at least one locus as set forth in Table 6, is detected in combination with the presence of a variation in the BLK SLE risk locus, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8. In one embodiment, the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

In yet another aspect, a method of identifying lupus in a subject is provided, the method comprising detecting in a biological sample derived from the subject the presence of a variation in at least one SLE risk locus as set forth in Table 4 and the presence of a variation in at least one SLE risk locus as set forth in Table 6, wherein the variation in each locus occurs at a nucleotide position corresponding to the position of a SNP for each locus as set forth in Tables 4 and 6, respectively, and wherein the subject is suspected of suffering from lupus. In certain embodiments, a variation is detected in at least three loci, or at least four loci, or at least five loci, or at least seven loci, or at least ten loci. In one embodiment, the at least one locus as set forth in Table 4 is selected from TNIP1, PRDM1, JAZF1, UHRF1BP1, and IL10 and the at least one locus as set forth in Table 6 is selected from IFIH1, CFB, CLEC16A, IL12B, and SH2B3. In one embodiment, the variation in the at least one locus as set forth in Table 4 and the variation in the at least one locus as set forth in Table 6 comprises a SNP as set forth in Tables 4 and 6, respectively. In certain embodiments, the presence of a variation in at least one SLE risk locus as set forth in Table 4, wherein the variation in the at least one locus occurs at a nucleotide position corresponding to the position of a SNP for the at least one locus as set forth in Table 4, and the presence of a variation in at least one SLE risk locus as set forth in Table 6, wherein the variation in the at least one locus occurs at a nucleotide position corresponding to the position of a SNP for the at least one locus as set forth in Table 6, is detected in combination with the presence of a variation in the BLK SLE risk locus, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8. In one embodiment, the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

In one aspect, a method for predicting responsiveness of a subject with lupus to a lupus therapeutic agent is provided, the method comprising determining whether the subject comprises a variation in a SLE risk locus, wherein the SLE risk locus is BLK, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 82, wherein the presence of the variation in the BLK SLE risk locus indicates the responsiveness of the subject to the therapeutic agent.

In another aspect, a method for predicting responsiveness of a subject with lupus to a lupus therapeutic agent is provided, the method comprising determining whether the subject comprises a variation in at least one SLE risk locus as set forth in Table 4, wherein the variation in the at least one locus occurs at a nucleotide position corresponding to the position of a SNP for the at least one locus as set forth in Table 4, wherein the presence of a variation in the at least one locus indicates the responsiveness of the subject to the therapeutic agent. In certain embodiments, the subject comprises a variation in at least two loci, or at least three loci, or at least four loci, or at least five loci, or at least ten loci, or at least 13 loci, or at 26 loci. In one embodiment, the at least one locus is selected from TNIP1, PRDM1, JAZF1, UHRF1BP1, and IL10. In one embodiment, the variation in the at least one locus comprises a SNP as set forth in Table 4. In certain embodiments, the method comprises determining whether the subject comprises a variation in at least one SLE risk locus as set forth in Table 4, wherein the variation in the at least one locus occurs at a nucleotide position corresponding to the position of a SNP for the at least one locus as set forth in Table 4, in combination with a variation in the BLK SLE risk locus, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, wherein the presence of a variation in the at least one locus as set forth in Table 4 and the presence of the variation in the BLK locus indicates the responsiveness of the subject to the therapeutic agent.

In still another aspect, a method for predicting responsiveness of a subject with lupus to a lupus therapeutic agent is provided, the method comprising determining whether the subject comprises a variation in at least one SLE risk locus as set forth in Table 6, wherein the variation in the at least one locus occurs at a nucleotide position corresponding to the position of a SNP for the at least one locus as set forth in Table 6, wherein the presence of a variation in the at least one locus indicates the responsiveness of the subject to the therapeutic agent. In certain embodiments, the subject comprises a variation in at least two loci, or at least three loci, or at least four loci, or at five loci. In one embodiment, the at least one locus is selected from IFIH1, CFB, CLEC16A, IL12B, and SH2B3. In one embodiment, the variation in the at least one locus comprises a SNP as set forth in Table 6. In certain embodiments, the method comprises determining whether the subject comprises a variation in at least SLE risk locus as set forth in Table 6, wherein the variation in the at least one locus occurs at a nucleotide position corresponding to the position of a SNP for the at least one locus as set forth in Table 6, in combination with a variation in the BLK SLE risk locus, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, wherein the presence of a variation in the at least one locus as set forth in Table 6 and the presence of the variation in the BLK locus indicates the responsiveness of the subject to the therapeutic agent.

In a further aspect, a method for predicting responsiveness of a subject with lupus to a lupus therapeutic agent is provided, the method comprising determining whether the subject comprises a variation bout least one SLE risk locus as set forth in Table 4, wherein the variation in the at least one locus occurs at a nucleotide position corresponding to the position of a SNP for the at least one locus as set forth in Table 4, and a variation in at least one SLE risk locus as set forth in Table 6, wherein the variation in the at least one locus occurs at a nucleotide position corresponding to the position of a SNP for the at least one locus as set forth in Table 6, wherein the presence of a variation in the at least one locus as set forth in Table 4 and the presence of a variation in the at least one locus as set forth in Table 6 indicates the responsiveness of the subject to the therapeutic agent. In certain embodiments, the subject comprises a variation in at least three loci, or at least four loci, or at least five loci, or at least seven loci, or at least ten loci. In one embodiment, the at least one locus as set forth in Table 4 is selected from TNIP1, PRDM1, JAZF1, UHRF1BP1, and IL10 and the at least one locus as set forth in Table 6 is selected from IFIH1, CFB, CLEC16A, IL12B, and SH2B3. In one embodiment, the variation in the at least one locus as set forth in Table 4 and the at least one locus as set forth in Table 6 comprises a SNP as set forth in Tables 4 and 6, respectively. In certain embodiments, the method comprises determining whether the subject comprises a variation in at least one SLE risk locus as set forth in Table 4, wherein the variation in the at least one locus occurs at a nucleotide position corresponding to the position of a SNP for the at least one locus as set forth in Table 4, and a variation in at least one SLE risk locus as set forth in Table 6, wherein the variation in the at least one locus occurs at a nucleotide position corresponding to the position of a SNP the at least one locus as set forth in Table 6, in combination with a variation in the BLK SLE risk locus, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, wherein the presence of a variation in the at least one locus as set forth in Table 4 and the presence of a variation in the at least one locus as set forth in Table 6 and the presence of the variation in the BLK locus indicates the responsiveness of the subject to the therapeutic agent.

In yet another aspect, a method of diagnosing or prognosing lupus in a subject is provided, the method comprising detecting in a biological sample derived from the subject the presence of a variation in a SLE risk locus, wherein the SLE risk locus is BLK, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, and the presence of the variation in the BLK locus is a diagnosis or prognosis of lupus in the subject.

In yet a further aspect, a method of diagnosing or prognosing lupus in a subject is provided, the method comprising detecting in a biological sample derived from the subject the presence of a variation in at least one SLE, risk locus as set forth in Table 4, wherein: the biological sample is known to comprise, or suspected of comprising, nucleic acid comprising a variation in at least one SLE risk locus as set forth in Table 4; the variation in the at least one locus comprises, or is located at a nucleotide position corresponding to, a SNP as set forth in Table 4; and the presence of the variation in the at least one locus is a diagnosis or prognosis of lupus in the subject. In certain embodiments, a variation is detected in at least two loci, or at least three loci, or at least four loci, or at least five loci, or at least ten loci, or at least 13 loci, or at 26 loci. In one embodiment, the at least one SLE risk locus is selected from TNIP1, PRDM1, JAZF1, UHRF1BP1, and IL10. In certain embodiments, the method comprises detecting the presence of a variation in at least one SLE risk locus as set forth in Table 4 in combination with the presence of a variation in the BLK SLE risk locus, wherein: the biological sample is known to comprise, or suspected of comprising, nucleic acid comprising a variation in at least one SLE risk locus as set forth in Table 4 and a variation in the BLK locus, the variation in the at least one locus as set forth in Table 4 comprises, or is located at a nucleotide position corresponding to, a SNP as set forth in Table 4, and the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, and the presence of the variation in the at least one locus as set forth in Table 4 and the presence of the variation in the BLK locus is a diagnosis or prognosis of lupus in the subject.

In a still further aspect, a method of diagnosing or prognosing lupus in a subject is provided, the method comprising detecting in a biological sample derived from the subject the presence of a variation in at least one SLE risk locus as set forth in Table 6, wherein: the biological sample is known to comprise, or suspected of comprising, nucleic acid comprising a variation in at least one SLE risk locus as set forth in Table 6; the variation in the at least one locus comprises, or is located at a nucleotide position corresponding to, a SNP as set forth in Table 6; and the presence of the variation in the at least one locus is a diagnosis or prognosis of lupus in the subject. In certain embodiments, a variation is detected in at least two loci, or at least three loci, or at least four loci, or at five loci. In one embodiment, the at least one SLE risk locus is selected from IFIH1, CFB, CLEC16A, IL12B, and SH2B3. In certain embodiments, the method comprises detecting the presence of a variation in at least one SLE risk locus as set forth in Table 6 in combination with the presence of a variation in the BLK SLE risk locus, wherein: the biological sample is known to comprise, or suspected of comprising, nucleic acid comprising a variation in at least one SLE risk locus as set forth in Table 6 and a variation in the BLK locus, the variation in the at least one locus as out forth in Table 6 comprises, or is located at a nucleotide position corresponding to, a SNP as set forth in Table 6, and the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, and the presence of the variation in the at least one locus as set forth in Table 6 and the presence of the variation in the BLK locus is a diagnosis or prognosis of lupus in the subject.

In yet another aspect, a method of diagnosing or prognosing lupus in a subject is provided, the method comprising detecting in a biological sample derived from the subject the presence of a variation in at feast one SLE risk locus as set forth in Table 4 and the presence of a variation in at least one SLE risk locus as set forth in Table 6, wherein: the biological sample is known to comprise, or suspected of comprising, nucleic acid comprising a variation in at least one SLE risk locus as set forth in Table 4 and a variation in at least one SLE risk locus as set forth in Table 6; the variation in the at least one locus comprises, or is located at a nucleotide position corresponding to, a SNP as set forth in Tables 4 and 6, respectively; and the presence of the variation in the at least one locus as set forth in Table 4 and the presence of the variation in the at least one locus as set forth in Table 6 is a diagnosis or prognosis of lupus in the subject. In certain embodiments, a variation is detected in at least three loci, or at least four loci, or at least five loci, or at least seven loci, or at least ten loci. In one embodiment, the at least one SLE risk locus as set forth in Table 4 is selected from TNIP1, PRDM1 JAZF1, UHRF1BP1, and IL10 and the at least one SLE risk locus as set forth in Table 6 is selected from IFIH1, CFB, CLEC16A, IL12B, and SH2B3. In certain embodiments, the method comprises detecting the presence of a variation in at least one SLE risk locus as set forth in Table 4 and the presence of a variation in at least one SLE risk locus as set forth in Table 6 in combination with the presence of a variation in the BLK SLE risk locus, wherein: the biological sample is known to comprise, or suspected of comprising, nucleic acid comprising a variation in at least one SLE risk locus as set forth in Table 4 and variation in at least SLE risk locus as set forth in Table) and a variation in the BLK locus, the variation in the at least one locus as set forth in Table 4 comprises, or is located at a nucleotide position corresponding to, a SNP as set forth in Table 4, and the variation in the at least one locus as set forth in Table 6 comprises, or is located at a nucleotide position corresponding to, a SNP as set forth in Table 6, and the variation in the BLK locus occurs at a nucleotide position corresponding to the position of a SNP, wherein the SNP is rs922483 (SEQ. ID NO: 13), wherein the variation is thymine at chromosomal location 11389322 on human chromosome 8, and the presence of the variation in the at least one locus as set forth in Table 4 and the presence of the variation in the at least one locus as set forth in Table 6 and the presence of the variation in the BLK locus is a diagnosis or prognosis of lupus in the subject.

In another aspect, a method of aiding in the diagnosis or prognosis of lupus in a subject is provided, the method comprising detecting in a biological sample derived from the subject the presence of a variation in a SLE risk locus, wherein the SLE risk locus is BLK, wherein the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, and the presence of the variation in the BLK locus is a diagnosis or prognosis of lupus in the subject.

In yet another aspect, a method of aiding in the diagnosis or prognosis of lupus in a subject is provided, the method comprising detecting in a biological sample derived from the subject the presence of a variation in at least one SLE risk locus as set forth in Table 4, wherein: the biological sample is known to comprise, or suspected of comprising, nucleic acid comprising a variation in at least one SLE risk locus as set forth in Table 4; the variation in the at least one locus comprises, or is located at a nucleotide position corresponding to, a SNP as set forth in Table 4; and the presence of the variation in the at least one locus is a diagnosis or prognosis of lupus in the subject. In certain embodiments, a variation is detected in at least two loci, or at least three loci, or at least four loci, or at least five loci, or at least ten loci, or at least 13 loci, or at 26 loci. In one embodiment, the at least one SLE risk locus is selected from TNIP1, PRDM1, JAZF1, UHRF1BP1, and IL10. In certain embodiments, the method comprises detecting the presence of a variation in at least one SLE risk locus as set forth in Table 4 in combination with the presence of a variation in the BLK SLE risk locus, wherein: the biological sample is known to comprise, or suspected of comprising, nucleic acid comprising a variation in at least one SLE risk locus as set forth in Table 4 and a variation in the BLK locus, the variation in the at least one locus as set forth in Table 4 comprises, or is located at a nucleotide position corresponding to, a SNP as set forth in Table 4, and the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, and the presence of the variation in the at least one locus as set forth in Table 4 and the presence of the variation in the BLK locus is a diagnosis or prognosis of lupus in the subject.

In a still further aspect, a method of aiding in the diagnosis or prognosis of lupus in a subject is provided, the method comprising detecting in a biological sample derived from the subject the presence of a variation in at least one SLE risk locus as set forth in Table 6, wherein: the biological sample is known to comprise, or suspected of comprising, nucleic acid comprising a variation in at least one SLE risk locus as set forth in Table 6; the variation in the at least one locus comprises, or is located at a nucleotide position corresponding to, a SNP as set forth in Table 6; and the presence of the variation in the at least one locus is a diagnosis or prognosis of lupus in the subject. In certain embodiments, a variation is detected in at least two loci, or at least three loci, or at least four loci, or at five loci. In one embodiment, the at least one SLE risk locus is selected from IFIH1, CFB, CLEC16A, IL12B, and SH2B3. In certain embodiments, the method comprises detecting the presence of a variation in at least one SLE risk locus as set forth in Table 6 in combination with the presence of a variation in the BLK SLE risk locus, wherein: the biological sample is known to comprise, or suspected of comprising, nucleic acid comprising a variation in at least one SLE risk locus as set forth in Table 6 and a variation in the BLK locus, the variation in the at least one locus as set forth in Table 6 comprises, or is located at a nucleotide position corresponding to, a SNP as set forth in Table 6, and the variation in the BLK locus occurs at a nucleotide position corresponding to the position of a. SNP, wherein the SNP is rs922483 (SEQ ID NO: 13), wherein the variation is thymine at chromosomal location 11389322 on human chromosome 8, and the presence of the variation in the at least one locus as set forth in Table 6 and the presence of the variation in the BLK locus is a diagnosis or prognosis of lupus in the subject.

In yet a further aspect, a method of aiding in the diagnosis or prognosis of lupus in a subject is provided, the method comprising detecting in a biological sample derived from the subject the presence of a variation in at least one SLE risk locus as set forth in Table 4 and the presence of a variation in at least one SLE risk locus as set forth in Table 6, wherein: the biological sample is known to comprise, or suspected of comprising, nucleic acid comprising a variation in at least one SLE risk locus as set forth in Table 4 and a variation in at least one SLE risk locus as set forth in Table 6; the variation in the at least one locus comprises, or is located at a nucleotide position corresponding to, a SNP as set forth in Tables 4 and 6, respectively; and the presence of the variation in the at least one locus as set forth in Table 4 and the presence of the variation in the at least one locus as set forth in Table 6 is a diagnosis or prognosis of lupus in the subject. In certain embodiments, a variation is detected in at least three loci, or at least four loci, or at least five loci, or at least seven loci, or at least ten loci. In one embodiment, the at least one SLE risk locus as set forth in Table 4 is selected from TNIP1, PRDM1, JAZF1, UHRF1, BP1, and IL10 and the at least one SLE risk locus as set forth in Table 6 is selected from IFIH1, CFB, CLEC16A, IL12B, and SH2B3. In certain embodiments, the method comprises detecting the presence of a variation in at least one SLE risk locus as set forth in Table 4 and the presence of a variation in at least one SLE risk locus as set forth in Table 6 in combination with the presence of a variation in the BLK SLE risk locus, wherein: the biological sample is known to comprise, or suspected of comprising, nucleic acid comprising a variation in at least one SLE risk locus as set forth in Table 4 and variation in at least SLE risk locus as set forth in Table 6 and a variation in the BLK locus, the variation in the at least one locus as set forth in Table 4 comprises, or is located at a nucleotide position corresponding to, a SNP as set forth in Table 4, and the variation in the at least one locus as set forth in Table 6 comprises, or is located at a nucleotide position corresponding to, a SNP as set forth in Table 6, and the variation in the BLK locus occurs at a nucleotide position corresponding to the position of a SNP, wherein the SNP is rs922483 (SEQ ID NO: 13), wherein the variation is thymine at chromosomal location 11389322 on human chromosome 8, and the presence of the variation in the at least one locus as set forth in Table 4 and the presence of the variation in the at least one locus as set forth in Table 6 and the presence of the variation in the BLK locus is a diagnosis or prognosis of lupus in the subject.

In one aspect, a method of treating a lupus condition in a subject is provided, wherein a genetic variation is known to be present at a nucleotide position corresponding to a SNP in a SLE risk locus, wherein the SNP is rs922483 (SEQ ID NO: 13) and the SLE risk locus is BLK, wherein the variation is thymine at chromosomal location 11389322 on human chromosome 8, the method comprising administering to the subject a therapeutic agent effective to treat the condition.

In another aspect, a method of treating a lupus condition in a subject in whom a genetic variation is known to be present at a nucleotide position corresponding to a SNP as set forth in Table 4 in at least one SLE risk locus as set forth in Table 4 is provided, the method comprising administering to the subject a therapeutic agent effective to treat the condition. In one embodiment, the at least one SLE risk locus is selected from TNIP1, PRDM1, JAZF1, UHRF1BP1, and IL10.

In another aspect, a method of treating a lupus condition in a subject in whom a genetic variation is known to be present at a nucleotide position corresponding to a SNP as set forth in Table 6 in at least one SLE risk locus as set forth in Table 6 is provided, the method comprising administering to the subject a therapeutic agent effective to treat the condition. In one embodiment, the at least one SLE risk locus is selected from IFIH1, CFB, CLEC16A, IL12B, and SH2B30.

In another aspect, a method of treating a subject having a lupus condition is provided, the method comprising administering to the subject a therapeutic agent effective to treat the condition in a subject who has a genetic variation at a nucleotide position corresponding to a SNP in a SLE risk locus, wherein the SNP is rs922483 (SEQ ID NO: 13) and the SLE risk locus is BLK, wherein the variation is thymine at chromosomal location 11389322 on human chromosome 8.

In yet another aspect, a method of treating a subject having a lupus condition is provided, the method comprising administering to the subject a therapeutic agent effective to treat the condition in a subject who has a genetic variation at a nucleotide position corresponding to a SNP as set forth in Table 4 in at least one SLE risk locus as set forth in Table 4. In one embodiment, the at least one SLE risk locus is selected from TNIP1, PRDM1, JAZF1, UHRF1BP1, and IL10.

In still yet another aspect, a method of treating a subject having a lupus condition is provided, the method comprising administering to the subject a therapeutic agent effective to treat the condition in a subject who has a genetic variation at a nucleotide position corresponding to a SNP as set forth in Table 6 in at least one SLE risk locus as set forth in Table 6. In one embodiment, the at least one SLE risk locus is selected from IFIH1, CFB, CLEC16A, IL12B, and SH2B3.

In yet another aspect, a method of treating a subject having a lupus condition is provided, the method comprising administering to the subject a therapeutic agent shown to be effective to treat said condition in at least one clinical study wherein the agent was administered to at least five human subjects who each had a genetic variation at a nucleotide position corresponding to a SNP in a SLE risk locus, wherein the SNP is rs922483 (SEQ ID NO: 13) and the SLE risk locus is BLK, wherein the variation is thymine at chromosomal location 11389322 on human chromosome 8.

In still yet another aspect, a method of treating a subject having a lupus condition is provided, the method comprising administering to the subject a therapeutic agent shown to be effective to treat said condition in at least one clinical study wherein the agent was administered to at least five human subjects who each had a genetic variation at a nucleotide position corresponding to a SNP as set forth in Table 4 in at least one SLE risk locus as set forth in Table 4. In one embodiment, the at least one SLE risk locus is selected from TNIP1, PRDM1, JAZF1, UHRF1BP1, and IL10.

In yet another aspect, a method of treating a subject having a lupus condition is provided, the method comprising administering to the subject a therapeutic agent shown to be effective to treat said condition in at least one clinical study wherein the agent was administered to at least five human subjects who each had a genetic variation at a nucleotide position corresponding to a SNP as set forth in Table 6 in at least one SLE risk locus as set forth in Table 6. In one embodiment, the at least one SLE risk locus is selected from IFIH1, CFB, CLEC16A, IL12B, and SH2B3.

In another aspect, a method comprising manufacturing a lupus therapeutic agent is provided, which includes packaging the agent with instructions to administer the agent to a subject who has or is believed to have lupus and who has a genetic variation at a position corresponding to a SNP in a SLE risk locus, wherein the SNP is rs922483 (SEQ ID NO: 13) and the SLE risk locus is BLK, wherein the variation is thymine at chromosomal location 11389322 on human chromosome 8.

In yet another aspect, a method comprising manufacturing a lupus therapeutic agent is provided, which includes packaging the agent with instructions to administer the agent to a subject who has or is believed to have lupus and who has a genetic variation at a position corresponding to a SNP as set forth in Table 4 in at least one SLE risk locus as set forth in Table 4.

In yet a further aspect, a method comprising manufacturing a lupus therapeutic agent is provided, which includes packaging the agent with instructions to administer the agent to a subject who has or is believed to have lupus and who has a genetic variation at a position corresponding to a SNP as set forth in Table 6 in at least one SLE risk locus as set forth in Table 6.

In one aspect, a method for selecting a patient suffering from lupus for treatment with a lupus therapeutic agent is provided, the method comprising detecting the presence of a genetic variation at a nucleotide position corresponding to a SNP in a SLE risk locus, wherein the SNP is rs922483 (SEQ ID NO: 13) and the SLE risk locus is BLK, wherein the variation is thymine at chromosomal location 11389322 on human chromosome 8. In one embodiment, the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

In a further aspect, a method for selecting a patient suffering from lupus for treatment with a lupus therapeutic agent is provided, the method comprising detecting the presence of a genetic variation at a nucleotide position corresponding to a SNP as set forth in Table 4 in at least one SIT risk locus as set forth in Table 4. In certain embodiments, a variation is detected in at least two loci, or at least three loci, or at least four loci, or at least five loci, or at least ten loci, or at least 13 loci, or at 26 loci. In one embodiment, the at least one SLE risk locus is selected from TNIP1, PRDM1, JAZF1, UHRF1BP1 and IL10. In one embodiment, the variation at the least one locus comprises a SNP as set forth Table 4. In one embodiment, the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

In a further aspect, a method for selecting a patient suffering from lupus for treatment with a lupus therapeutic agent is provided, the method comprising detecting the presence of a genetic variation at a nucleotide position corresponding to a SNP as set forth in Table 6 in at least one SLE risk locus as set forth in Table 6. In certain embodiments, a variation is detected in at least two loci, or at least three loci, or at least four loci, or at five loci. In one embodiment, the at least one SLE risk locus is selected from IFIH1, CFB, CLEC164, IL12B, and SH2B3. In one embodiment, the variation at the least one locus comprises a SNP as set forth Table 6. In one embodiment, the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

In another aspect, a method of assessing whether a subject is at risk of developing lupus is provided, the method comprising detecting in a biological sample obtained from the subject, the presence of a genetic signature indicative of risk of developing lupus, wherein said genetic signature comprises a set of at least three SNPs, each SNP occurring in a SLE risk locus as set forth in Table 4 and/or Table 6. In certain embodiments, the genetic signature comprises a set of at least four SNPs, or at least five SNPs, or at least seven SNPs, or at least ten SNPs. In one embodiment, the SLE risk loci are selected from TNIP1, PRDJM1, JAZF1, UHRF1BP1, IL10, IFIH1, CFB, CLEC16A, IL12B, and SH2B3. In certain embodiments, the genetic signature further comprises a SNP in a SLE risk locus, wherein the SNP is rs922483 (SEQ ID NO: 13) and the SLE risk locus is BLK, wherein the variation is thymine at chromosomal location 11389322 on human chromosome 8.

In a further aspect, a method of diagnosing lupus in a subject is provided, the method comprising detecting in a biological sample obtained from said subject, the presence of a genetic signature indicative of lupus, wherein said genetic signature comprises a set of at least three SNPs, each SNP occurring in a SLE risk locus as set forth in Table 4 and/or Table 6. In certain embodiments, the genetic signature comprises a set of at least four SNPs, or at least five SNPs, or at least seven SNPs, or at least ten SNPs, or at least 15 SNPs, or at least 20 SNPs, or at least 30 SNPs. In one embodiment, the SLE risk loci are selected from TNIP1, PRDM1, JAZF1, UHRF1BP1, IL10, IFIH1, CFB, CLEC16A, IL12B, and SH2B3. In certain embodiments, the genetic signature further comprises a SNP in a SLE risk locus, wherein the SNP is rs922483 (SEQ ID NO: 13) and the SLE risk locus is BLK, wherein the variation is thymine at chromosomal location 11389322 on human chromosome 8.

BRIEF DESCRIPTION OF THE DRAWINGS

(FIG. 2F) A histogram of the P values of independent SNPs in the case and control replication samples as described in Example 1; the expected density of results under a null distribution is indicated by the dashed line.

FIG. 4 discloses 'C>T-rs922483' as SEQ ID NO: 13.

(FIG. 5A) SNP rs922483 C>T (SEQ ID NO: 13) in BJAB cells; (FIG. 5B) SNP rs922483 C>T (SEQ ID NO: 13) in Daudi cells; (FIG. 5C) SNP rs1382568 A>C/G>C in BJAB cells; (FIG. 5D) SNP rs1382568 A>C/G>C in Daudi cells; (FIG. 5E) SNP rs4840568 G>A in BJAB cells; (FIG. 5F) SNP rs4840568 G>A in Daudi cells; data shown represent the mean+/−standard error of the mean in triplicate assays; spotted bars show the results for the haplotype indicated to the left of the graph; hatched bar: risk haplotype 22-ACT; open bar: non-risk haplotype 22-GAC; *$p<0.05$, $p<0.01$, *$p<0.001$, ns=not significant (t-test). FIGS. 5A-F disclose '22 (GT) repeat' as SEQ ID NO: 15. FIGS. 5C-F also disclose 'rs922483 C>T' as SEQ ID NO: 13.

FIG. 6 discloses '18 (GT) repeat' as SEQ ID NO: 14, '22 (GT) repeat' as SEQ ID NO: 15, and 'rs922483 C>T' as SEQ ID NO: 13.

DETAILED DESCRIPTION

Figure 1:
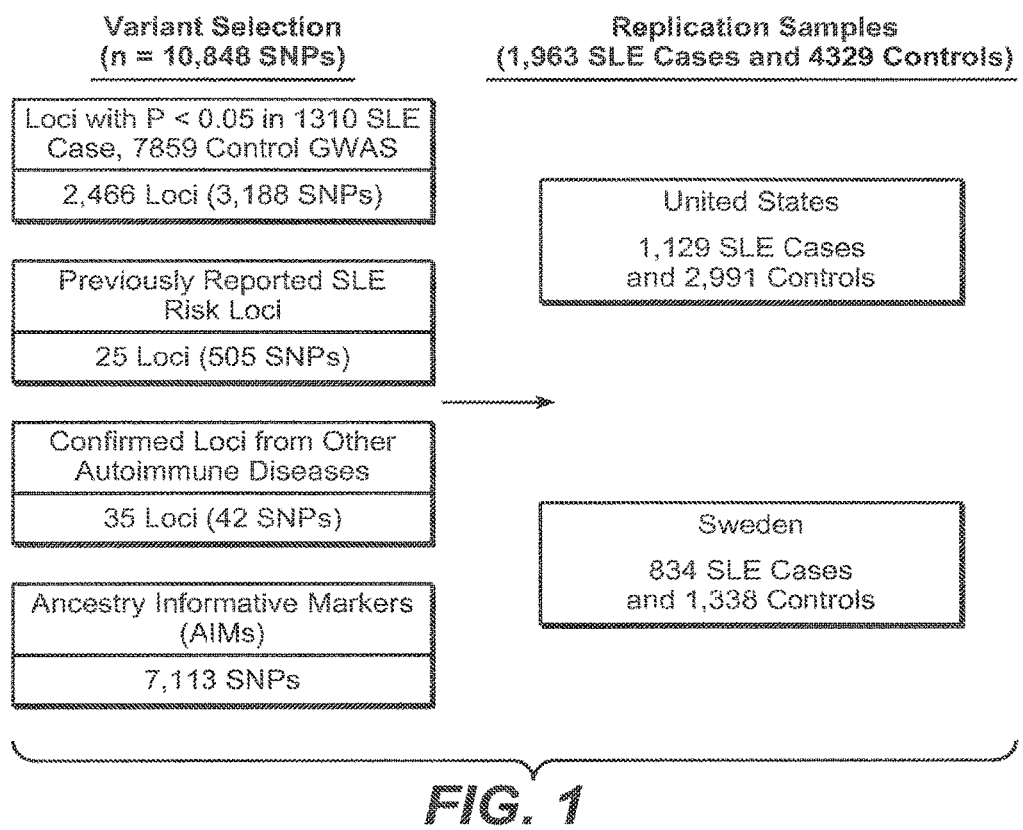
FIG. 1 shows an overview of the experimental design for the targeted replication study of certain SNPs to identify additional SLE risk loci as described in Example 1.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994). In addition, primers, oligonucleotides and polynucleotides employed in the present invention can be generated using standard techniques known in the art.

Unless defined otherwise, technical and scientific terms used herein have the same meaning as commonly understood by one of ordinary skill in the art to which this invention belongs. For example, Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Definitions

For purposes of interpreting this specification, the following definitions will apply and whenever appropriate, terms used in the singular will also include the plural and vice versa. As used in this specification and the appended claims, the singular fibrins "a," "an" and "the" include plural referents unless the context clearly dictates otherwise. Thus, for example, reference to "a protein" includes a plurality of proteins; reference to "a cell" includes mixtures of cells, and the like. In the event that any definition set forth below conflicts with any document incorporated herein by reference, the definition set forth below shall control.

"Lupus" or "lupus condition", as used herein is an autoimmune disease or disorder that in general involves antibodies that attack connective tissue. The principal form of lupus is a systemic one, systemic lupus erythematosus (SLE), including cutaneous SLE and subacute cutaneous SLE, as well as other types of lupus (including nephritis, extrarenal, cerebritis, pediatric, non-renal, discoid, and alopecia).

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptulose, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

The term "primer" refers to a single stranded polynucleotide that is capable of hybridizing to a nucleic acid and allowing the polymerization of a complementary nucleic acid, generally by providing a free 3'OH group.

The term "genetic variation" or "nucleotide variation" refers to a change in a nucleotide sequence (e.g., an insertion, deletion, inversion, or substitution of one or more nucleotides, such as a single nucleotide polymorphism (SNP)) relative to a reference sequence (e.g., a commonly-found and/or wild-type sequence, and/or the sequence of a major allele). The term also encompasses the corresponding change in the complement of the nucleotide sequence, unless otherwise indicated. In one embodiment, a genetic variation is a somatic polymorphism. In one embodiment, a genetic variation is a germline polymorphism.

A "single nucleotide polymorphism", or "SNP", refers to a single base position in DNA at which different alleles, or alternative nucleotides, exist in a population. The SNP position is usually preceded by and followed by highly conserved sequences of the allele (e.g., sequences that vary in less than ¹/₁₀₀ or ¹/₁₀₀₀ members of the populations). An individual may be homozygous or heterozygous for an allele at each SNP position.

The term "amino acid variation" refers to a change in an amino acid sequence (e.g., an insertion, substitution, or deletion of one or more amino acids, such as an internal deletion or an N- or C-terminal truncation) relative to a reference sequence.

The term "variation" refers to either a nucleotide variation or an amino acid variation.

The term "a genetic variation at a nucleotide position corresponding to the position of a SNP," "a nucleotide variation at a nucleotide position corresponding to the position of a SNP," and grammatical variants thereof refer to a nucleotide variation in a polynucleotide sequence at the relative corresponding DNA position occupied by said SNP in the genome. The term also encompasses the corresponding variation in the complement of the nucleotide sequence, unless otherwise indicated.

The term "array" or "microarray" refers to an ordered arrangement of hybridizable array elements, preferably polynucleotide probes e.g., oligonucleotides), on a substrate. The substrate can be a solid substrate, such as a glass slide, or a semi-solid substrate, such as nitrocellulose membrane.

The term "amplification" refers to the process of producing one or more copies of a reference nucleic acid sequence or its complement. Amplification may be linear or exponential (e.g., PCR). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

The term "allele-specific oligonucleotide" refers to an oligonucleotide that hybridizes to a region of a target nucleic acid that comprises a nucleotide variation (generally a substitution). "Allele-specific hybridization" means that, when an allele-specific oligonucleotide is hybridized to its target nucleic acid, a nucleotide in the allele-specific oligonucleotide specifically base pairs with the nucleotide variation. An allele-specific oligonucleotide capable of allele-specific hybridization with respect to a particular nucleotide variation is said to be "specific for" that variation.

The term "allele-specific primer" refers to an allele-specific oligonucleotide that is a primer.

The term "primer extension assay" refers to an assay in which nucleotides are added to a nucleic acid, resulting in a longer nucleic acid, or "extension product," that is detected directly or indirectly. The nucleotides can be added to extend the 5' or 3' end of the nucleic acid.

The term "allele-specific nucleotide incorporation assay" refers to a primer extension assay in which a primer is (a) hybridized to target nucleic acid at a region that is 3' or 5' of a nucleotide variation and (b) extended by a polymerase, thereby incorporating into the extension product a nucleotide that is complementary to the nucleotide variation.

The term "allele-specific primer extension assay" refers to a primer extension assay in which an allele-specific primer is hybridized to a target nucleic acid and extended.

The term "allele-specific oligonucleotide hybridization assay" refers to an assay in which (a) an allele-specific oligonucleotide is hybridized to a target nucleic acid and (b) hybridization is detected directly or indirectly.

The term "5' nuclease assay" refers to an assay which hybridization of an allele-specific oligonucleotide to a target nucleic acid allows for nucleolytic cleavage of the hybridized probe, resulting in a detectable signal.

The term "assay employing molecular beacons" refers to an assay in which hybridization of an allele-specific oligonucleotide to a target nucleic acid results in a level of detectable signal that is higher than the level of detectable signal emitted by the free oligonucleotide.

The term "oligonucleotide ligation assay" refers to an assay in which an allele-specific oligonucleotide and a second oligonucleotide are hybridized adjacent to one another on a target nucleic acid and ligated together (either directly or indirectly through intervening nucleotides), and the ligation product is detected directly or indirectly.

The term "target sequence," "target nucleic acid," or "target nucleic acid sequence" refers generally to a polynucleotide sequence of interest in which a nucleotide variation is suspected or known to reside, including copies of such target nucleic acid generated by amplification.

The term "detection" includes any means of detecting, including direct and indirect detection.

The term "SLE risk locus" and "confirmed SLE risk locus" refer to any one of the loci indicated in Table 4 and Table 6 and the BLK locus.

The term "SLE risk allele" and "confirmed SLE risk allele" refer to a variation occurring in a SLE risk locus. Such variations include, but are not limited to, single nucleotide polymorphisms, insertions, and deletions. Certain exemplary SLE risk alleles are indicated in Table 4 and in Table 6.

As used herein, a subject "at risk" of developing lupus may or may not have detectable disease or symptoms of disease, and may or may not have displayed detectable disease or symptoms of disease prior to the treatment methods described herein. "At risk" denotes that a subject has one or more risk factors, which are measurable parameters that correlate with development of lupus, as described herein and known in the art. A subject having one or more of these risk factors has a higher probability of developing lupus than a subject without one or more of these risk factor(s).

The term "diagnosis" is used herein to refer to the identification or classification of a molecular or pathological state, disease or condition. For example, "diagnosis" may refer to identification of a particular type of lupus condition, e.g., SLE. "Diagnosis" may also refer to the classification of a particular sub-type of lupus, e.g., by tissue/organ involvement (e.g., lupus nephritis), by molecular features (e.g., a patient subpopulation characterized by genetic variation(s) in a particular gene or nucleic acid region.)

The term "aiding diagnosis" is used herein to refer to methods that assist in making a clinical determination regarding the presence, or nature, of a particular type of symptom or condition of lupus. For example, a method of aiding diagnosis of lupus can comprise measuring the presence of absence of one or more SLE risk loci or SLE risk alleles in a biological sample from an individual.

The term "prognosis" is used herein to refer to the prediction of the likelihood of autoimmune disorder-attributable disease symptoms, including, for example, recurrence, flaring, and drug resistance, of an autoimmune disease such as lupus. The term "prediction" is used herein to refer to the likelihood that a patient will respond either favorably or unfavorably to a drug or set of drugs.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically affective amount will be less than the therapeutically effective amount.

An "individual," "subject" or "patient" is a vertebrate. In certain embodiments, the vertebrate is a mammal. Mammals include, but are not limited to, primates (including human and non-human primates) and rodents (e.g., mice and rats). In certain embodiments, a mammal is a human.

A "patient subpopulation," and grammatical variations thereof, as used herein, refers to a patient subset characterized as having one or more distinctive measurable and/or identifiable characteristics that distinguishes the patient subset from others in the broader disease category to which it belongs. Such characteristics include disease subcategories (e.g., SLE, lupus nephritis), gender, lifestyle, health history, organs/tissues involved, treatment history, etc.

A "control subject" refers to a healthy subject who has not been diagnosed as having lupus or a lupus condition and who does not suffer from any sign or symptom associated with lupus or a lupus condition.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrases "biological sample" or "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like. A "reference sample", "reference cell", "reference tissue", "control sample", "control cell", or "control tissue", as used herein, refers to a sample, cell or tissue obtained from a source known, or believed, not to be afflicted with the disease or condition for which a method or composition of the invention is being used to identify. In one embodiment, a reference sample, reference cell, reference tissue, control sample, control cell, or control tissue is obtained from a healthy part of the body of the same subject or patient in whom a disease or condition is being identified using a composition or method of the invention. In one embodiment, a reference sample, reference cell, reference tissue, control sample, control cell, or control tissue is obtained from a healthy part of the body of an individual who is not the subject or patient in whom a disease or condition is being identified using a composition or method of the invention.

For the purposes herein a "section" of a tissue sample is meant a single part or piece of a tissue sample, e.g. a thin slice of tissue or cells cut from a tissue sample. It is understood that multiple sections of (issue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

A "medicament" is an active drug to treat a disease, disorder, and/or condition. In one embodiment, the disease, disorder, and/or condition is lupus or its symptoms or side effects.

The term "increased resistance" to a particular therapeutic agent or treatment option, when used in accordance with the invention, means decreased response to a standard dose of the drug or to a standard treatment protocol.

The term "decreased sensitivity" to a particular therapeutic agent or treatment option, when used in accordance with the invention, means decreased response to a standard dose of the agent or to a standard treatment protocol, where decreased response can be compensated for (at least partially) by increasing the dose of agent, or the intensity of treatment.

"Predicting response" of a subject, and variations thereof, can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

A "lupus therapeutic agent", a "therapeutic agent effective to treat lupus", and grammatical variations thereof, as used herein, refer to an agent that when provided in an effective amount is known, clinically shown, or expected by clinicians to provide a therapeutic benefit in a subject who has lupus. In one embodiment, the phrase includes any agent that is marketed by a manufacturer, or otherwise used by licensed clinicians, as a clinically-accepted agent that when provided in an effective amount would be expected to provide a therapeutic effect in a subject who has lupus. In one embodiment, a lupus therapeutic agent comprises a non-steroidal anti-inflammatory drug (NSAID), which includes acetylsalicylic acid (e.g., aspirin), ibuprofen (Motrin), naproxen (Naprosyn), indomethacin (Indocin), nabumetone (Relafen), tolmetin (Tolectin), and any other embodiments that comprise a therapeutically equivalent active ingredient(s) and formulation thereof. In one embodiment, a lupus therapeutic agent comprises acetaminophen (e.g., Tylenol), corticosteroids, or anti-malarials3 (e.g., chloroquine, hydroxychloroquine). In one embodiment, a lupus therapeutic agent comprises an immunomodulating drug (e.g., azathioprine, cyclophosphamide, methotrexate, cyclosporine). In one embodiment, a lupus therapeutic agent is an anti-B cell agent (e.g.; anti-CD20 (e.g., rituximab), anti-CD22), an anti-cytokine agent (e.g., anti-tumor necrosis factor α, anti-interleukin-1-receptor (e.g., anakinra), anti-interleukin 10, anti-interleukin 6 receptor, anti-interferon alpha, anti-B-stimulator), an inhibitor of costimulation e.g., anti-CD154, CTLA4-Ig (e.g., abatacept)), a modulator of B-cell anergy (e.g., UP 394 (e.g., abetimus)). In one embodiment, a lupus therapeutic agent comprises hormonal treatment (e.g., DHEA), and anti-hormonal therapy (e.g., the anti-prolactin agent bromocriptine). In one embodiment, a lupus therapeutic agent is an agent that provides immuno-adsorption, is an anti-complement factor (e.g., anti-C5a), T cell vaccination, cell transfection with T-cell receptor zeta chain, or peptide therapies (e.g., edratide targeting anti-DNA idiotypes).

A therapeutic agent that has "marketing approval", or that has been "approved as a therapeutic agent", or grammatical variations thereof of these phrases, as used herein, refer to an agent (e.g., in the form of a drug formulation, medicament) that is approved, licensed, registered or authorized by a relevant governmental entity (e.g., federal, state or local regulatory agency, department, bureau) to be sold by and/or through and/or on behalf of a commercial entity (e.g., a for-profit entity) for the treatment of a particular disorder lupus) or a patient subpopulation e.g., patients with lupus nephritis, patients of a particular ethnicity, gender, lifestyle, disease risk profile, etc.). A relevant governmental entity includes, for example, the Food and Drug Administration (FDA), European Medicines Evaluation Agency (EMEA), and equivalents thereof.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules which generally lack antigen speci- ficity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies e.g., bispecific antibodies so long as they exhibit the desired biological activity) and may also include certain antibody fragments (as described in greater detail herein). An antibody can be chimeric, human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fe region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an Flab')$_2$ fragment that has two antigen-combining sites and is still capable of cross-linking antigen.

"Fv" is a minimum antibody fragment which contains a complete antigen-binding site. In one embodiment, a two-chain Fv species consists of a dimer of one heavy- and one light-chain variable domain in tight, non-covalent association. Collectively, the six CDRs of an Fv confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$, antibody fragments originally were produced as pairs of Fab' fragments which have hinge cysteines between them. Other chemical couplings of antibody fragments are also known.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example; the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2$^{nd}$ ed. 1988); Hammerling et al., in: Monoclonal Antibodies and T-Hybridomas 563-681 (Elsevier, N.Y., 1981)), recombinant DNA methods see, e.g., U.S. Pat. No. 4,816,567), phage display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12.472 (2004); and Lee et al., J. Immunol. Methods 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et. al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies so long as they exhibit the desired biological activity U.S. Pat. No. 4,816,567; and Morrison et al., Proc. Natl. Acad. Sci. USA 81:6855-9855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fe), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Elude and Gross, Curr. Op. Biotech. 5:428-433 (1994).

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., J. Mol. Biol., 222: 581-597 (1991) and Hoogenboom et al., Nucl. Acids Res., 19: 4133-4137 (1991)); using human myeloma and mouse-human heteromyeloma cell lines for the production of human monoclonal antibodies see, e.g., Kozbor J. Immunol., 133: 3001 (1984); Brodeur et al., Monoclonal Antibody Production Techniques and Applications, pp. 55-93 (Marcel Dekker, Inc., New York, 1987); and Boerner et al., J. Immunol., 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., Proc. Natl. Acad. Sci USA, 90: 2551 (1993); Jakobovits et al., Nature, 362: 255 (1993); Bruggermann et al., Year in Immunol., 7: 33 (1993)). This definition of a human antibody specifically excludes a humanized antibody comprising antigen-binding residues from anon-human animal.

An "affinity matured" antibody is one with one or more alterations in one or more CDRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of HVR and/or framework residues is described by: Barbas et al. Proc. Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking antibody" or an "antagonist antibody" is one which inhibits or reduces a biological activity of the antigen it binds. Certain blocking antibodies or antagonist antibodies partially or completely inhibit the biological activity of the antigen.

A "small molecule" or "small organic molecule" is defined herein as an organic molecule having a molecular weight below about 500 Daltons.

The word "label" when used herein refers to a detectable compound or composition. The label may be detectable by itself (e.g., radioisotope labels or fluorescent labels) or, in the case of an enzymatic label, may catalyze chemical alteration of a substrate compound or composition which results in a detectable product. Radionuclides that can serve as detectable labels include, for example, I-131, I-123, I-125, Y-90, Re-188, Re-186, At-211, Cu-67, Bi-212, and Pd-109.

An "isolated" biological molecule, such as a nucleic acid, polypeptide, or antibody, is one which has been identified and separated and/or recovered from at least one component of its natural environment.

Reference to "about" a value or parameter herein includes and describes) embodiments that are directed to that value or parameter per se. For example, description referring to "about X" includes description of "X."

General Techniques

Nucleotide variations associated with lupus are provided herein. These variations provide biomarkers for lupus, and/or predispose or contribute to development, persistence and/or progression of lupus. Accordingly, the invention disclosed herein is useful in a variety of settings, e.g., in methods and compositions related to lupus diagnosis and therapy.

In certain embodiments, the methods relate to prognosis, i.e., the prediction of the likelihood of autoimmune disorder-attributable disease symptoms, including, for example, recurrence, flaring, and drug resistance, of an autoimmune disease such as lupus. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely. Diagnosis of SLE may be according to current American College of Rheumatology (ACR) criteria. Active disease may be defined by one British Isles Lupus Activity Group's (BILAG) "A" criteria or two BILAG "B" criteria. Some signs, symptoms, or other indicators used to diagnose SLE adapted from: Tan et al. "The Revised Criteria for the Classification of SLE" *Arth Rheum* 25 (1982) may be malar rash such as rash over the cheeks, discoid rash, or red raised patches, photosensitivity such as reaction to sunlight, resulting in the development of or increase in skin rash, oral ulcers such as ulcers in the nose or mouth, usually painless, arthritis, such as non-erosive arthritis involving two or more peripheral joints (arthritis in which the bones around the joints do not become destroyed), serositis, pleuritis or pericarditis, renal disorder such as excessive protein in the urine (greater than 0.5 gm/day or 3+ on test sticks) and/or cellular casts (abnormal elements derived from the urine and/or white cells and/or kidney tubule cells), neurologic signs, symptoms, or other indicators, seizures (convulsions), and/or psychosis in the absence of drugs or metabolic disturbances that are known to cause such effects, and hematologic signs, symptoms, or other indicators such as hemolytic anemia or leukopenia (white bloodcount below 4,000 cells per cubic millimeter) or lymphopenia less than 1,500 lymphocytes per cubic millimeter) or thrombocytopenia (less than 100,000 platelets per cubic millimeter). The leukopenia and lymphopenia generally must be detected on two or more occasions. The thrombocytopenia generally must be detected in the absence of drugs known to induce it. The invention is not limited to these signs, symptoms, or other indicators of lupus.

Detection of Genetic Variations

Nucleic acid, according to any of the above methods, may be genomic DNA; RNA transcribed from genomic DNA; or cDNA generated from RNA. Nucleic acid may be derived from a vertebrate, e.g., a mammal. A nucleic acid is said to be "derived from" a particular source if it is obtained directly from that source or if it is a copy of a nucleic acid found in that source.

Nucleic acid includes copies of the nucleic acid, e.g., copies that result from amplification. Amplification may be desirable in certain instances, e.g., in order to obtain a desired amount of material for detecting variations. The amplicons may then be subjected to a variation detection method, such as those described below, to determine whether a variation is present in the amplicon.

Variations may be detected by certain methods known to those skilled in the art. Such methods include, but are not limited to, DNA sequencing; primer extension assays, including allele-specific nucleotide incorporation assays and allele-specific primer extension assays (e.g., allele-specific PCR, allele-specific ligation chain reaction (LCR), and gap-LCR); allele-specific oligonucleotide hybridization assays (e.g., oligonucleotide ligation assays); cleavage protection assays in which protection from cleavage agents is used to detect mismatched bases in nucleic acid duplexes; analysis of MutS protein binding; electrophoretic analysis comparing the mobility of variant and wild type nucleic acid molecules; denaturing-gradient gel electrophoresis (DGGE, as in, e.g., Myers et al. (1985) *Nature* 313:495); analysis of RNase cleavage at mismatched base pairs; analysis of chemical or enzymatic cleavage of heteroduplex DNA; mass spectrometry (e.g., MALDI-TOF); genetic bit analysis (GBA); 5' nuclease assays (e.g., TaqMan®)); and assays employing molecular beacons. Certain of these methods are discussed in further detail below.

Detection of variations in target nucleic acids may be accomplished by molecular cloning and sequencing of the target nucleic acids using techniques well known in the art. Alternatively, amplification techniques such as the polymerase chain reaction (PCR) can be used to amplify target nucleic acid sequences directly from a genomic DNA preparation from tumor tissue. The nucleic acid sequence of the amplified sequences can then be determined and variations identified therefrom. Amplification techniques are well known in the art, e.g., polymerase chain reaction is described in Saiki et al., *Science* 239:487, 1988; U.S. Pat. Nos. 4,683,203 and 4,683,195.

The ligase chain reaction, which is known in the art, can also be used to amplify target nucleic acid sequences. See, e.g., Wu et al., *Genomics* 4:560-569 (1989). In addition, a technique known as allele-specific PCR can also be used to detect variations (e.g., substitutions). See, e.g., Ruano and Kidd (1989) *Nucleic Acids Research* 17:8392; McClay al.

(2002) *Analytical* Biochem. 301:200-206. In certain embodiments of this technique, an allele-specific primer is used wherein the 3' terminal nucleotide of the primer is complementary to (i.e., capable of specifically base-pairing with) a particular variation in the target nucleic acid. If the particular variation is not present, an amplification product is not observed. Amplification Refractory Mutation System (ARMS) can also be used to detect variations (e.g., substitutions). ARMS is described, e.g., in European Patent Application Publication No. 0332435, and in Newton et al., *Nucleic Acids Research,* 17:7, 1989.

Other methods useful for detecting variations (e.g., substitutions) include, but are not limited to, (1) allele-specific nucleotide incorporation assays, such as single base extension assays (see, e.g., Chen et al. (2000) *Genome Res.* 10:549-557; Fan et al. (2000) *Genome Res.* 10:853-860; Pastinen et al. (1997) *Genome Res.* 7:606-614; and Ye et al. (2001) *Hum. Mut.* 17:305-316); (2) allele-specific primer extension assays (see, e.g., Ye et al. (2001) *Hum. Mut.* 17:305-316; and Shen et al. *Genetic Engineering News,* vol. 23, Mar. 15, 2003), including allele-specific PCR; (3) 5'nuclease assays (see, e.g., De La Vega et al, (2002) *BioTechniques* 32:S48-S54 (describing the TaqMan® assay); Ranade et al. (2001) *Genome Res.* 11:1262-1268; and Shi (2001) *Clin. Chem.* 47:164-172); (4) assays employing molecular beacons (see, e.g., Tyagi et al. (1998) *Nature Biotech.* 16:49-53; and Mhlanga et al. (2001) *Methods* 25:463-71); and (5) oligonucleotide ligation assays (see, e.g., Grossman et al, (1994) *Nuc. Acids Res.* 22:4527-4534; patent application Publication No. US 2003/0119004 A1; PCT International Publication No. WO 01/92579 A2; and U.S. Pat. No. 6,027,889).

Variations may also be detected by mismatch detection methods. Mismatches are hybridized nucleic acid duplexes which are not 100% complementary. The lack of total complementarity may be due to deletions, insertions, inversions, or substitutions. One example of a mismatch detection method is the Mismatch Repair Detection (MRD) assay described, e.g., in Faham et al., *Proc. Natl Acad. Sci. USA* 102:14717-14722 (2005) and Faham et al., *Hum. Mol. Genet.* 10:1657-1664 (2001). Another example of a mismatch cleavage technique is the RNase protection method, which is described in detail in Winter et al., *Proc. Natl. Acad. Sci. USA,* 82:7575, 1985, and Myers et al., *Science* 230: 1242, 1985. For example, a method of the invention may involve the use of a labeled riboprobe which is complementary to the human wild-type target nucleic acid. The riboprobe and target nucleic acid derived from the tissue sample are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid, but can a portion of the target nucleic acid, provided it encompasses the position suspected of having a variation.

In a similar manner, DNA probes can be used to detect mismatches, for example through enzymatic or chemical cleavage. See, e.g., Cotton et al., *Proc. Natl. Acad. Sci. USA,* 85:4397, 1988; and Shenk et al., *Proc. Natl. Acad. Sci. USA,* 72:989, 1975. Alternatively, mismatches can be detected by shifts in the electrophoretic mobility of mismatched duplexes relative to matched duplexes. See, e.g., Cariello, *Human Genetics,* 42:726, 1988. With either riboprobes or DNA probes, the target nucleic acid suspected of comprising a variation may be amplified before hybridization. Changes in target nucleic acid can also be detected using Southern hybridization, especially if the changes are gross rearrangements, such as deletions and insertions.

Restriction fragment length polymorphism (RFLP) probes for the target nucleic acid or surrounding marker genes can be used to detect variations, e.g., insertions or deletions. Insertions and deletions can also be detected by cloning, sequencing and amplification of a target nucleic acid. Single stranded conformation polymorphism (SSCP) analysis can also be used to detect base change variants of an allele. See, e.g. Orita et al., *Proc. Natl. Acad. Sci. USA* 86:2766-2770, 1989, and *Genomics,* 5:874-879, 1989.

A microarray is a multiplex technology that typically uses an arrayed series of thousands of nucleic acid probes to hybridize with, e.g, a cDNA or cRNA sample under high-stringency conditions. Probe-target hybridization is typically detected and quantified by detection of fluorophore-, silver-, or chemiluminescence-labeled targets to determine relative abundance of nucleic acid sequences in the target. In typical microarrays, the probes are attached to a solid surface by a covalent bond to a chemical matrix via epoxy-silane, amino-silane, polyacrylamide or others). The solid surface is for example, glass, a silicon chip, or microscopic beads. Various microarrays are commercially available, including those manufactured, for example, by Affymetrix, Inc. and Illumina, Inc.

A biological sample may be obtained using certain methods known to those skilled in the art. Biological samples may be obtained from vertebrate animals, and in particular, mammals. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. Variations in target nucleic acids (or encoded polypeptides) may be detected from a tumor sample or from other body samples such as urine, sputum or serum. (Cancer cells are sloughed off from tumors and appear in such body samples.) By screening such body samples, a simple early diagnosis can be achieved for diseases such as cancer. In addition, the progress of therapy can be monitored more easily by testing such body samples for variations in target nucleic acids (or encoded polypeptides). Additionally, methods for enriching a tissue preparation for tumor cells are known in the art. For example, the tissue may be isolated from paraffin or cryostat sections. Cancer cells may also be separated from normal cells by flow cytometry or laser capture microdissection.

Subsequent to the determination that a subject, or the tissue or cell sample comprises a genetic variation disclosed herein, it is contemplated that an effective amount of an appropriate lupus therapeutic agent may be administered to the subject to treat the lupus condition in the subject. Diagnosis in mammals of the various pathological conditions described herein can be made by the skilled practitioner. Diagnostic techniques are available in the art which allow, for the diagnosis or detection of lupus in a mammal.

A lupus therapeutic agent can be administered in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through mini-pump infusion using various commercially available devices.

Effective dosages and schedules for administering lupus therapeutic agents may be determined empirically, and making such determinations is within the skill in the art. Single or multiple dosages may be employed. For example, an effective dosage or amount of interferon inhibitor used alone may range from about 1 mg/kg to about 100 mg/kg of body weight or more per day. Interspecies scaling of dosages can be performed in a manner known in the art, e.g., as disclosed in Mordenti et al., Pharmaceut. Res., 8:1351 (1991).

When in vivo administration of a lupus therapeutic agent is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or U.S. Pat. No. 5,225,212. It is anticipated that different formulations will be effective for different treatment compounds and different disorders, that administration targeting one organ or tissue, for example, may necessitate delivery in a manner different from that to another organ or tissue.

It is contemplated that yet additional therapies may be employed in the methods. The one or more other therapies may include but are not limited to, administration of steroids and other standard of care regimens for the disorder in question. It is contemplated that such other therapies may be employed as an agent separate from, e.g., a targeted lupus therapeutic agent.

Kits

For use in the applications described or suggested above, kits or articles of manufacture are also provided. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be a polynucleotide specific for a polynucleotide comprising a SLE risk locus. Where the kit utilizes nucleic acid hybridization to detect the target nucleic acid, the kit may also have containers containing nucleotide(s) for amplification of the target nucleic acid sequence and/or a container comprising a reporter means, such as a biotin-binding protein, such as avidin or streptavidin, bound to a reporter molecule, such as an enzymatic, fluorescent, or radioisotope label.

Kits will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc. An additional component is an enzyme, for example, including but not limited to, a nuclease, a ligase, or a polymerase.

Methods of Marketing

Also provided are methods for marketing a lupus therapeutic agent or a pharmaceutically acceptable composition thereof comprising promoting to, instructing, and/or specifying to a target audience, the use of the agent or pharmaceutical composition thereof for treating a patient or patient population with lupus from which a sample has been obtained showing the presence of a genetic variation as disclosed herein.

Marketing is generally paid communication through a non-personal medium in which the sponsor is identified and the message is controlled. Marketing for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The marketing of diagnostic methods may be accomplished by any means. Examples of marketing media used to deliver these messages include television, radio, movies, magazines, newspapers, the internet, and billboards, including commercials, which are messages appearing in the broadcast media.

The type of marketing used will depend on many factors, for example, on the nature of the target audience to be reached, e.g., hospitals, insurance companies, clinics, doctors, nurses, and patients, as well as cost considerations and the relevant jurisdictional laws and regulations governing marketing of medicaments and diagnostics. The marketing may be individualized or customized based on user characterizations defined by service interaction and/or other data such as user demographics and geographical location.

The following are examples of the methods and compositions of the invention. It is understood that various other embodiments may be practiced, given the general description provided above.

EXAMPLES

Throughout the Examples, references to certain publications are denoted by numbers, which have complete bibliography information at the end of the Examples section.

Example 1

Identification of Novel Risk Loci for SLE

Methods and Subjects

Subjects

The selection and genotyping of SLE cases, the samples used in the genome-wide association scan (GWAS) as well as controls from the New York Health Project (NYHP) collection (Mitchell et al.; J Urban Health 81(2):301-10 (2004)), were described previously (Hom et al., N Engl J Med 358(9):900-9 (2008)). As detailed below, the SLE cases consisted of three case series: a) 338 cases from the Autoimmune Biomarkers Collaborative Network (ABCoN) (Bauer et. al., PLoS medicine 3(12):c491 (2006)), an NIH/NIAMS-funded repository, and 141 cases from the Multiple Autoimmune Disease Genetics Consortium (MADGC) (Criswell et al., Am J Hum Genet 76(4):561-71 (2005)); b) 613 cases from the University of California San Francisco (UCSF) Lupus Genetics Project (Seligman et al., Arthritis Rheum 44(3):618-25 (2001); Remmers et al., N Engl J 357(10):977-86 (2007)); and c) 335 cases from the University of Pittsburgh Medical Center (UPMC) (Demirei et al., Ann Hum Genet 71(Pt 3):308-11 (2007)) and 8 cases from The Feinstein Institute for Medical Research. The controls were 1861 samples from the NYHP collection, 1722 samples from the publicly available iControlDB database (available at Illumina Inc.), and 4564 samples from the publicly available National Cancer Institute Cancer Genetic Markers of Susceptibility (CGEMS) project available at the URL: cgems(dot)cancer(dot)gov).

Genomewide Data Set of 1310 SLE Cases and 7859 Controls

We previously described the selection and genotyping of SLE case samples (Horn et al., N Engl J Med 358(9):900-9 (2008)). All SLE cases were North Americans of European descent, as determined by self-report and confirmed by genotyping. The diagnosis of SLE (fulfillment of four or more of the American College of Rheumatology [ACR] defined criteria [Hochberg et al., Arthritis Rheum 40(9): 1725[1997]]) was confirmed in all cases by medical record review (94%) or through written documentation of criteria by treating rheumatologists (6%). Clinical data for these case series are presented elsewhere (Seligman et al., Arthritis Rheum 44(3):618-25 (2001); Criswell et al., Am J Hum Genet 76(4):561-71 (2005); Bauer et al., PLoS medicine 3(12):e491 (2006); Demirei et al., Ann Hum Genet 71(Pt 3):308-11 (2007); Remmers et al., N Engl J Med 357(10): 977-86 (2007)). Genotyping and selection of the NYHP samples was described previously (Horn et al., N Engl J Med 358(9):900-9 (2008)). Table 1 describes the number of samples contributed organized by site.

Sample and SNP filtering was conducted using analytical modules within the software programs PLINK and EIGENSTRAT as described below (see also Purcell et al., Am J Hum Genet 81(3):559-75 (2007); Price et al., Nat Genet 38(8):904-09 (2006)). The genomewide SNP data were used in this study to facilitate close matching of cases and controls, and to provide genotypes at the confirmed and suspected SLE loci.

TABLE 1

Number of samples analyzed in genome-wide and replication study organized by site.

| | Case Collection | N | Control Collection | N |
|---|---|---|---|---|
| Discovery samples | | | | |
| GWAS[a] | | 1310 | | 7859 |
| Replication samples | | | | |
| US[b] | PROFILE | 415 | NYHP | 776 |
| | UMN | 366 | ALZ | 2215 |
| | UCSF | 284 | | |
| | UPMC | 52 | | |
| | JHU | 12 | | |
| | Total | 1129 | | 2991 |

TABLE 1-continued

Number of samples analyzed in genome-wide and replication study organized by site.

| | Case Collection | N | Control Collection | N |
|---|---|---|---|---|
| Sweden[c] | Umeå | 244 | Umeå | — |
| | Uppsala | 145 | Uppsala | 132 |
| | Stockholm | 270 | Stockholm[d] | 1112 |
| | Lund | 155 | Lund | 94 |
| | Total | 834 | Total | 1338 |
| Total | | 3273 | | 12188 |

[a]Samples from the genome-wide association scan described (Horn. G. et al, N Engl J Med 358:900-9 (2008)).
[b]Independent SLE cases from a U.S. cohort drawn from the PROFILE SLE consortium, University of California-San Francisco (UCSF) (Thorburn, C.M. et al, Genes Immun 8:279-87 (2007)), University of Pittsburgh Medical Center (UPMC), University of Minnesota (UMN), and Johns Hopkins University (JHU). U.S. controls from the New York Health Project (Gregersen et al.) and Alzhiemers cases and controls from the University of Pittsburgh and the NCRAD.
[c]SLE cases and controls from Stockholm, Karolinska, Solna, Uppsala, Lund and Umeå, Sweden.
[d]823 of the controls from Stockholm were genotyped using the Illumina 317K SNP array. SNPs in these samples were imputed and analyzed as described in Methods.

Custom SNP Array

A custom array was designed with 10,848 SNPs that passed the quality control measures described below. The complete array had 12,864 SNPs but 2016 SNPs failed the quality control measures leaving 10,848 SNPs that were advanced into the analysis. The custom array consisted of 3,188 SNPs selected based on a nominal P<0.05 in a SLE genome-wide association scan, 505 SNPs from 25 previously reported SLE risk loci, 42 SNPs selected after a literature search for confirmed risk alleles from other autoimmune diseases and 7,113 SNP's used for ascertaining and controlling for population substructure. The latter group included SNPs that have been used to define continental population differences (Kosoy, R. et al., Hum. Mutat. 30:69-78 (2009)) and SNPs enriched for European population substructure (Tian, C. et al., PLoS Genet 4, e4 (2008)). The custom array was manufactured by Illumina, Inc. using their iSetect Custom BeadChip and the rs identification numbers we provided for the SNPs that passed the quality control filters described below.

Quality Control and Imputation

For the U.S. data, a total of 1,464 U.S. cases and 3,078 U.S. controls were genotyped on the custom Illumina chip described above, also referred to herein as the custom 12K chip. We used stringent quality control (QC) criteria to ensure that high quality data was included in the final analysis. Specifically, we a excluded 116 individuals who had >5% missing data and b) excluded 279 individuals based on cryptic relatedness and duplicate samples based on Identical by State (IBS) status (PI Hat>0.15). We included only SNPs with a)<5% missing data, b) Hardy-Weinberg Equilibrium (HWE) p-value $>1 \times 10^{-6}$, c) Minor Allele Frequency (MAF)>0.01% and d) SNPs with p-value $>1 \times 10^{-5}$ in a test for differential missingness between cases and controls. SNPs were also examined for batch effects. After applying the above filters, a final set of 1,144 cases and 3,003 controls and 11,024 SNPs were available for analysis. All QC tests were performed using PLINK (Purcell et al., Am J Hum Genet 81(3):559-75 (2007)).

For the Swedish data, a set of 888 cases and 527 controls genotyped on the custom 12K chip were available for analysis. A separate set of 1,115 Swedish controls genotyped on the Illumina, Inc. 317K Human HapMap SNP bead array (also referred to herein as the 317K array) was also incorporated into the analysis. We followed the following steps to combine the two data sets. First, an overlapping data set of 6,789 SNPs between the 12K and 317K data was created. We used this data set to examine the Swedish replication cohort for cryptic relatedness and duplicate samples. As a result, 313 samples were excluded (PI Hat>0.15). After quality control checks, we forwarded for analysis 863 cases and 523 controls genotyped on the custom 12K chip and 831 controls genotyped on the 317K Illumina chip. Second, we imputed (see below) the 831 Swedish controls genotyped with the 317K array to create a larger set of overlapping SNPs. Of the remaining SNPs, we captured 4,605 SNPs by imputation. A final set of 11,394 overlapping SNPs was forwarded to analysis. We filtered the SNPs in this data set using the same thresholds as described above. The remaining 1,250 SNPs not captured by the imputation were analyzed only in the original set of Swedish samples genotyped on the 12K chip.

The 831 Swedish controls genotyped with the 317K array were imputed using MACH (a Markov Chain based haplotyping software program available at the URL sph(dot)umich(dot)edu(slash)csg(slash)abecasis(slash)MACH) using Phase II HapMap CEU samples as a reference. Phase II HapMap CEU refers to samples from the Human Haplotype Project known as Utah residents with ancestry from northern and western Europe (CEU) from the "Phase II" data release. (See also Li et al. *Am J Hum Genet* S79 at 2290 (2006)). Before imputation, we applied stringent quality control checks on the 317K SNPs. A subset of 293,242 markers passing the following criteria (1) MAF>1%, (2) missing rate <5% and (3) HWE p-value >1×10$^{-6}$ were included in the imputation. After the imputation, SNPs with low imputation quality, i.e. R-squared_Hat (RSQR_HAT)<0.40 reported by MACH, were discarded. An overlapping set of 11,394 markers was available for analysis. To take into account the uncertainty in imputation, probabilistic scores rather than genotype calls were used in the analysis.

For imputation of genome-wide association study samples, genotype data used in the meta-analysis was from 1310 SLE cases genotyped with the Illumina 550K genome-wide SNP platform (see Ham, (i. et al., N Engl J Med 358:900-9 (2008)). The selection and genotyping of the SLE case samples was described previously (Horn, a et al., N Engl. J Med 358:900-9 (2008)). In addition to the 3,583 controls previously described (Horn, G. et al., N Engl J Med 358:900-9 (2008)), 4,564 control samples from the publicly available Cancer Genetics Markers of Susceptibility (CGEMS) project were included after obtaining approval (available at the URL: cgems(dot)cancer(dot)gov). The entire sample of 7,859 controls was examined using the data quality control filters as previously described (Hom, G. et al., N Engl J Med 358:900-9 (2008)). We next used IMPUTE version 1 (available at the URL www(dot)stats(dot)ox(dot)ac(dot) (dot)uk(slash)~marchini(slash)software(slash)gwas (slash)impute(dot)html) to infer genotypes using HapMap Phase II CEU samples as a reference (Marchini, J. et al., Nat. Genet 39:906-913 (2007)). We used SNPTEST (available at the URL www(dot)stats(dot)ox(dot)ac(dot)uk(slash)~marchini(slash)software(slash)gwas(slash)snptest_v1(dot)1(dot)4(dot)html) to generate association statistics (Marchini, J. et al., Nat. Genet. 39:906-913 (2007)). Specifically, association statistics were generated using an additive model (-Frequentist 1 option in SNPTEST), adjusted for the uncertainty of the imputed genotype (-proper option in SNPTEST). The rank ordered list of association statistics was used to select regions for replication as described.

Population Stratification in Replication Samples

For each replication cohort, we used ancestry informative markers to correct for possible population stratification. A subset of 5,486 uncorrelated ancestry informative markers that passed stringent quality control criteria were used to infer the top ten principal components of genetic variation using the software EIGENSTRAT (Price et al., Nat Genet 38(81:904-09 (2006)). Outliers were removed from each sample set (defined as $\sigma$>6). Specifically, we removed 27 genetic outliers from the US cohort and 45 outliers from the Swedish cohort respectively. Some degree of population stratification along the first two eigenvectors was observed in both the US and Swedish replication collections. To correct for the case-control stratification, we used one of the following strategies: (1) we applied the correction of the Cochran-Armitage test statistic incorporated in EIGENSTRAT to the US replication data set and to Swedish data set wherever genotype data was available; (2) we used principal components as covariates in a logistic regression model in the analysis of the imputed Swedish data.

Association Analysis

For the U.S. data, some inflation in the test statistics was observed after performing an uncorrected 1-degree of freedom allelic test for association (PLINK [Purcell, S. et al. Am J Hum Genet 81:559-75 (2007)]). To correct for population stratification in the U.S. sample, principal component analysis (EIGENSTRAT) using 5,486 uncorrelated ancestry informative markers was conducted. First, we removed genetic outliers (defined as $\sigma$>6). Second, Cochran-Armitage trend chi-square test statistics were calculated for each genotyped SNP in 1,129 cases and 2,991 controls, followed by adjustment of the test statistic value of each SNP in EIGENSTRAT using the first four eigenvectors. Two-tailed p-values based on the test-statistic for each SNP was calculated. After correction for population stratification, the $\lambda_{gc}$, in the U.S. samples was 1.05.

For the Swedish data, we examined the Swedish cohort for hidden population stratification using 5,486 ancestry informative markers genotyped in the 12K samples as well as in additional Illumina 317K controls. After removal of genetic outliers, we had 834 cases and 515 controls genotyped on the custom 12K chip and 823 controls genotyped on the Illumina 317K chip. We used the correction of the test statistic implemented in EIGENSTRAT on the overlapping set of 6789 SNPs between the two Illumina arrays. To correct for stratification in the set of 4605 SNPs genotyped in the 12K samples and imputed in the Illumina 317K samples, we used the first four eigenvectors determined above as covariates in a logistic regression model implemented in SNPTEST because EIGENSTRAT was not intended for use with imputed genotype data. A small set of 1250 markers not captured by imputation in the Illumina 317K SNPs was analyzed only in the 834 cases and 515 controls genotyped on the custom 12K chip. After correction for population stratification the $\lambda_{gc}$ in the Swedish samples was 1.10.

Meta-Analysis

We used a weighted z-score method to conduct the meta-analysis. To combine results across different cohorts, alleles were oriented to the forward strand of the National Center for Biotechnology Information (NCBI) 36 reference sequence of the human genome to avoid ambiguity associated with C/G and A/T SNPs. The NCBI reference sequence of the human genome is available at the URL www(dot)ncbi(dot)nlm(dot)nih(dot)gov. See also Pruitt et al., Nucl. Acids Res. 35 (database issue):D61-D65 (2007). P values for each cohort were converted to z-scores taking into account direction of effect relative to an arbitrary reference allele. A weighted sum of z-scores was calculated by weighing each z-score by the square root of the sample size for each cohort and then dividing the sum by the square root of the total sample size. The combined z-score for the Swedish and U.S. replication cohorts were converted to one-tailed p values. The meta-analysis z-score was converted to a two-tailed p value and evidence for association was evaluated. We considered SNPs passing a threshold of $5 \times 10^{-8}$ overwhelmingly associated with SLE. Loci with combined p-value less than $1 \times 10^{-5}$ that did not pass genome-wide significance were considered strong candidates. The meta-analysis method was carried out using the freely available METAL software package available at the URL www(dot)sph(dot)umich(dot)edu(slash)csg(slash)abecasis(slash)Metal). To calculate pooled odds ratios, we used the Cochran-Mantel-Haenszel (CMH) method as implemented by the METAL software. Odds ratios were calculated relative to the risk allele for each SNP. Also, a weighted average allele frequency in controls was calculated relative to the risk allele of each SNP.

Percent Variance Explained

For SNPs previously associated with SLE and SNPs with a meta p-value less than $1 \times 10^{-5}$ in our replication study, we calculated the percentage of variance explained. We used a liability threshold model which assumes that SLE has an underlying liability score which is normally distributed with mean 0 and variance one. We assumed prevalence of 0.1% of SLE in the general population. To calculate threshold for each genotype, we used allele frequencies in controls and an effect size corresponding to the odds ratio (OR) from our analysis.

Interaction Analysis

To look for epistatic effects between the top signals, we compiled a list of all SNPs in Tables 2, 4, and 6 and carried out an interaction analysis in each replication cohort using the epistasis option implemented in PLINK. To achieve greater, statistical power, we performed a case-only analysis. After correcting for the number of tests, none of the SNP-SNP interactions were found significant at the p<0.05 level.

Conditional Analysis

In each genomic region showing strong association with SLE, we selected the SNP showing the strongest signal. We used PLINK to condition on this SNP and looked for other SNPs showing strong association with SLE.
A Lame-Scale Replication Study Identifies TNIP1, PRDM1, JAZF1, UHRF1BP1, and IL10 as Novel Risk Loci for Systemic Lupus Erythematosus Recent genome-wide association (GWA) and candidate gene studies have identified at least 15 common risk alleles that achieve genome-wide significance ($P<5 \times 10^{-8}$). These include genes important for adaptive immunity and the production of autoantibodies (HLA class II alleles, BLK, PTPN22, and BANK1) and genes with roles in innate immunity and interferon signaling (ITGAM, TNFAIP3, STAT4, and IRF5) (Cunninghame Graham, D. S. et al., Nat. Genet. 40:83-89 (2008); Graham, R. R. et al., Nat. Genet. 40(9):1059-61 (2008); Graham, R. R., et al., J Intern Med 265:680-88 (2009); Harley, J. B. et al., Nat. Genet. 40:204-10 (2008); Ham, G. et al., N Engl J Med 358:900-9 (2008); Kozyrev, S. V. et al., Nat. Genet. 40:211-6 (2008); Sawalha, A. H. et al., PLoS ONE 3:e1727 (2008); Sigurdsson, S. et al., Am J Hum Genet 76:528-37 (2005)). To identify additional risk loci we performed a targeted replication study of SNPs from 2,466 loci that showed a nominal P value <0.05 in a recent GWAS7 scan of 1310 cases and 7859 controls. We also genotyped SNPs from 25 previously reported SLE risk loci, 42 SNPs from 35 loci implicated in other autoimmune diseases, and over 7,000 ancestry informative markers. An overview of the experimental design is shown in FIG. 1. The SNPs described above were incorporated into an Illumina custom SNP array. The array was genotyped in independent cases and controls from the U.S. and Sweden. Eight hundred twenty-three of the Swedish controls were genotyped using the Illumina 310K SNP array and variants were analyzed as described in the Methods above.

Specifically, as described above, we designed a custom SNP array consisting of >12,000 variants and genotyped two independent SLE case and control populations from the United States (1,129 SLE cases and 2,991 controls) and Sweden (834 SLE cases and 1,338 controls). Included among the U.S. controls were 2,215 Alzheimer's disease case/control samples, which were felt to be acceptable as controls since the genetic basis of SLE and Alzheimer's are expected to be independent. We next applied data quality filters to remove poor performing samples and SNPs, population outliers and duplicate/related individuals (see Methods above). Following these quality control measures, a final set of 10,848 SNPs was examined as indicated in FIG. 1. Association statistics for 3,735 variants were calculated and corrected for population stratification using 7,113 ancestry informative markers (see Methods above).

We first examined 25 variants (from 23 loci) that were previously reported to be associated with SLE (see Table 2). We found further evidence of association for 21 of the variants (P<0.05), including 9 loci that reached genome-wide significance ($P<5 \times 10^{-8}$) in the current combined data set. Among the genome-wide significant results were HLA Class II DR3 (DRB1*0301), IRF5, TNFAIP3, BLK, STAT4, ITGAM, PTPN22, PHRF1 (KIAA1542), and TNFSF4 (OX40L). The analysis provided additional evidence for variants from 9 loci where a single previous study reported genome-wide levels of significance: HLA*DR2, TNFAIP3 (rs6920220), BANK1, ATG5, PTTG1, PXK, FCGR2A, UBE2L3, and IRAK1/MECP2).

An earlier candidate gene study identified MECP2 (Sawalha, A. H. et al., PLoS ONE 3:e1727 (2008)) as a potential risk allele for SLE. However, in the current dataset, SNPs near IRAK1, a gene critical for toll-like receptor 7 and 9 signaling and located within the identified region of linkage disequilibrium surrounding MECP2, showed the strongest evidence of association. Similar findings were recently reported (Jacob, C. O. et al., Proc. Natl. Acad. Sci. USA (2009)), and further work will be needed to determine the causal allele in the IRAK1/MECP2 locus. We found additional evidence of association for 3 loci—TYK2, ICA1 and NMNAT2—that had previously shown significant but not genome-wide level evidence for association. (Harley, J. B. et al., Nat. Genet. 40:204-10 (2008); Sigurdsson S. et al., Am J Hum Genet 76:528-37 (2005)). For four previously implicated variants—LYN, SCUBE1, TLR5 and LY9—no evidence of association was observed in the combined dataset.

To identify novel SLE risk loci, we examined a total of 3,188 SNPs from 2,446 distinct loci that showed evidence of association to SLE in our genome-wide dataset (Hom, G. et al., N Engl J Med 358, 900-9 (2008)), which comprised 502,033 SNPs genotyped in 1,310 SLE cases and an expanded set of 7,859 controls. Using this dataset, we imputed >2.1 M variants using Phase II HapMap CEU samples as a reference (see Methods above), and generated a rank-ordered list of association statistics. Variants with $P<0.05$ were selected for possible inclusion on the custom replication array. For efficient genotyping, we identified groups of correlated variants ($r^2>0.2$), followed by selection of at least two SNPs from each group where the lowest P value was <0.001. For the remaining groups, the SNP with the lowest P value in the group was included. In the replication samples, we calculated the association statistics (see Methods) and observed a significant enrichment of the replication results relative to the expected null distribution. Excluding the previously reported SLE risk alleles, there were 134 loci with a $P<0.05$ (expected 64, $P=2\times10^{-15}$) and 12 loci with a $P<0.001$ (expected 1, $P=1\times10^{-9}$), suggesting the presence of true positives.

Figure 2A:
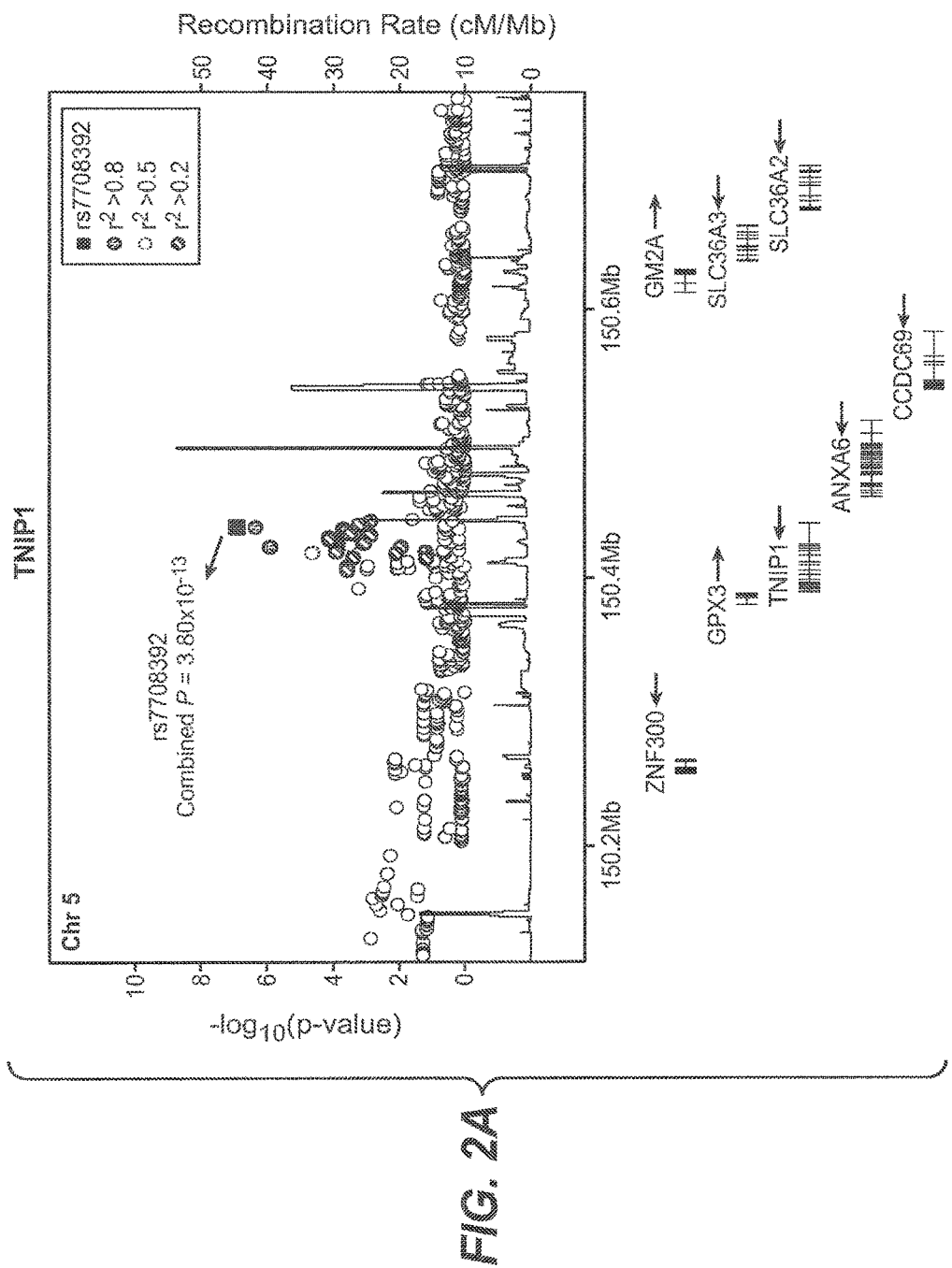
FIGS. 2A-2F show novel genome-wide significant associations in SLE and the identification of novel risk loci within TNIP1 (FIG. 2A), PRDM1 (FIG. 2B), JAZF1 (FIG. 2C), UHRF1BP1 (FIG. 2D), and IL10 (FIG. 2E) as described in Example 1.
Figure 2B:
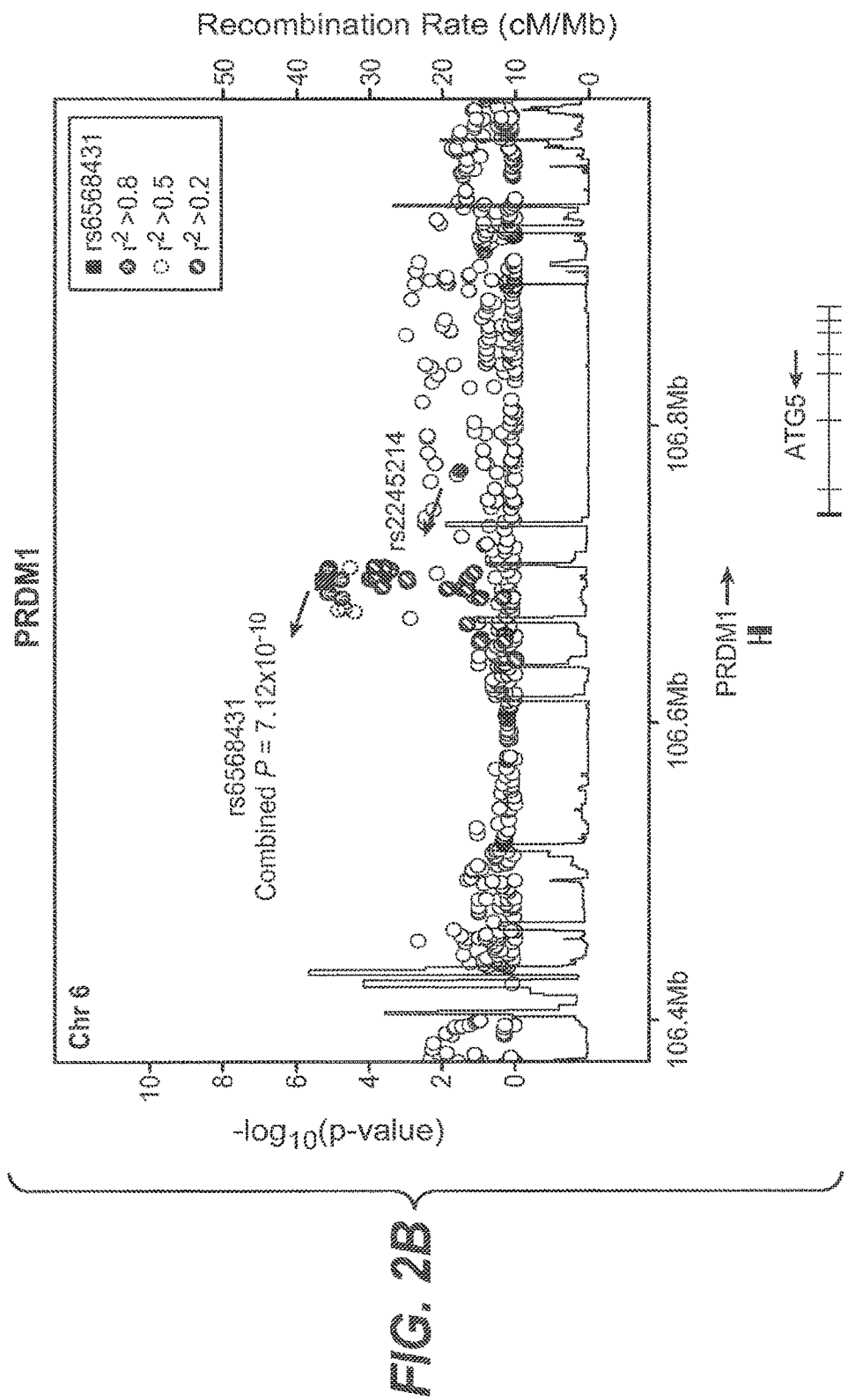
Figure 2C:
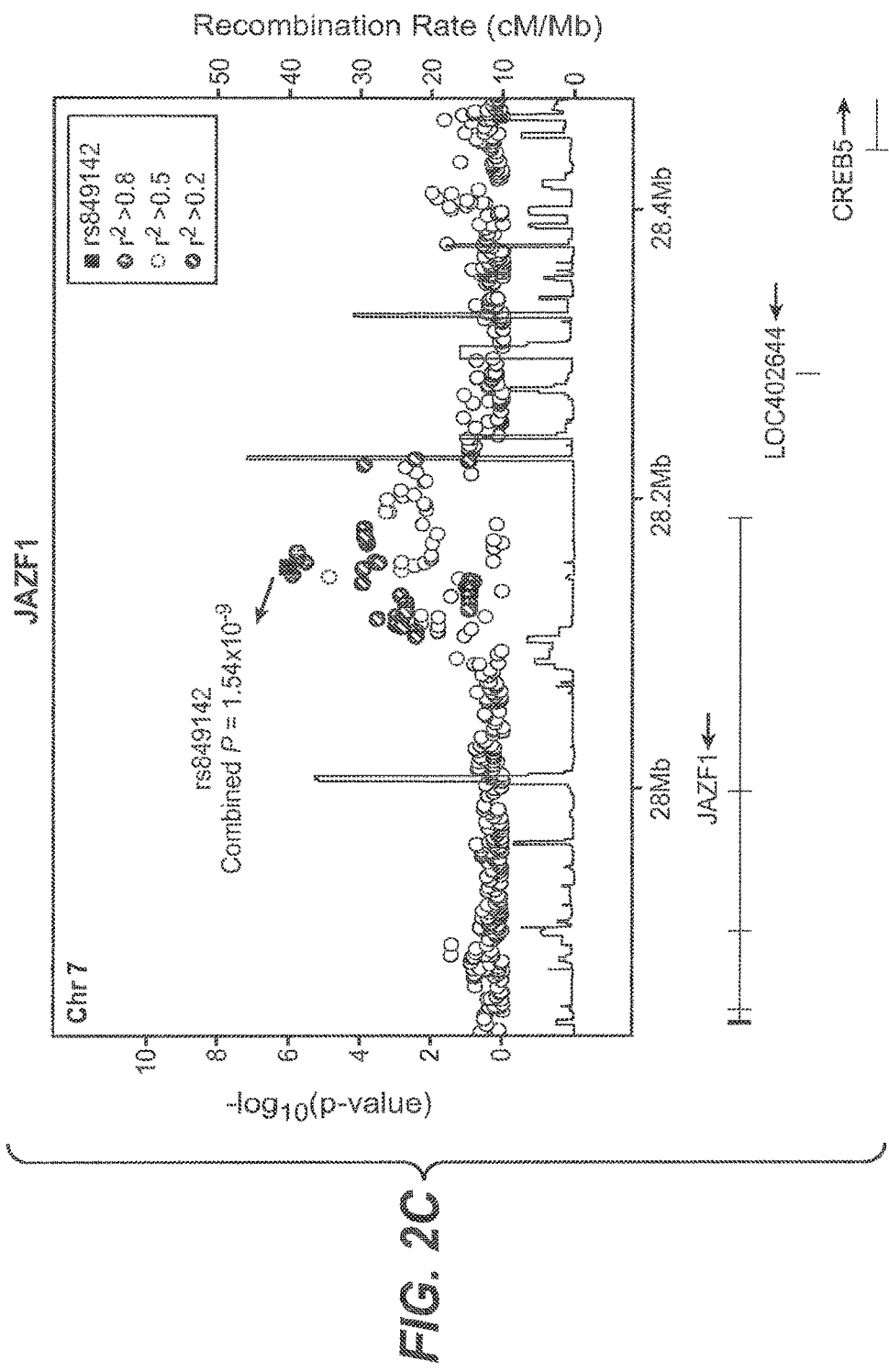
Figure 2D:
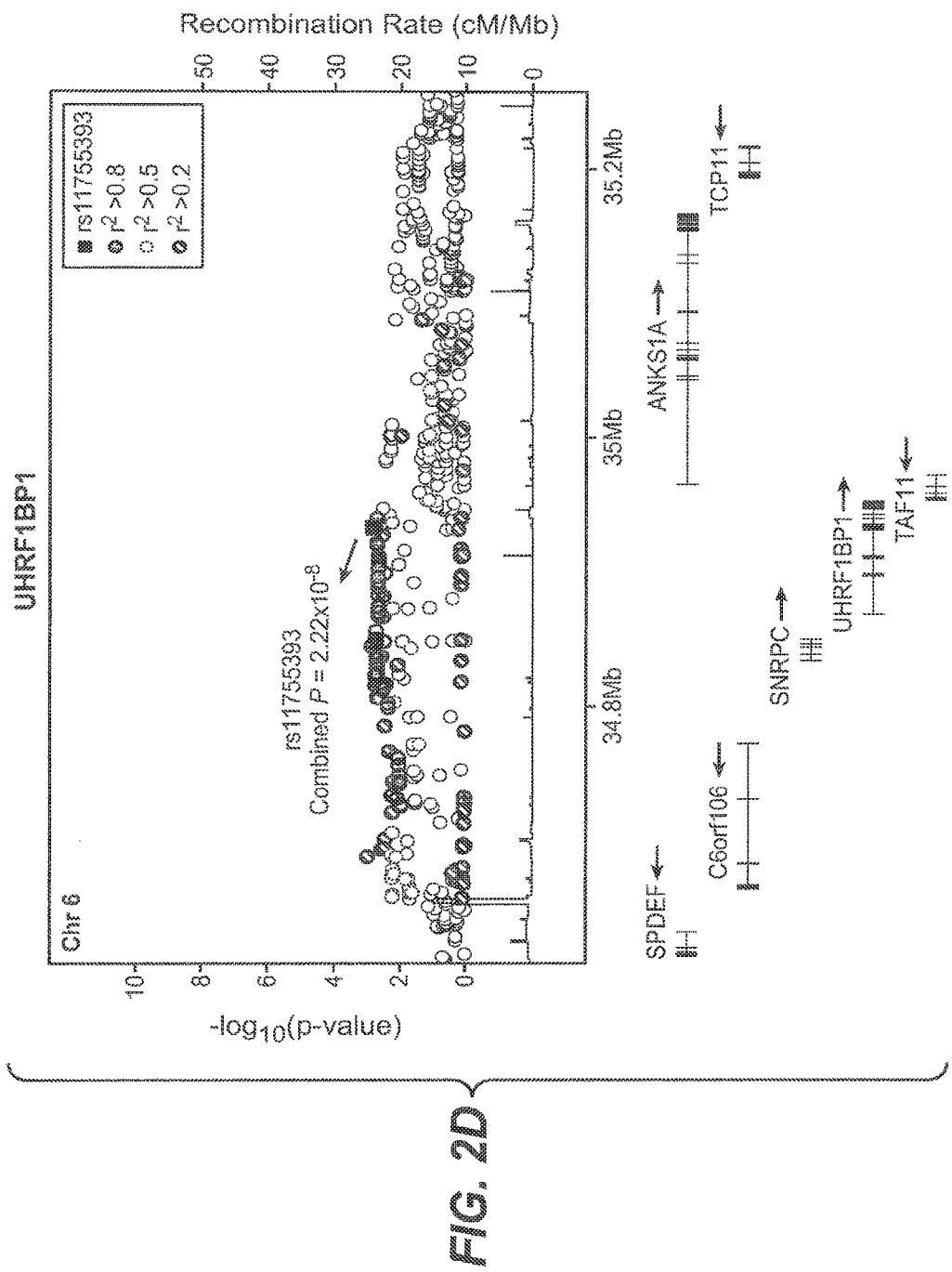
Figure 2E:
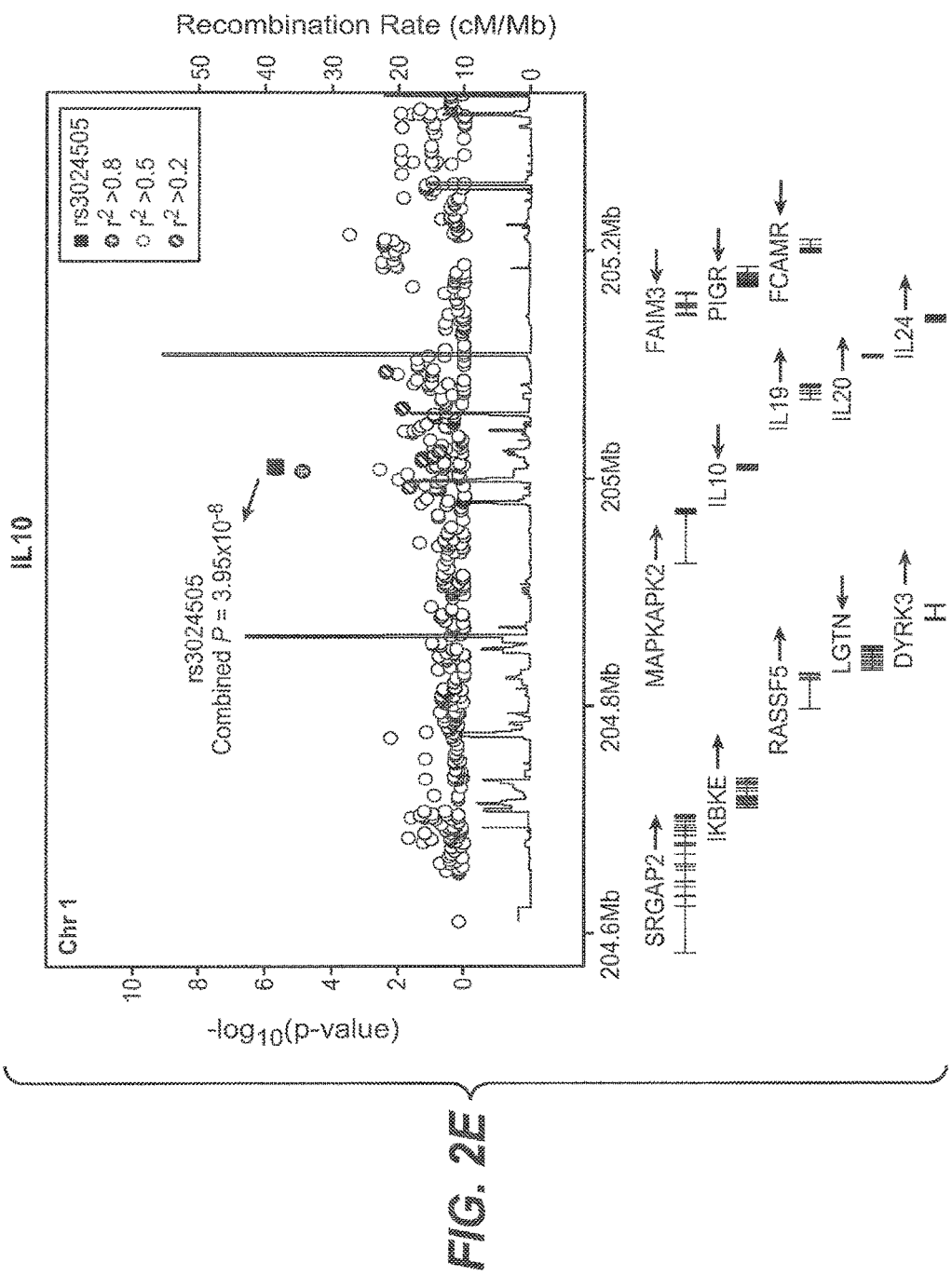
Figure 2F:
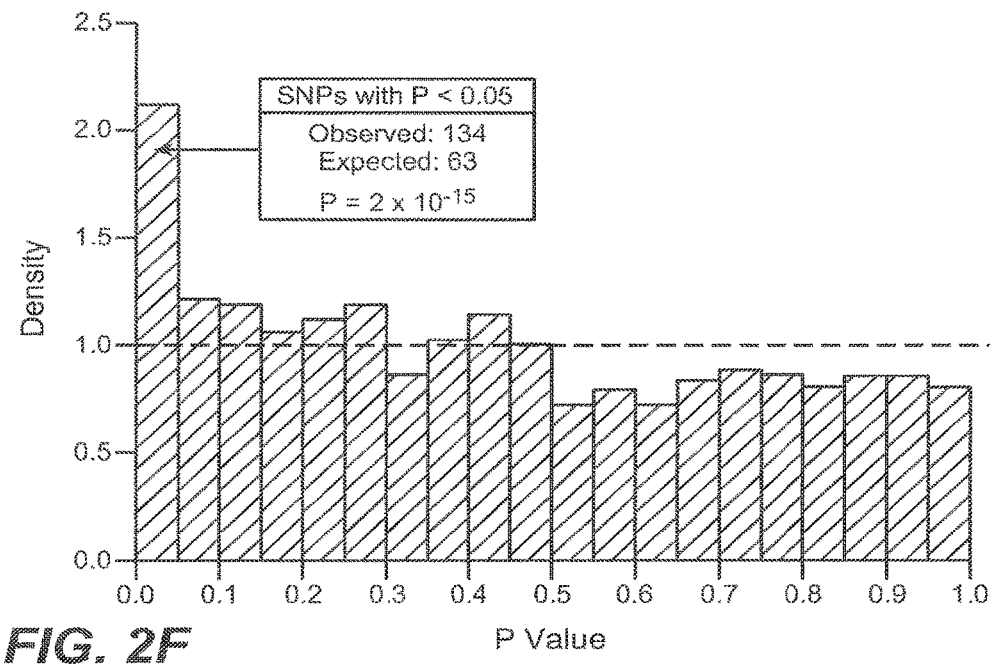

Each of FIGS. 2A-2E show the association results from the genome-wide association scan plotted on the y axis versus genomic position on the x axis within a 500 kb region surrounding the loci defined by TNIP1 (FIG. 2A), PRDM1 (FIG. 2B), JAZF1 (FIG. 2C), UHRF1BP1 (FIG. 2D), and IL-10 (FIG. 2E). The meta-analysis P value for the most associated marker is indicated by a filled square in each of FIGS. 2A-2E. For each of FIGS. 2A-2E, P values from the genome scan are marked to indicate LD to the genome-wide associated variant: stippled circle signifies $r^2>0.8$; dashed circle, $r^2>0.5$; striped circle, $r^2>0.2$; and open circle, $r^2<0.2$. Along the bottom of each of FIGS. 2A-2E, the recombination rate from the CEU HapMap (solid black line) and the known human genes indicated under each plot. In FIG. 2B (PRDM1), a previously reported and independent SLE risk locus at the nearby ATG5 gene is indicated (rs2245214) by the solid black circle. FIG. 2F shows a histogram of the P values of 1256 independent SNPs ($r^2<0.1$ to any other SNP in the array) in the 1,963 case and 4,329 control replication samples. Under a null distribution, the expected density of results is indicated by the dashed line in FIG. 2F. As indicated in FIG. 2F, a significant enrichment of results less than $P<0.05$ was observed.

Accordingly, the replication study identified 5 novel SLE risk loci with a combined P value that exceeded the genome-wide threshold for significance ($P<5\times10^{-8}$); TNIP1, PRDM1, JAZF1, UHRF1BP1, and IL10. Detailed statistical associations for these and other loci are shown below in Table 4.

A variant, rs7708392, on 5q33.1 that resides within an intron of TNF-Alpha Induced Protein 3 (TNFAIP3)-Interacting Protein 1 (TNIP1) was significantly associated with SLE in all three cohorts and had a combined $P=3.8\times10^{-13}$ (FIG. 2A). Variants near TNIP1 were recently found to contribute to risk of psoriasis (Nair, R. P. et al., Nat Genet 41:199-204 (2009)), however the SLE and psoriasis variants are separated by 21 Kb and appear to be distinct genetic signals ($r^2=0.001$). TNIP1 and TNFAIP3 are interacting proteins (Heyninck, K., et al., FEBS Lett 536:135-40 (2003)), however, the precise role of TNIP1 in regulating TNFAIP3 is unknown. The association of multiple distinct variants near TNFAIP3 with SLE (Graham, R. R. et al., Nat. Genet. 40(9):1059-61 (2008), Musone, S. L. et al., Nat. Genet. 40(9):1062-64 (2008)), rheumatoid arthritis (Plenge, R. M. et al., Nat Genet 39:1477-82 (2007)), psoriasis (Nair, R. P. et al., Nat Genet 41:199-204 (2009)) and type I diabetes (Fung, E. Y. et al., Genes Immun 10:188-91 (2009)) suggests this pathway has an important role in the regulation of autoimmunity.

A second confirmed risk variant (rs6568431, $P=7.12\times10^{-10}$ was identified in an intergenic region between PR Domain containing 1, with ZNF domain (PRDM1, also known as BLIMP1) and APG5 autophagy 5-like (ATG5). The signal at rs6568431 appears to be distinct from the previously reported SLE risk allele within ATG5, rs224521.4 (Harley, J. B. et al., Nat Genet 40:204-10 (2008)) (see Table 4), as rs6568431 has an $r^2<0.1$ with rs2245214, and rs2245214 remains significantly associated with SLE ($P<1\times10^{-5}$) after conditional logistic regression incorporating rs6568431 (FIG. 2B).

The promoter region of Juxtaposed with Another Zinc Finger gene 1 (JAZF1) is a third new confirmed SLE locus (rs849142, $P=1.54\times10^{-9}$) (FIG. 2C). Of interest, this same variant was previously linked to risk of type-2 diabetes (Zeggini, E. et al., Nat Genet 40:638-45 (2008)) and differences in height (Johansson, A. et al., Hum Mol Genet 18:373-80 (2009)). A separate prostate cancer allele near JAZF1, rs10486567, (Thomas, G. et al., Nat Genet 40:310-5 (2008)) showed no evidence for association in the current study.

A fourth novel risk locus in SLE is defined by a non-synonymous allele (R454Q) of ICBP90 binding protein 1 (UHRFBP1, rs1.1755393, $P=2.22\times10^{-8}$) (FIG. 2D). This allele is a non-conservative amino acid change in a putative binding partner of UHRF1, a transcription and methylation factor linked to multiple pathways (Arita, K., et al., Nature 455:818-21 (2008)). The UHRFBP1 risk allele is in a region of extended linkage disequilibrium which encompasses multiple genes, including small nuclear ribonucleoprotein polypeptide C (SNPRC), part of a RNA processing complex often targeted by SLE autoantibodies.

The fifth novel SLE locus identified is interleukin-10 (IL10; rs3024505, $P=3.95\times10^{-8}$) (FIG. 2E). IL10 is an important immunoregulatory cytokine that functions to downregulate immune responses (Diveu, C., et al., Curr Opin Immunol 20:663-8 (2008)), and variation in IL10 has inconsistently been reported to be associated with SLE (Nath, S. K., et al., Hum Genet 118:225-34 (2005)). The variant associated with SLE is identical to the SNP recently identified as contributing risk to ulcerative colitis (Franke, A. et al., Nat Genet 40:1319-23 (2008)) and type I diabetes (Barrett, J. C. et al., Nature Genetics 41:703-707 (2009)), suggesting the possibility of shared pathophysiology in the IL10 pathway across these disorders.

Using a significance threshold of $P<1\times10^{-5}$ in the combined replication sample, we identified 21 additional SLE candidate risk loci (Table 4). Less than one locus (0.01) with a $P<1\times10^{-5}$ was expected under a null distribution for the meta-analysis ($P=8\times10^{-77}$), suggesting that several of these loci are likely to be true positive loci. Interesting candidate genes in this list include: a) interferon regulatory factor 8 (IRF8), which was implicated in a previous GWAS (Graham, R. R. et al., Nat. Genet. 40(9):1059-61 (2008)) and whose family members IRF5 and IRF7 are within confirmed SLE risk loci; b) TAO kinase 3 (TAOK3), a missense (rs428073, N47S) of a kinase expressed in lymphocytes; c) lysosomal trafficking regulator (LYST), mutations of which cause the Chediak-Higashi syndrome in humans, a complex disorder characterized by a lymphoproliferative disorder;

and d) interleukin 12 receptor, beta 2 (IL12RB2), a locus which includes IL23R and SERPBP1, but appears distinct from the IL23R variants reported in the autoimmune diseases inflammatory bowel disease, psoriasis and ankylosing spondylitis (Duerr, R. H. et al., Science 314:1-461-3 (2006)).

A remarkable feature of recent GWA studies is the large number of overlapping loci shared between different complex diseases (Zhernakova, A., et al., Nat Rev Genet 10:43-55 (2009)). We tested 42 variants from 35 loci that were previously reported as autoimmune disease risk alleles for association with SLE (Tables 6 and 7). No single locus had an unadjusted P value $<5\times10^{-8}$, however, we found an enrichment of associated alleles. From the 35 loci tested (42 total variants), there were five alleles with an unadjusted P<0.0004 (less than one result expected by chance, P=4.4× $10^{-12}$), and with a P<0.05 after a Bonferroni correction for the 35 pre-specified loci. For each of the five variants, the SLE associated allele matches the previously reported allele and has the same direction of effect (Table 6). We observed a highly significant association of a missense allele of IFIH1 (rs1990760, P=$3.3\times10^{-7}$) that has previously been linked to type I diabetes and Grave's disease (Smyth, D. J. et al., Nat Genet 38:617-9 (2006); Sutherland, A. et al., J Clin Endocrinol Metab 92:3338-41 (2007)). We also observed an association with a missense allele (R32Q) of complement factor B (CFB, rs641153) that resides in the HLA class III region and is a validated risk allele for age-related macular degeneration (Gold, B. et al., Nat Genet 38:458-62 (2006)). The SLE risk allele is not in significant linkage disequilibrium (LD) with other HLA region variants linked to SUE (DR2/DR3) and remained significant after conditional logistic regression analyses that incorporated DR2 and DR3. The HLA is a complex genetic region, but it is striking that the allele of SNP rs641153 has a protective effect nearly identical to the reported AMD risk allele (Gold, B. et al., Nat Genet 38:458-62 (2006)). Further study of the five candidate disease alleles is indicated.

In addition, Table 7 provides detailed summary statistics for the 42 variants identified in other autoimmune diseases. Of interest, variants from CTLA4, IL23R, NOD2 and CD40 that are significant risk factors in other autoimmune diseases appear to show no evidence of association to SLE.

Using 26 SLE risk alleles (21 previously reported loci in Table 2, plus the 5 novel SLE loci described above), several additional analyses were performed. Pair-wise interaction analysis with the confirmed loci was conducted and, consistent with previous literature from SLE (Harley, J. B. et al., Nat Genet 40:204-10 (2008)) and other complex diseases (Barrett, J. C. et al., Nat Genet 40:955-62 (2008)), no evidence for non-additive interactions was observed. Using conditional logistic regression analyses, we found no evidence for multiple independent alleles contributing to risk at any of the individual risk loci. We next estimated the percent of variance explained by each of the confirmed SLE risk alleles, using the methods described by Barrett et al. (Barrett, J. C. et al., Nat Genet 40:955-62 (2008)). HLA-DR3, IRF5 and STAT4 were each estimated to account for >1% of the genetic variance, while the remaining loci each accounted for less than 1% of the variance. Together, the 26 SLE risk loci explain an estimated 8% of the total genetic susceptibility to SLE.

Figure 3:
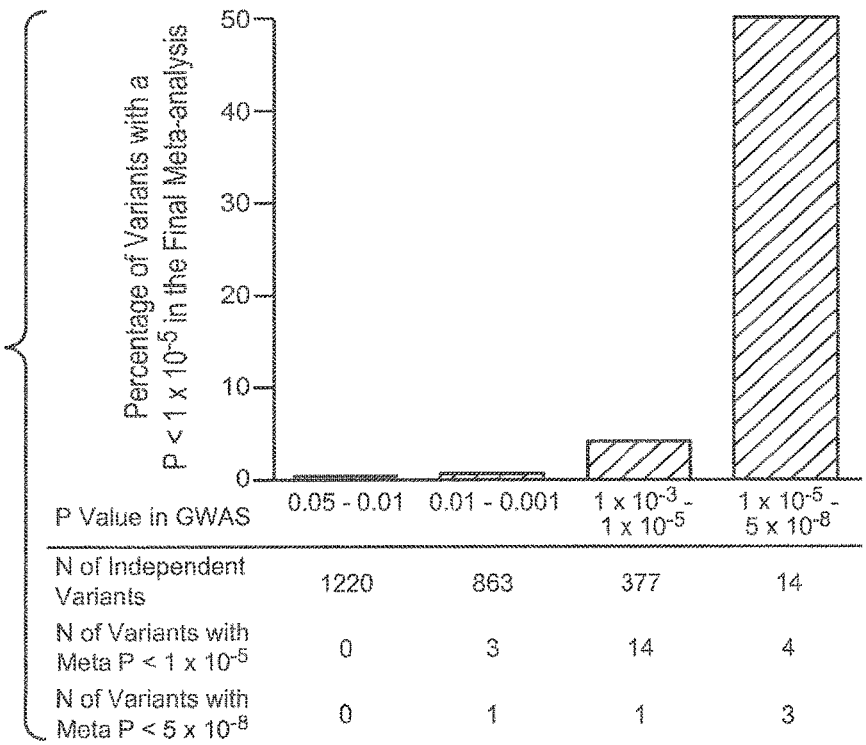
FIG. 3 shows the percentage of variants reaching candidate ($P<1\times10^{-5}$) and confirmed ($P<5\times10^{-8}$) status in the meta-analysis stratified by the P value in the original GWAS as described in Example 1.

Targeted replication of GWAS results is art efficient study design to confirm additional risk loci (Hirschhorn, J. N. et al., Nat Rev Genet 6:95-108 (2005)). There is little available data, however, as to the probability of replicating results that fall short of accepted P value criteria for genome-wide significance. In the current study, all variants with a P<0.05 from the original GWAS studies were included for replication. As shown in FIG. 3, the lower the P value in the GWAS study, the higher the probability of reaching candidate or confirmed status in the replication meta-analysis. Of interest, no candidate or confirmed results were obtained in the current study from the group of variants with a GWAS P between 0.05 and 0.01, despite accounting for ~50% of all variants tested in the replication. These results may be useful in guiding future targeted study designs, although certainly the size of the original GWAS population, the replication sample size, the disease architecture, and the effect size of the candidate variants also need to be carefully considered in planning replication efforts.

These data provide further evidence that common variation in genes important for function of the adaptive and innate arms of the immune system are important in establishing risk for developing SLE. While each of the identified alleles accounts for only a fraction of the overall genetic risk, these and other ongoing studies are providing new insight into the pathogenesis of lupus and are suggesting new targets and pathways for drug discovery and development.

TABLE 2

Replication results of previously reported SLE risk loci

| SNP | Chr | Critical Region | P Values | | | | | Risk | Risk Allele | |
| --- | --- | --- | --- | --- | --- | --- | --- | --- | --- | --- |
| | | | GWAS | US | Sweden | Combined | Locus | Allele | Frequency | OR (95% C.I) |
| Variants with a P < $5 \times 10^{-8}$ in the current dataset | | | | | | | | | | |
| rs3135394[a] | 6p21.32 | 32.027-32.874 | $7.8 \times 10^{-22}$ | $1.8 \times 10^{-26}$ | $8.3 \times 10^{-21}$ | $2.0 \times 10^{-60}$ | HLA-DR3[b] | G | 0.10 | 1.98 (1.84-2.14) |
| rs7574865[a] | 2q32.2 | 191.609-191.681 | $3.0 \times 10^{-19}$ | $6.4 \times 10^{-16}$ | $2.7 \times 10^{-12}$ | $1.4 \times 10^{-41}$ | STAT4 | T | 0.23 | 1.57 (1.49-1.69) |
| rs2070197[a] | 7q32.1 | 128.276-128.476 | n.a. | $1.4 \times 10^{-16}$ | $4.1 \times 10^{-9}$ | $5.8 \times 10^{-24}$ | IRF5 | C | 0.11 | 1.88 (1.78-1.95) |
| rs11860650[a] | 16p11.2 | 31.195-31.277 | $5.3 \times 10^{-11}$ | $1.8 \times 10^{-5}$ | $9.2 \times 10^{-8}$ | $1.9 \times 10^{-20}$ | ITGAM | T | 0.13 | 1.43 (1.32-1.54) |
| rs2736340 | 8p23.1 | 11.331-11.488 | $5.5 \times 10^{-8}$ | $4.6 \times 10^{-9}$ | 0.0028 | $7.9 \times 10^{-17}$ | BLK | T | 0.25 | 1.35 (1.27-1.43) |
| rs5029937[a] | 6q23.3 | 138.174-138.284 | $1.0 \times 10^{-4}$ | $2.4 \times 10^{-7}$ | $3.1 \times 10^{-5}$ | $5.3 \times 10^{-13}$ | TNFAIP3 | T | 0.03 | 1.71 (1.51-1.95) |
| rs2476601 | 1p13.2 | 113.963-114.251 | $3.3 \times 10^{-5}$ | $4.5 \times 10^{-5}$ | $1.5 \times 10^{-5}$ | $3.4 \times 10^{-12}$ | PTPN22 | A | 0.10 | 1.35 (1.24-1.47) |
| rs4963128 | 11p15.5 | 0.485-0.664 | 0.0021 | $1.5 \times 10^{-5}$ | $8.7 \times 10^{-4}$ | $4.9 \times 10^{-9}$ | PHRF1 | C | 0.67 | 1.20 (1.13-1.27) |
| rs2205960 | 1q25.1 | 171.454-171.523 | $9.5 \times 10^{-6}$ | 0.030 | $6.7 \times 10^{-4}$ | $6.3 \times 10^{-9}$ | TNFSF4 | T | 0.23 | 1.22 (1.15-1.30) |
| Variants with a previous report of P < $5 \times 10^{-8}$ | | | | | | | | | | |
| rs9271366[a] | 6p21.32 | 32.446-32.695 | 0.0079 | $7.4 \times 10^{-4}$ | $8.3 \times 10^{-5}$ | $1.4 \times 10^{-7}$ | HLA-DR2[c] | G | 0.16 | 1.26 (1.18-1.36) |
| rs6920220[a] | 6q23.3 | 138.000-138.048 | $9.9 \times 10^{-4}$ | $5.2 \times 10^{-4}$ | 0.049 | $4.0 \times 10^{-7}$ | TNFAIP3 | A | 0.21 | 1.17 (1.10-1.25) |
| rs2269368 | Xq28 | 152.743-152.943 | $2.5 \times 10^{-5}$ | n.a. | 0.0049 | $7.5 \times 10^{-7}$ | IRAK1/MECP2 | T | 0.14 | 1.11 (1.01-1.22) |
| rs2431099 | 5q33.3 | 159.813-159.821 | $1.5 \times 10^{-5}$ | 0.16 | 0.047 | $1.6 \times 10^{-6}$ | PTTG1 | G | 0.52 | 1.15 (1.09-1.22) |

TABLE 2-continued

Replication results of previously reported SLE risk loci

| SNP | Chr | Critical Region | P Values GWAS | P Values US | P Values Sweden | P Values Combined | Locus | Risk Allele | Risk Allele Frequency | OR (95% C.I) |
|---|---|---|---|---|---|---|---|---|---|---|
| rs5754217 | 22q11.2 | 20.240-20.315 | 0.0060 | $8.4 \times 10^{-4}$ | 0.018 | $2.3 \times 10^{-6}$ | UBE2L3 | T | 0.19 | 1.20 (1.13-1.27) |
| rs2245214[a] | 6q21 | 106.749-106.876 | 0.032 | $4.3 \times 10^{-6}$ | 0.35 | $1.2 \times 10^{-5}$ | ATG5 | G | 0.37 | 1.15 (1.09-1.21) |
| rs10516487 | 4q24 | 102.930-103.134 | 0.097 | 0.091 | 0.0015 | $8.3 \times 10^{-4}$ | BANK1 | G | 0.70 | 1.11 (1.04-1.19) |
| rs2176082[a] | 3p14.3 | 58.214-58.443 | 0.010 | 0.012 | 0.0031 | $1.2 \times 10^{-5}$ | PXK | A | 0.28 | 1.17 (1.10-1.25) |
| rs1801274 | 1q23.3 | 159.724-159.746 | $4.1 \times 10^{-4}$ | n.a. | n.a. | $4.1 \times 10^{-4}$ | FCGR2A | G | 0.50 | 1.16 (1.09-1.20) |
| Variants with a previous report of $> 5 \times 10^{-8}$ ||||||||||||
| rs280519[a] | 19p13.2 | 10.387-10.430 | $7.1 \times 10^{-4}$ | n.a. | 0.036 | $7.4 \times 10^{-5}$ | TYK2 | A | 0.48 | 1.13 (1.06-1.21) |
| rs10156091 | 7p21.3 | 8.134-8.154 | 0.095 | 0.0031 | $8.7 \times 10^{-4}$ | $6.5 \times 10^{-4}$ | ICA1 | T | 0.10 | 1.16 (1.06-1.27) |
| rs2022013 | 1q25.3 | 181.538-181.670 | 0.26 | $2.05 \times 10^{-5}$ | $2.8 \times 10^{-4}$ | 0.0015 | NMNAT2 | T | 0.60 | 1.09 (1.03-1.16) |
| rs7829816 | 8q12.1 | 56.985-57.025 | 0.49 | 0.76 | 0.19 | 0.17 | LYN | A | 0.79 | 1.05 (0.96-1.17) |
| rs2071725 | 22q13.2 | 41.908-41.970 | 0.63 | 0.34 | 0.29 | 0.30 | SCUBE1 | G | 0.86 | 1.09 (0.98-1.20) |
| rs5744168[a] | 1q41 | n.a. | n.a. | 1.00 | 0.40 | 0.67 | TLR5 | G | 0.94 | 1.02 (0.94-1.12) |
| rs509749 | 1q23.3 | 158.993-159.067 | 0.64 | 0.94 | 0.93 | 0.76 | LY9 | G | 0.96 | 1.01 (0.91-1.12) |

Critical Region here is defined as the minimal region containing variants with $r^2 > 0.4$ in the HapMap CEU population and is reported in HG18 coordinates (Mb). P values calculated from indicated case/control population (GWAS: 1310 case and 7859 control, U.S.: 1129 case and 2991 control, Sweden 834 case and 1338 control, Combined: 3273 case and 12,188 control samples), and Combined P value calculated as described in methods. Risk Allele is reported relative to + reference strand. Risk Allele Frequency is the frequency in control chromosomes. Odds ratio is the combined odds ratio as described in Methods above.
[a]Indicates markers that were imputed, as described in Methods, in the GWAS samples and directly genotyped in the replication samples.
[b]rs3135394 has an $r^2 = 0.87$ to the HLA*DR3 (DRBP*0301) allele.
[c]rs9271366 has an $r^2 = 0.97$ to the HLA*DR2 (DRB1*1501) allele. See Table 3 for expanded summary statistics.
N.A. = Not available; due to failure to pass QC measures (TYK2, FCGR2A, and IRAK1/MECP2), or the specific variant was not present in the genome-wide array (TLR5 and IRF5). However, rs2070197 (IRF5 region) is in strong linkage disequilibrium (LD) with rs10488631, which had a P = $2 \times 10^{-11}$ in the genome scan.

TABLE 3

Allele frequencies in replication study of previously reported SLE risk loci.

| SNP | Chr | Critical Region | Locus | A1/A2 | GWAS OR | GWAS Controls | GWAS Cases | US OR | US Controls | US Cases | Sweden OR | Sweden Controls | Sweden Cases |
|---|---|---|---|---|---|---|---|---|---|---|---|---|---|
| rs3135394 | 6p21.32 | 32.027-32.874 | HLA-DR3 | G/A | 1.89 | 0.102 | 0.166 | 2.33 | 0.090 | 0.188 | 2.27 | 0.135 | 0.239 |
| rs7574865 | 2q32.2 | 191.609-191.681 | STAT4 | T/G | 1.57 | 0.233 | 0.314 | 1.54 | 0.217 | 0.300 | 2.03 | 0.208 | 0.347 |
| rs2070197 | 7q32.1 | 128.276-128.476 | IRF5 | C/T | n.a. | n.a. | n.a. | 1.62 | 0.105 | 0.176 | 2.08 | 0.125 | 0.226 |
| rs11860650 | 16p11.2 | 31.195-31.277 | ITGAM | T/C | 1.50 | 0.130 | 0.177 | 1.27 | 0.142 | 0.175 | 1.64 | 0.112 | 0.178 |
| rs2736340 | 8p23.1 | 11.331-11.488 | BLK | T/C | 1.31 | 0.246 | 0.299 | 1.47 | 0.236 | 0.313 | 1.25 | 0.262 | 0.307 |
| rs5029937 | 6q23.3 | 138.174-138.284 | TNFAIP3 | T/G | 1.57 | 0.034 | 0.051 | 1.84 | 0.033 | 0.059 | 1.88 | 0.034 | 0.065 |
| rs2476601 | 1p13.2 | 113.963-114.251 | PTPN22 | A/G | 1.35 | 0.098 | 0.116 | 1.48 | 0.083 | 0.119 | 1.47 | 0.120 | 0.167 |
| rs2245214 | 6q21 | 106.749-106.876 | ATG5 | G/C | 1.10 | 0.370 | 0.393 | 1.31 | 0.353 | 0.416 | 1.05 | 0.407 | 0.420 |
| rs4963128 | 11p15.5 | 0.485-0.664 | PHRF1 | C/T | 1.16 | 0.673 | 0.698 | 1.28 | 0.660 | 0.712 | 1.27 | 0.685 | 0.734 |
| rs2205960 | 1q25.1 | 171.454-171.523 | TNFSF4 | T/G | 1.25 | 0.230 | 0.269 | 1.18 | 0.225 | 0.255 | 1.28 | 0.233 | 0.280 |
| rs9271366 | 6p21.32 | 32.446-32.695 | HLA-DR2 | G/A | 1.16 | 0.172 | 0.192 | 1.41 | 0.142 | 0.188 | 1.39 | 0.157 | 0.204 |
| rs6920220 | 6q23.3 | 138.000-138.048 | TNFAIP3 | A/G | 1.19 | 0.206 | 0.234 | 1.28 | 0.190 | 0.231 | 1.16 | 0.232 | 0.257 |
| rs2269368 | Xq28 | 152.743-152.943 | IRAK1/MECP2 | T/C | 1.29 | 0.141 | 0.175 | n.a. | n.a. | n.a. | n.a. | n.a. | n.a. |
| rs2431099 | 5q33.3 | 159.813-159.821 | PTTG1 | G/A | 1.20 | 0.522 | 0.568 | 1.09 | 0.515 | 0.536 | 1.14 | 0.541 | 0.578 |
| rs5754217 | 22q11.2 | 20.240-20.315 | UBE2L3 | T/G | 1.16 | 0.188 | 0.213 | 1.23 | 0.191 | 0.225 | 1.22 | 0.231 | 0.268 |
| rs2176082 | 3p14.3 | 58.214-58.443 | PXK | A/G | 1.13 | 0.284 | 0.309 | 1.21 | 0.274 | 0.314 | 1.22 | 0.308 | 0.351 |
| rs280519 | 19p13.2 | 10.387-10.430 | TYK2 | A/G | 1.16 | 0.477 | 0.507 | n.a. | n.a. | n.a. | 1.15 | 0.476 | 0.511 |
| rs1801274 | 1q23.3 | 159.724-159.746 | FCGR2A | G/A | 1.16 | 0.500 | 0.537 | n.a. | n.a | n.a | n.a. | n.a. | n.a. |
| rs10156091 | 7p21.3 | 8.134-8.154 | ICA1 | T/C | 1.12 | 0.098 | 0.104 | 1.26 | 0.105 | 0.129 | 1.19 | 0.095 | 0.110 |
| rs10516487 | 4q24 | 102.930-103.134 | BANK1 | G/A | 1.08 | 0.694 | 0.712 | 1.10 | 0.698 | 0.716 | 1.20 | 0.722 | 0.758 |
| rs2022013 | 1q25.3 | 181.538-181.670 | NMNAT2 | T/C | 1.05 | 0.599 | 0.609 | 1.22 | 0.580 | 0.627 | 1.04 | 0.618 | 0.627 |
| rs7829816 | 8q12.1 | 56.985-57.025 | LYN | A/G | 1.04 | 0.786 | 0.795 | 1.03 | 0.783 | 0.789 | 1.07 | 0.817 | 0.827 |
| rs2071725 | 22g13.2 | 41.908-41.970 | SCUBE1 | G/A | 1.03 | 0.859 | 0.870 | 1.12 | 0.859 | 0.873 | 1.01 | 0.887 | 0.889 |
| rs5744168 | 1 | n.a. | TLR5 | G/A | n.a. | n.a. | n.a. | 0.93 | 0.947 | 0.943 | 1.19 | 0.920 | 0.932 |
| rs509749 | 1q23.3 | 158.993-159.067 | LY9 | G/A | 1.02 | 0.425 | 0.428 | 1.00 | 0.429 | 0.430 | 0.99 | 0.453 | 0.451 |

Critical Region here is defined as the minimal region containing variants with $r^2 > 0.4$ in the HapMap CEU population and is reported in HG18 coordinates. Allele frequencies calculated from indicated case/control population (GWAS: 1310 case and 7859 control, US: 1129 case and 2991 control, Sweden 834 case and 1338 control, Combined: 3273 case and 12188 control samples). Alleles are reported relative to + reference strand, and all data refers to Allele 1 (A1). The odds ratio (OR) for each population is listed.

TABLE 4

Novel SLE risk loci in the combined dataset.

| SNP | Chr. | Critical Region | P values GWAS | P values US | P values Sweden | P values Combined | Locus | Risk Allele | Risk Allele Frequency | OR (95% C.I.) |
|---|---|---|---|---|---|---|---|---|---|---|
| | | | Genome-wide significant loci | | | | | | | |
| rs7708392[a] | 5 | 150.419-150.441 | $4.5 \times 10^{-7}$ | $7.7 \times 10^{-4}$ | $1.2 \times 10^{-5}$ | $3.8 \times 10^{-13}$ | TNIP1 | C | 0.24 | 1.27 (1.10-1.35) |
| rs6568431 | 6 | 106.675-106.705 | $6.1 \times 10^{-6}$ | 0.0016 | 0.0050 | $7.1 \times 10^{-10}$ | PRDM1 | A | 0.38 | 1.20 (1.14-1.27) |
| rs849142[a] | 7 | 28.108-28.223 | $4.5 \times 10^{-7}$ | 0.10 | $5.4 \times 10^{-4}$ | $1.5 \times 10^{-9}$ | JAZF1 | T | 0.49 | 1.19 (1.13-1.26) |
| rs11755393[a] | 6 | 34.658-35.090 | 0.0014 | $3.7 \times 10^{-4}$ | $5.1 \times 10^{-4}$ | $2.2 \times 10^{-8}$ | UHRF1BP1 | G | 0.35 | 1.17 (1.10-1,24) |
| rs3024505 | 1 | 205.007-205.016 | $2.6 \times 10^{-6}$ | 0.062 | $1.8 \times 10^{-4}$ | $4.0 \times 10^{-8}$ | IL10 | A | 0.16 | 1.19 (1.11-1.28) |
| | | | Loci with combined P value $< 1 \times 10^{-6}$ | | | | | | | |
| rs10911363[a] | 1 | 181.672-181.816 | $2.0 \times 10^{-4}$ | $1.5 \times 10^{-5}$ | 0.52 | $9.5 \times 10^{-8}$ | NCF2 | T | 0.27 | 1.19 (1.12-1.26) |
| rs12444486[a] | 16 | 84.548-84.576 | $3.5 \times 10^{-5}$ | 0.021 | 0.026 | $1.9 \times 10^{-7}$ | IRF8 | T | 0.50 | 1.16 (1.10-1.23) |
| rs11013210[a] | 10 | 23.181-23.337 | $1.6 \times 10^{-5}$ | 0.013 | 0.12 | $2.0 \times 10^{-7}$ | ARMC3 | T | 0.21 | 1.18 (1.11-1.26) |
| rs1874791[a] | 1 | 67.563-67.687 | $3.1 \times 10^{-5}$ | 0.012 | 0.11 | $3.4 \times 10^{-7}$ | IL12RB2 | A | 0.18 | 1.18 (1.10-1.26) |
| rs9782955 | 1 | 233.893-234.107 | $6.4 \times 10^{-6}$ | 0.057 | 0.12 | $4.6 \times 10^{-7}$ | LYST | C | 0.74 | 1.18 (1.11-1.26) |
| rs7683537[a] | 4 | 185.805-185.914 | $1.6 \times 10^{-4}$ | 0.11 | 0.0013 | $7.6 \times 10^{-7}$ | MLF1IP | T | 0.82 | 1.23 (1.14-1.33) |
| rs428073 | 12 | 117.706-117.315 | $1.7 \times 10^{-5}$ | 0.22 | 0.0079 | $7.7 \times 10^{-7}$ | TAOK3 | T | 0.69 | 1.18 (1.11-1.26) |
| rs497273[a] | 12 | 119.610-119.891 | $5.0 \times 10^{-5}$ | 0.068 | 0.021 | $8.2 \times 10^{-7}$ | SPPL3 | G | 0.65 | 1.14 (1.08-1.21) |
| | | | Loci with combined P value $< 1 \times 10^{-5}$ | | | | | | | |
| rs1861525 | 7 | 25.097-25.183 | $8.5 \times 10^{-5}$ | 0.16 | 0.0027 | $1.9 \times 10^{-6}$ | CYCS | G | 0.05 | 1.27 (1.12-1.45) |
| rs921916 | 7 | 50.193-50.205 | $4.8 \times 10^{-4}$ | 0.027 | 0.014 | $2.0 \times 10^{-6}$ | IKZF1 | C | 0.18 | 1.15 (1.07-1.23) |
| rs7333671 | 13 | 73.177-73.198 | $2.2 \times 10^{-4}$ | 0.14 | 0.0027 | $2.2 \times 10^{-6}$ | KLF12 | G | 0.08 | 1.22 (1.11-1.34) |
| rs12992463 | 2 | 22.312-22.464 | $2.1 \times 10^{-5}$ | 0.23 | 0.023 | $2.6 \times 10^{-6}$ | — | A | 0.50 | 1.12 (1.06-1.19) |
| rs12620999 | 2 | 237.616-237.770 | $1.6 \times 10^{-5}$ | 0.040 | 0.45 | $3.1 \times 10^{-6}$ | COPS8 | C | 0.19 | 1.13 (1.06-1.21) |
| rs503425[a] | 11 | 118.079-118.198 | 0.0012 | $3.3 \times 10^{-4}$ | 0.43 | $3.3 \times 10^{-6}$ | DDX6 | C | 0.20 | 1.16 (1.08-1.24) |
| rs10742326[a] | 11 | 34.733-34.809 | $1.4 \times 10^{-4}$ | 0.017 | 0.21 | $3.6 \times 10^{-6}$ | APIP | G | 0.59 | 1.14 (1.08-1.21) |
| rs4766921[a] | 12 | 117.835-117.883 | $4.6 \times 10^{-5}$ | n.a. | 0.036 | $4.6 \times 10^{-6}$ | KIAA1853 | G | 0.67 | 1.18 (1.09-1.27) |
| rs11951576[a] | 5 | 6.741-6.866 | $2.5 \times 10^{-5}$ | 0.42 | 0.014 | $4.6 \times 10^{-6}$ | POLS/SRD5A | C | 0.69 | 1.14 (1.08-1.22) |
| rs6438700 | 3 | 123.355-123.454 | $7.4 \times 10^{-5}$ | 0.23 | 0.020 | $5.5 \times 10^{-6}$ | CD86 | C | 0.82 | 1.18 (1.09-1.27) |
| rs6486730[a] | 12 | 127.830-127.840 | $8.2 \times 10^{-5}$ | 0.16 | 0.049 | $6.9 \times 10^{-6}$ | SLC15A4 | G | 0.41 | 1.13 (1.07-1.19) |
| rs4748857[a] | 10 | 23.529-23.654 | $2.2 \times 10^{-4}$ | 0.68 | $1.3 \times 10^{-4}$ | $6.9 \times 10^{-6}$ | C10orf67 | C | 0.73 | 1.16 (1.09-1.24) |
| rs3914167[a] | 5 | 39.426-39.454 | $1.8 \times 10^{-4}$ | 0.24 | 0.0081 | $7.6 \times 10^{-6}$ | DAB2/C9 | G | 0.27 | 1.15 (1.09-1.23) |

Samples, critical region, P values, risk alleles, and odds ratios are as defined in the Table 2 legend.
[a] Indicates markers that were imputed, as described in Methods above, from the GWAS samples and directly genotyped in the replication samples. See Table 5 for expanded summary statistics.

TABLE 5

Additional summary statistics for significant SLE risk loci in the combined dataset.

| SNP | Chr | Critical Region | Locus | A1/A2 | GWAS OR | GWAS Controls | GWAS Cases | US OR | US Controls | US Cases | Sweden OR | Sweden Controls | Sweden Cases |
|---|---|---|---|---|---|---|---|---|---|---|---|---|---|
| rs7708392 | 5 | 150.419-150.441 | TNIP1 | C/G | 1.28 | 0.232 | 0.279 | 1.19 | 0.267 | 0.302 | 1.37 | 0.256 | 0.324 |
| rs6568431 | 6 | 106.675-106.705 | PRDM1 | A/C | 1.22 | 0.380 | 0.424 | 1.22 | 0.370 | 0.418 | 1.18 | 0.412 | 0.451 |
| rs849142 | 7 | 28.108-28.223 | JAZFI | T/C | 1.23 | 0.490 | 0.542 | 1.11 | 0.491 | 0.516 | 1.25 | 0.499 | 0.552 |
| rs11755393 | 6 | 34.658-35.090 | UHRF1BP1 | G/A | 1.15 | 0.354 | 0.386 | 1.15 | 0.347 | 0.380 | 1.27 | 0.326 | 0.376 |
| rs3024505 | 1 | 205.007-205.016 | IL10 | A/G | 1.28 | 0.166 | 0.196 | 1.14 | 0.152 | 0.169 | 1.21 | 0.150 | 0.176 |
| rs10911363 | 1 | 181.672-181.816 | NCF2 | T/G | 1.21 | 0.274 | 0.307 | 1.27 | 0.273 | 0.323 | 1.05 | 0.275 | 0.293 |
| rs12444486 | 16 | 84.548-84.576 | IRF8 | T/C | 1.19 | 0.507 | 0.550 | 1.11 | 0.501 | 0.528 | 1.15 | 0.482 | 0.526 |
| rs11013210 | 10 | 23.181-23.337 | ARMC3 | T/C | 1.27 | 0.199 | 0.234 | 1.17 | 0.229 | 0.257 | 1.13 | 0.225 | 0.243 |
| rs1874791 | 1 | 67.563-67.687 | IL12RB2 | A/G | 1.25 | 0.183 | 0.225 | 1.09 | 0.188 | 0.202 | 1.15 | 0.146 | 0.163 |
| rs9782955 | 1 | 233.893-234.107 | LYST | C/T | 1.25 | 0.737 | 0.777 | 1.12 | 0.744 | 0.766 | 1.15 | 0.765 | 0.788 |
| rs7683537 | 4 | 185.805-185.914 | MLF1IP | T/C | 1.23 | 0.811 | 0.843 | 1.13 | 0.832 | 0.848 | 1.34 | 0.834 | 0.872 |
| rs428073 | 12 | 117.706-117.315 | TAOK3 | T/C | 1.22 | 0.691 | 0.730 | 1.07 | 0.694 | 0.708 | 1.31 | 0.682 | 0.738 |
| rs497273 | 12 | 119.610-119.891 | SPPL3 | G/C | 1.19 | 0.649 | 0.690 | 1.03 | 0.663 | 0.670 | 1.16 | 0.618 | 0.660 |
| rs1861525 | 7 | 25.097-25.183 | CYCS | G/A | 1.52 | 0.054 | 0.068 | 1.14 | 0.041 | 0.047 | 1.96 | 0.017 | 0.032 |
| rs921916 | 7 | 50.193-50.205 | IKZF1 | C/T | 1.20 | 0.187 | 0.211 | 1.08 | 0.189 | 0.200 | 1.27 | 0.152 | 0.185 |
| rs7333671 | 13 | 73.177-73.198 | KLF12 | G/A | 1.32 | 0.085 | 0.107 | 1.08 | 0.082 | 0.088 | 1.35 | 0.066 | 0.087 |
| rs12992463 | 2 | 22.312-22.464 | LOC645949 | A/C | 1.20 | 0.499 | 0.538 | 1.04 | 0.510 | 0.521 | 1.15 | 0.495 | 0.531 |
| rs12620999 | 2 | 237.616-237.770 | COPS8 | C/T | 1.27 | 0.190 | 0.217 | 1.12 | 0.180 | 0.198 | 1.03 | 0.185 | 0.190 |
| rs503425 | 11 | 118.079-118.198 | DDX6 | C/T | 1.18 | 0.206 | 0.233 | 1.20 | 0.194 | 0.224 | 1.06 | 0.198 | 0.206 |
| rs10742326 | 11 | 34.733-34.809 | APIP | G/A | 1.18 | 0.585 | 0.625 | 1.11 | 0.591 | 0.617 | 1.09 | 0.577 | 0.601 |
| rs4766921 | 12 | 117.835-117.883 | KIAA1853 | G/A | 1.22 | 0.668 | 0.707 | n.a. | n.a. | n.a. | 1.15 | 0.662 | 0.689 |
| rs11951576 | 5 | 6.741-6.866 | POLS/SRD5A | C/T | 1.22 | 0.686 | 0.727 | 1.04 | 0.691 | 0.700 | 1.19 | 0.669 | 0.701 |

TABLE 5-continued

Additional summary statistics for significant SLE risk loci in the combined dataset.

| | | | | | GWAS | | | US | | | Sweden | | |
| | | | | | | Allele Frequency | | | Allele Frequency | | | Allele Frequency | |
| SNP | Chr | Critical Region | Locus | A1/A2 | OR | Controls | Cases | OR | Controls | Cases | OR | Controls | Cases |
|---|---|---|---|---|---|---|---|---|---|---|---|---|---|
| rs6438700 | 3 | 123.355-123.454 | CD86 | C/T | 1.25 | 0.823 | 0.854 | 1.05 | 0.826 | 0.834 | 1.23 | 0.821 | 0.851 |
| rs6486730 | 12 | 127.830-127.840 | SLC15A4 | G/A | 1.19 | 0.405 | 0.446 | 1.06 | 0.420 | 0.436 | 1.14 | 0.422 | 0.450 |
| rs4748857 | 10 | 23.529-23.654 | C10orf67 | C/T | 1.22 | 0.715 | 0.741 | 1.10 | 0.763 | 0.780 | 1.35 | 0.742 | 0.791 |
| rs3914167 | 5 | 39.426-39.454 | DAB2/C9 | G/C | 1.19 | 0.274 | 0.312 | 1.08 | 0.276 | 0.291 | 1.20 | 0.262 | 0.294 |

Critical Region here is defined as the minimal region containing variants with $r^2 > 0.4$ in the HapMap CEU population and is reported in HG18 coordinates. Allele frequencies calculated from indicated case/control population (GWAS: 1310 case and 7859 control, US: 1129 case and 2991 control, Sweden 834 case and 1338 control, Combined: 3273 case and 12,188 control samples). Alleles are reported relative to + reference strand, and all data refers to Allele 1 (A1). The odds ratio (OR) for each population is listed.

TABLE 6

Candidate autoimmune loci with evidence of association to SLE.

| | | | P Values | | | | | | | | |
| SNP | Locus | Chr | GWAS | US | Sweden | Combined | Combined Corrected | Risk Allele | Risk Allele Frequency | OR | Phenotype | References |
|---|---|---|---|---|---|---|---|---|---|---|---|---|
| rs1990760 | IFIH1 | 2 | $3.2 \times 10^{-5}$ | 0.015 | 0.0039 | $3.34 \times 10^{-7}$ | $1.12 \times 10^{-5}$ | T | 0.60 | 1.17 | T1D, Grave's | Nat Genet 38:617-9 (2006); J Clin Endocrinol Metab 92:333841 (2007) |
| rs641153[a] | CFB | 6 | 0.0079 | n.a. | 0.0011 | $1.4 \times 10^{-4}$ | 0.0049 | G | 0.91 | 1.30 | AMD | Nat Genet 33:458-62 (2006) |
| rs12708716[a] | CLEC16A | 16 | 0.15 | $1.3 \times 10^{-4}$ | 0.062 | $1.6 \times 10^{-4}$ | 0.0056 | A | 0.64 | 1.16 | T1D, Addison's MS | J Clin Endocrinol Metab 94:231-235 (2009); J Clin Endocrinol Metab 93:3310-7 (2008); Genes Immun 10:15-7 (2009) |
| rs6887695[a] | IL12B | 5 | 0.014 | 0.04 | 0.03 | $1.7 \times 10^{-4}$ | 0.0060 | G | 0.68 | 1.13 | PS, IBD | Nat Genet 41:199-204 (2009); Nat Genet 40:710-2 (2008) |
| rs17696736 | SH2B3 | 12 | 0.0036 | 0.12 | 0.19 | $4.0 \times 10^{-4}$ | 0.014 | T | 0.50 | 1.08 | T1D, Celiac, SLE | J Clin Endocrinol Metab 93:3310-7 (2008); Nat Genet 40:395-402 (2008); N Engl J Med 359:2767-77 (2008) |

All alleles in the table were either identical to the reported variants or have $r^2 < 0.8$ to the reported variant and were the same risk allele with the same direction of effect. Position (basepairs) is reported in HG18 coordinates. Samples, individual and combined P values, risk allele frequency and OR are as described in Table 2 legend. Combined-Corrected P value is the Bonferonni corrected P value for the 35 previously reported risk loci. Other autoimmunity associations: T1D = Type I diabetes, AMD = age-related macular degeneration MS = multiple sclerosis IBD = inflammatory bowel disease and PS = psoriasis. See Table 7 for expanded summary statistics and a complete list of variants tested.
[a]Indicates markers that were imputed, as described in Methods, from the GWAS samples and directly genotyped in the replication samples.

TABLE 7

Confirmed autoimmune disease loci.

| | | | | | GWAS | | | | US | | | |
| SNP | Chr. | Position | Locus | A1/A2 | P value | OR | Controls | Cases | P value | OR | Controls | Cases |
|---|---|---|---|---|---|---|---|---|---|---|---|---|
| rs1990760 | 2 | 162832297 | IFIH1 | T/C | $3.2 \times 10^{-4}$ | 1.17 | 0.600 | 0.638 | 0.015 | 1.17 | 0.581 | 0.618 |
| rs641153 | 6 | 32022159 | CFB | G/A | 0.0079 | 1.22 | 0.910 | 0.926 | n.a. | n.a. | n.a. | n.a. |
| rs12708716 | 16 | 11087374 | CLEC16A | A/G | 0.15 | 1.06 | 0.635 | 0.651 | $1.3 \times 10^{-4}$ | 1.29 | 0.616 | 0.674 |
| rs6887695 | 5 | 158755223 | IL128 | G/C | 0.014 | 1.12 | 0.683 | 0.706 | 0.040 | 1.11 | 0.676 | 0.699 |
| rs17696736 | 12 | 110971201 | C12orf30 | G/A | 0.0081 | 1.12 | 0.449 | 0.474 | 0.16 | 1.01 | 0.459 | 0.462 |
| rs3184504 | 12 | 110368991 | SH2B3 | T/C | 0.0036 | 1.13 | 0.503 | 0.530 | 0.12 | 1.04 | 0.499 | 0.508 |
| rs2812378 | 9 | 34700260 | CCL21 | G/A | 0.003 | 1.14 | 0.322 | 0.349 | 0.79 | 1.02 | 0.321 | 0.325 |
| rs3761847 | 9 | 122730060 | TRAF1 | G/A | 0.034 | 1.10 | 0.411 | 0.432 | 0.20 | 1.12 | 0.416 | 0.444 |
| rs6899540 | 6 | 43866302 | VEGFA | C/A | $8.1 \times 10^{-4}$ | 1.22 | 0.172 | 0.196 | 0.90 | 1.00 | 0.166 | 0.166 |
| rs547154 | 6 | 32018917 | C2 | T/G | n.a. | n.a. | n.a. | n.a. | 0.28 | 0.94 | 0.080 | 0.075 |
| rs12044852 | 1 | 116889302 | CD58 | C/A | 0.099 | 1.12 | 0.886 | 0.893 | 0.25 | 1.04 | 0.900 | 0.903 |
| rs2542151 | 18 | 12769947 | PTPN2 | G/T | 0.15 | 1.09 | 0.152 | 0.162 | n.a. | n.a. | n.a. | n.a. |
| rs6897932 | 5 | 35910332 | IL7R | C/T | 0.18 | 1.06 | 0.740 | 0.751 | 0.25 | 1.05 | 0.743 | 0.752 |
| rs2230199 | 19 | 6669387 | C3 | C/G | n.a. | n.a. | n.a. | n.a. | n.a. | n.a. | n.a. | n.a. |
| rs3732378 | 3 | 39282166 | CX3CR1 | G/A | 0.13 | 1.09 | 0.833 | 0.843 | 0.063 | 1.12 | 0.829 | 0.845 |

TABLE 7-continued

Confirmed autoimmune disease loci.

| SNP | Chr. | Position | Locus | A1/A2 | | | | | | | |
|---|---|---|---|---|---|---|---|---|---|---|---|
| rs1678542 | 12 | 56254982 | KIF5A | C/G | 0.051 | 1.09 | 0.624 | 0.642 | 0.94 | 1.00 | 0.626 | 0.625 |
| rs1136287 | 17 | 1620026 | SERPINF1 | T/C | 0.64 | 1.02 | 0.641 | 0.637 | 0.19 | 1.02 | 0.647 | 0.652 |
| rs12247631 | 10 | 52485603 | PRKG1 | A/C | 0.32 | 1.56 | 0.004 | 0.004 | 0.051 | 1.48 | 0.005 | 0.007 |
| rs2227306 | 4 | 74825919 | IL8 | T/C | 0.036 | 1.11 | 0.407 | 0.426 | 0.42 | 0.98 | 0.415 | 0.409 |
| rs12521868 | 5 | 131812292 | LOC441108 | T/G | 0.085 | 1.08 | 0.424 | 0.440 | 0.87 | 0.99 | 0.406 | 0.405 |
| rs10490924 | 10 | 124204438 | ARMS2 | G/T | 0.13 | 1.09 | 0.787 | 0.798 | 0.56 | 1.03 | 0.780 | 0.786 |
| rs1793004 | 11 | 20655505 | NELL1 | G/C | 0.81 | 1.01 | 0.758 | 0.759 | 0.25 | 1.01 | 0.751 | 0.754 |
| rs10225965 | 7 | 92111514 | CDK6 | C/T | 0.033 | 1.12 | 0.802 | 0.817 | 0.61 | 0.91 | 0.820 | 0.805 |
| rs1410996 | 1 | 194963556 | CFH | A/G | 0.08 | 1.08 | 0.414 | 0.429 | 0.48 | 0.94 | 0.427 | 0.412 |
| rs3087243 | 2 | 204447164 | CTLA4 | G/A | 0.30 | 1.04 | 0.567 | 0.580 | 0.86 | 1.04 | 0.549 | 0.559 |
| rs2292239 | 12 | 54768447 | ERBB3 | T/G | 0.72 | 1.02 | 0.329 | 0.329 | 0.11 | 1.10 | 0.330 | 0.351 |
| rs12722489 | 10 | 6142018 | IL2RA | C/T | 0.89 | 1.01 | 0.849 | 0.851 | n.a. | na | n.a. | n.a. |
| rs9332739 | 6 | 32011783 | C2 | C/G | 0.92 | 1.01 | 0.048 | 0.050 | n.a. | n.a. | n.a. | n.a. |
| rs2076756 | 16 | 49314382 | NOD2 | G/A | 0.44 | 1.04 | 0.273 | 0.280 | 0.71 | 1.00 | 0.256 | 0.256 |
| rs16853571 | 4 | 41447887 | PHOX2B | C/A | 0.51 | 1.06 | 0.065 | 0.067 | 0.79 | 0.99 | 0.065 | 0.065 |
| rs4810485 | 20 | 44181354 | CD40 | T/G | 0.37 | 1.04 | 0.264 | 0.274 | n.a. | n.a. | n.a. | n.a. |
| rs9340799 | 6 | 152205074 | ESR1 | A/G | 0.17 | 1.06 | 0.646 | 0.659 | 0.28 | 0.99 | 0.641 | 0.638 |
| rs3793784 | 10 | 50417545 | ERCC6 | C/G | 0.54 | 1.03 | 0.402 | 0.408 | 0.42 | 0.97 | 0.406 | 0.400 |
| rs2240340 | 1 | 17535226 | PADI4 | C/T | 0.64 | 1.02 | 0.579 | 0.585 | 0.13 | 0.93 | 0.590 | 0.574 |
| rs7517847 | 1 | 67454257 | IL23R | T/G | 0.79 | 1.01 | 0.569 | 0.567 | 0.86 | 1.06 | 0.419 | 0.433 |

Variants in LD with above loci

| rs1061170 | 1 | 194925860 | CFH | T/C | n.a. | n.a. | n.a. | n.a. | n.a. | n.a. | n.a. | n.a. |
| rs2234693 | 6 | 152205028 | ESR1 | T/C | n.a. | n.a. | n.a. | n.a. | 0.403 | 0.972 | 0.539 | 0.531 |
| rs1136287 | 17 | 1620026 | SERPINF1 | T/C | 0.642 | 1.021 | 0.641 | 0.637 | 0.190 | 1.023 | 0.647 | 0.652 |
| rs3024997 | 6 | 43853085 | VEGFA | A/G | n.a. | n.a. | n.a. | n.a. | 0.977 | 0.964 | 0.327 | 0.319 |
| rs3212227 | 5 | 158675528 | IL12B | T/G | 0.000 | 1.220 | 0.792 | 0.821 | 0.407 | 1.059 | 0.784 | 0.794 |
| rs2339898 | 10 | 1053379358 | PRKG1 | C/T | 0.626 | 1.022 | 0.338 | 0.347 | 0.190 | 1.051 | 0.338 | 0.349 |
| rs42041 | 7 | 92084680 | CDK6 | G/C | 0.570 | 1.028 | 0.267 | 0.269 | 0.790 | 0.966 | 0.258 | 0.251 |

| | | | | | Sweden | | | | Replication | |
|---|---|---|---|---|---|---|---|---|---|---|
| SNP | Chr. | Position | Locus | A1/A2 | P value | OR | Controls | Cases | P value | Combined P value |
| rs1990760 | 2 | 162832297 | IFIH1 | T/C | 0.0039 | 1.17 | 0.609 | 0.645 | $2.6 \times 10^{-4}$ | $3.3 \times 10^{-7}$ |
| rs641153 | 6 | 32022159 | CFB | G/A | 0.0011 | 1.47 | 0.915 | 0.939 | 0.0011 | $1.4 \times 10^{-4}$ |
| rs12708716 | 16 | 11087374 | CLEC16A | A/G | 0.062 | 1.14 | 0.694 | 0.725 | $2.8 \times 10^{-5}$ | $1.6 \times 10^{-4}$ |
| rs6887695 | 5 | 158755223 | IL12B | G/C | 0.030 | 1.16 | 0.664 | 0.700 | 0.0034 | $1.7 \times 10^{-6}$ |
| rs17696736 | 12 | 110971201 | C12orf30 | G/A | 0.019 | 1.16 | 0.437 | 0.474 | 0.01186 | $2.7 \times 10^{-4}$ |
| rs3184504 | 12 | 110368991 | SH2B3 | T/C | 0.19 | 1.09 | 0.487 | 0.508 | 0.042 | $4.0 \times 10^{-6}$ |
| rs2812378 | 9 | 34700260 | CCL21 | G/A | 0.061 | 1.14 | 0.333 | 0.354 | 0.19 | $1.8 \times 10^{-4}$ |
| rs3761847 | 9 | 122730060 | TRAF1 | G/A | 0.12 | 1.08 | 0.456 | 0.475 | 0.053 | 0.0041 |
| rs6899540 | 6 | 43866302 | VEGFA | C/A | 0.68 | 1.04 | 0.176 | 0.180 | 0.73 | 0.0051 |
| rs547154 | 6 | 32018917 | C2 | T/G | 0.0012 | 0.65 | 0.085 | 0.057 | 0.011 | 0.011 |
| rs12044852 | 1 | 116889302 | CD58 | C/A | 0.33 | 1.10 | 0.872 | 0.883 | 0.13 | 0.026 |
| rs2542151 | 18 | 12769947 | PTPN2 | G/T | 0.077 | 1.16 | 0.154 | 0.178 | 0.077 | 0.037 |
| rs6897932 | 5 | 35910332 | IL7R | C/T | 0.23 | 1.06 | 0.712 | 0.725 | 0.10 | 0.038 |
| rs2230199 | 19 | 6669387 | C3 | C/G | 0.081 | 0.85 | 0.205 | 0.179 | 0.081 | 0.081 |
| rs3732378 | 3 | 39282166 | CX3CR1 | G/A | 0.24 | 0.90 | 0.844 | 0.829 | 0.42 | 0.093 |
| rs1678542 | 12 | 56254982 | KIF5A | C/G | 0.58 | 1.04 | 0.581 | 0.589 | 0.80 | 0.095 |
| rs1136287 | 17 | 1620026 | SERPINF1 | T/C | 0.16 | 1.05 | 0.637 | 0.648 | 0.059 | 0.12 |
| rs12247631 | 10 | 52485603 | PRK81 | A/C | 0.27 | n.a. | 0.000 | 0.001 | 0.25 | 0.14 |
| rs2227306 | 4 | 74825919 | IL8 | T/C | 0.57 | 1.04 | 0.461 | 0.463 | 0.75 | 0.16 |
| rs12521868 | 5 | 131812292 | LOC441108 | T/G | 0.65 | 1.03 | 0.418 | 0.415 | 0.90 | 0.16 |
| rs10490924 | 10 | 124204438 | ARMS2 | G/T | 0.58 | 0.96 | 0.768 | 0.760 | 0.89 | 0.21 |
| rs1793004 | 11 | 20655505 | NELL1 | G/C | 0.24 | 1.09 | 0.725 | 0.746 | 0.10 | 0.22 |
| rs10225965 | 7 | 92111514 | CDK6 | C/T | 0.69 | 0.97 | 0.797 | 0.787 | 0.52 | 0.22 |
| rs1410996 | 1 | 194963556 | CFH | A/G | 0.57 | 1.04 | 0.408 | 0.411 | 0.81 | 0.23 |
| rs3087243 | 2 | 204447164 | CTLA4 | G/A | 0.43 | 1.08 | 0.614 | 0.630 | 0.59 | 0.25 |
| rs2292239 | 12 | 54768447 | ERBB3 | T/G | 0.96 | 1.00 | 0.330 | 0.324 | 0.19 | 0.27 |
| rs12722489 | 10 | 6142018 | IL2RA | C/T | 0.042 | 1.19 | 0.808 | 0.835 | 0.042 | 0.31 |
| rs9332739 | 6 | 32011783 | C2 | C/G | 0.037 | 1.36 | 0.044 | 0.059 | 0.037 | 0.31 |
| rs2076756 | 16 | 49314382 | NOD2 | G/A | 0.78 | 1.01 | 0.200 | 0.203 | 0.64 | 0.37 |
| rs16853571 | 4 | 41447887 | PHOX2B | C/A | 0.33 | 1.20 | 0.056 | 0.067 | 0.73 | 0.47 |
| rs4810485 | 20 | 44181354 | CD40 | T/G | 0.85 | 0.99 | 0.246 | 0.249 | 0.85 | 0.47 |
| rs9340799 | 6 | 152205074 | ESR1 | A/G | 0.60 | 1.04 | 0.680 | 0.694 | 0.57 | 0.49 |
| rs3793784 | 10 | 50417545 | ERCC6 | C/G | 0.23 | 1.08 | 0.385 | 0.395 | 0.96 | 0.61 |
| rs2240340 | 1 | 17535226 | PADI4 | C/T | 0.91 | 0.99 | 0.594 | 0.585 | 0.19 | 0.64 |
| rs7517847 | 1 | 67454257 | IL23R | T/G | 0.33 | 0.98 | 0.531 | 0.525 | 0.48 | 0.80 |

TABLE 7-continued

Confirmed autoimmune disease loci.

Variants in LD with above loci

| rs1061170 | 1 | 194925860 | CFH | T/C | 0.339 | 0.914 | 0.404 | 0.382 | 0.339 | 0.339 |
| rs2234693 | 6 | 152205028 | ESR1 | T/C | 0.719 | 0.993 | 0.556 | 0.555 | 0.375 | 0.375 |
| rs1136287 | 17 | 1620026 | SERPINF1 | T/C | 0.159 | 1.051 | 0.636 | 0.648 | 0.059 | 0.118 |
| rs3024997 | 6 | 43853085 | VEGFA | A/G | 0.662 | 1.006 | 0.293 | 0.294 | 0.847 | 0.847 |
| rs3212227 | 5 | 158675528 | IL12B | T/G | 0.636 | 1.042 | 0.810 | 0.817 | 0.342 | $4 \times 10^{-4}$ |
| rs2339898 | 10 | 53379358 | PRKG1 | C/T | 0.789 | 1.010 | 0.315 | 0.309 | 0.366 | 0.341 |
| rs42041 | 7 | 92084680 | CDK6 | G/C | 0.049 | 0.913 | 0.268 | 0.239 | 0.170 | 0.661 |

Position (basepairs) is reported in HG18 coordinates. P values calculated from indicated case/control population (GWAS: 1310 case and 7859 control, US: 1129 case and 2991 control, Sweden 834 case and 1338 control, Combined: 3273 case and 12,188 control samples), and Combined P value calculated as described in the Methods above, The Replication P value refers to the meta P values for the combined U.S. and Swedish samples. Alleles are reported relative to + reference strand, and all data refers to Allele 1 (A1). The odds ratio (OR) for each population is listed.

Example 2

Re-Sequencing and Identification of the Causal Allele for BLK

As discussed above, BLK has been identified as a risk locus associated with SLE that achieves genome-wide significance ($P<5\times10^{-8}$). To further characterize the genetic basis of this association and to identify causal allele(s) we carried out re-sequencing studies of the BLK locus and reporter gene expression assays as described below.

For the re-sequencing study, all 13 exons and 2.5 kb of upstream promoter sequence of the BLK locus in DNA isolated from 192 patients in the Autoimmune Biomarkers Collaborative Network (ABCoN) (Bauer et al., PLoS medicine 3(12):e491 (2006)), an NIH/NIAMS-funded repository, and 96 control individuals in New York Cancer Project (NYCP) (Mitchell et al., J. Urban Health 81:301-10 (2004)) was re-sequenced. Genomic DNA was whole-genome amplified according to the manufacturer's protocol (Qiagen, Valencia, Calif., Cat. No. 150045) prior to sequencing.

The re-sequencing results showed that 17 mutations (10 non-synonymous, 7 synonymous) were found in the coding region of the BLK gene (Table 8). None of these mutations showed significantly higher frequencies in cases than in the controls. The overall frequency of non-synonymous mutation was not significantly higher in cases ($14/191$) than in controls ($7/96$).

Figure 4:
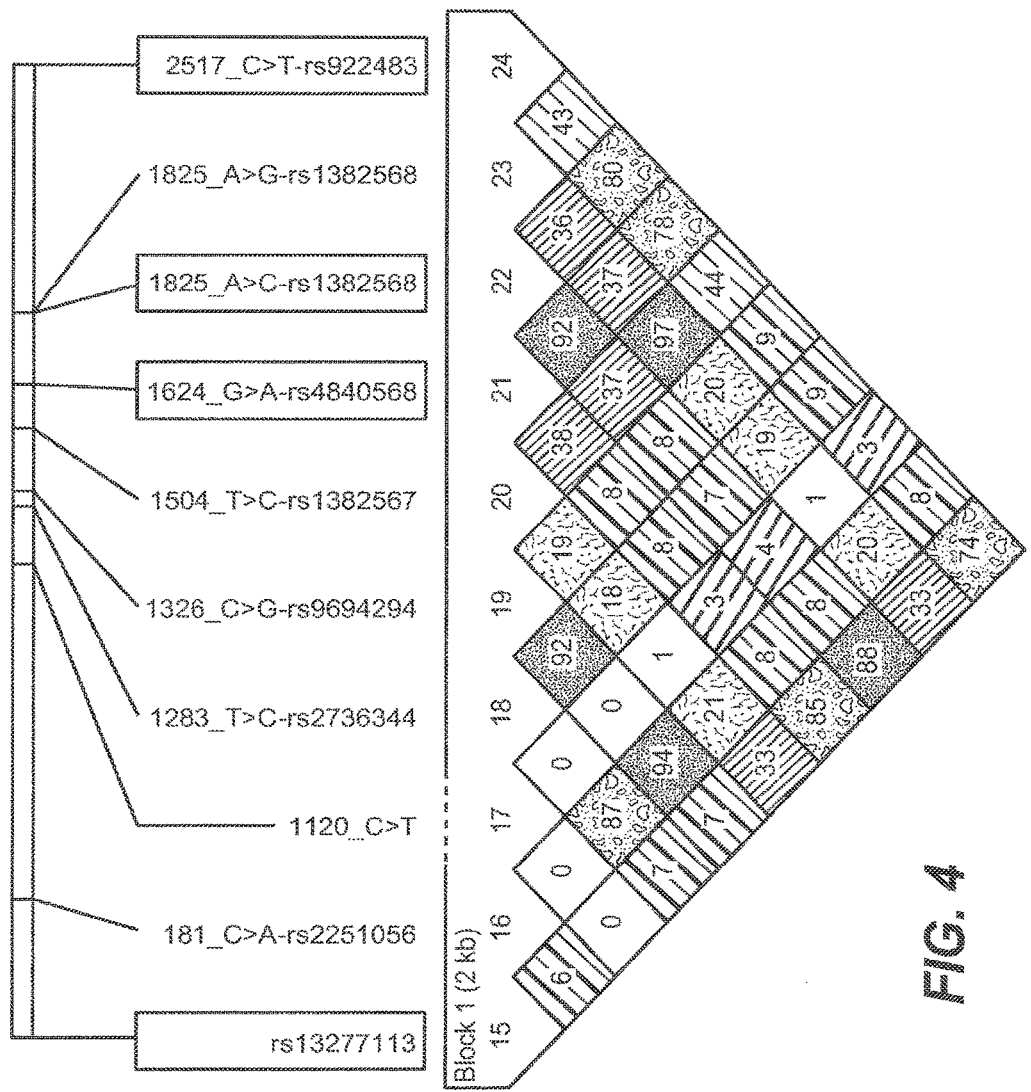
FIG. 4 shows a linkage disequilibrium block (shown in $r^2$) within the BLK promoter region as described in Example 2.

In addition, multiple common variations were identified in the non-coding region of BLK (shown in Table 9). Three SNPs (rs4840568, rs1382568 [a tri-allelic SNP (A/C/G); C allele was previously identified as the risk allele], and rs922483 (SEQ ID NO: 13)) showed association with the loci previously identified from GWAS (Horn et al., N Engl J Med 358:900-09 (2008)) (rs13277113, odds ratio, 1.39, $P=1\times10^{-10}$ with $r^2>0.5$. FIG. 4 shows a Linkage Disequilibrium (LD) block (shown in $r^2$) within the promoter region of that was generated using Haploview (software freely available at the URL www(dot)broadinstitute(dot)org(slash) haploview(slash)haploview; see Barrett J. C., et al., Bioinformatics 21:263-65 (2005). The top portion of the figure shows a schematic diagram of the promoter region of BLK with the relative location of the identified SNPs indicated. The $r^2$ value between the listed SNPs is shown in the boxes. The strength of LD between two SNPs is indicated by the $r^2$ value provided in each box. The loci identified from GWAS (rs13277113) and the three SNPs identified from re-sequencing (rs4840568, rs1382568, and rs922483 (SEQ ID NO: 13)) are indicated in black border at the top of the figure.

This re-sequencing study did not reveal any common variation in the coding region of BLK. Three common variants (rs4840568, rs1382568, and rs922483 (SEQ ID NO: 13)) at the promoter region, however, were identified as potential causal allele(s) of the biological effects of BLK associated with increased risk of SLE. Each of these variations was employed in luciferase reporter assays described in detail below to further characterize the association.

TABLE 8

Mutations in the BLK coding region

| Exon | Amino Acid Change (Protein: NP_001706.2) | Nucleotide Change (mRNA: NM_001715.2) | dbSNP | dbSNP | Zygosity | Non-synonymous | Cases (n = 191) | Controls (n = 96) |
| --- | --- | --- | --- | --- | --- | --- | --- | --- |
| 2 | 39P > L | 697_C > T | N/A | N/A | Heterozygous | Yes | 1 | 0 |
| 4 | 71A > T | 792_G > A | rs55758736 | N/A | Heterozygous | Yes | 6 | 4 |
| 4 | 75R > R | 806_G > T | N/A | N/A | Heterozygous | No | 1 | 0 |
| 4 | 86Q > Q | 839_G > A | rs56185487 | N/A | Heterozygous | No | 2 | 0 |
| 6 | 131R > W | 972_C > T | N/A | N/A | Heterozygous | Yes | 2 | 0 |
| 6 | 137Q > Q | 992_G > A | N/A | N/A | Heterozygous | No | 0 | 1 |
| 7 | 180R > H | 1120_G > A | N/A | N/A | Heterozygous | Yes | 1 | 0 |
| 7 | 190S > S | 1151_C > T | N/A | N/A | Homozygous | No | 0 | 1 |
| 8 | 237P > P | 1292_C > T | N/A | N/A | Heterozygous | No | 1 | 1 |
| 8 | 238R > Q | 1294_G > A | N/A | N/A | Heterozygous | Yes | 1 | 0 |
| 10 | 325K > T | 1555_A > C | N/A | N/A | Heterozygous | Yes | 2 | 0 |
| 10 | 327D > V | 1561_A > T | N/A | N/A | Heterozygous | Yes | 0 | 1 |

TABLE 8-continued

Mutations in the BLK coding region

| Exon | Amino Acid Change (Protein: NP_001706.2) | Nucleotide Change (mRNA: NM_001715.2) | dbSNP | dbSNP | Zygosity | Non-synonymous | Cases (n = 191) | Controls (n = 96) |
|---|---|---|---|---|---|---|---|---|
| 10 | 331R > I | 1573_G > T | N/A | N/A | Heterozygous | Yes | 1 | 0 |
| 11 | 359R > C | 1656_C > T | N/A | N/A | Heterozygous | Yes | 0 | 1 |
| 12 | 425L > P | 1855_T > C | N/A | N/A | Heterozygous | Yes | 0 | 1 |
| 13 | 464L > L | 1973_G > A | N/A | N/A | Heterozygous | No | 1 | 0 |
| 13 | 474R > R | 2003_C > T | N/A | N/A | Heterozygous | No | 2 | 0 |
|  |  |  |  |  |  | Non-synonymous mutation frequency | 14/191 | 7/96 |

TABLE 9

Common variations in the BLK non-coding region ('rs922483' disclosed as SEQ ID NO: 13).

| Nucleotide Change | Chromosomal location | Chromosome | dbSNP | Assoc. Allele | Case, Control Ratio Counts (191, 96) | Case, Control Frequencies | Chi square | P value | r^2 (with rs13277113) |
|---|---|---|---|---|---|---|---|---|---|
| C > A | 11386986 | 8 | rs2251056 | A | 321:61, 150:42 | 0.840, 0.781 | 3.027 | 0.0819 | 0.066 |
| C > T | 11387925 | 8 | N/A | T | 8:374, 1:191 | 0.021, 0.005 | 2.05 | 0.1522 | 0.006 |
| T > C | 11388088 | 8 | rs2736344 | C | 329:53, 149:43 | 0.861, 0.776 | 6.662 | 0.0098 | 0.072 |
| C > G | 11388131 | 8 | rs9694294 | G | 323:59, 149:43 | 0.846, 0.776 | 4.225 | 0.0398 | 0.078 |
| T > C | 11388309 | 8 | rs1382567 | T | 199:183, 93:99 | 0.521, 0.484 | 0.684 | 0.4083 | 0.335 |
| G > A | 11388429 | 8 | rs4840568 | A | 125:257, 41:151 | 0.327, 0.214 | 8.033 | 0.0046 | 0.852 |
| A > C | 11388630 | 8 | rs1382568 | C | 121:261, 38:154 | 0.317, 0.198 | 9.01 | 0.0027 | 0.889 |
| A > G | 11388631 | 8 | rs1382568 | A | 200:182, 94:98 | 0.524, 0.490 | 0.59 | 0.4423 | 0.331 |
| C > T | 11389322 | 8 | rs922483 | T | 137:245, 43:149 | 0.359, 0.224 | 10.768 | 0.001 | 0.741 |
| A > G | 11389466 | 8 | N/A | G | 320:62, 148:44 | 0.838, 0.771 | 3.794 | 0.0514 | 0.059 |
| C > T | 11404079 | 8 | N/A | C | 274:108, 128:64 | 0.717, 0.667 | 1.56 | 0.2117 | 0.037 |
| G > C | 11404447 | 8 | N/A | G | 358:24, 176:16 | 0.937, 0.917 | 0.829 | 0.3626 | 0.018 |
| C > T | 11404452 | 8 | N/A | T | 55:327, 23:169 | 0.144, 0.120 | 0.637 | 0.4249 | 0.038 |
| T > C | 11404627 | 8 | N/A | C | 91:291, 45:147 | 0.238, 0.234 | 0.01 | 0.9186 | 0.001 |
| T > C | 11443842 | 8 | N/A | T | 196:184, 80:112 | 0.516, 0.411 | 5.019 | 0.0251 | 0.083 |
| T > C | 11451476 | 8 | N/A | C | 315:65, 150:38 | 0.829, 0.798 | 0.818 | 0.3657 | 0.016 |
| A > G | 11452981 | 8 | rs4841557 | A | 158:222, 63:129 | 0.416, 0.328 | 4.135 | 0.042 | 0.187 |
| C > T | 11453006 | 8 | rs4841558 | C | 157:223, 63:129 | 0.413, 0.328 | 3.897 | 0.0484 | 0.181 |
| G > A | 11455795 | 8 | rs1042695 | A | 145:237, 59:133 | 0.380, 0.307 | 2.915 | 0.0878 | 0.179 |
| G > A | 11456175 | 8 | N/A | A | 335:45, 157:35 | 0.882, 0.818 | 4.325 | 0.0375 | 0.019 |
| G > A | 11456176 | 8 | N/A | G | 340:42, 157:35 | 0.890, 0.818 | 5.758 | 0.0164 | 0.015 |
| C > T | 11456182 | 8 | rs4841561 | T | 146:234, 59:133 | 0.384, 0.307 | 3.282 | 0.07 | 0.177 |
| C > T | 11458793 | 8 | rs10097015 | T | 160:222, 68:122 | 0.419, 0.358 | 1.967 | 0.1608 | 0.161 |
| C > T | 11459203 | 8 | rs1042689 | T | 144:238, 62:130 | 0.377, 0.323 | 1.622 | 0.2028 | 0.161 |
| G > A | 11459455 | 8 | N/A | G | 213:169, 98:94 | 0.558, 0.510 | 1.145 | 0.2845 | 0.2 |
| T > C | 11459540 | 8 | N/A | T | 212:170, 100:92 | 0.555, 0.521 | 0.6 | 0.4385 | 0.219 |

Luciferase reporter gene assays were performed to investigate the effect of the three SNPs, rs4840568, rs1382568, and rs922483 (SEQ ID NO: 13) on BLK-mediated gene expression. An upstream sequence (−2256 to +55 bp) of BLK was amplified using genomic DNA from individuals that carry risk or non-risk haplotype. Each PCR product was cloned into pCR2.1-TOPO vector (Invitrogen, Carlsbad, Calif.; Cat. No. K4500-01) and then sub-cloned into pGL4 luciferase reporter vector (Promega, Madison, Wis.; Cat. No. E6651). A construct that carries non-risk haplotype was used as template for mutagenesis (Stratagene, La Jolla, Calif.; Cat. No. 10519-5) to create various haplotypes.

The primers used in PCR amplification were as follows: forward: CCACCTCTCTICCGCCTITCTCAT (SEQ ID NO.: 1); reverse: TTTCATGGCTTGIGGCTTTCTGCC (SEQ ID NO.: 2). The primers used in mutagenesis are listed in Table 10 below.

TABLE 10

List of mutagenesis primers.

| Primer | Sequence |
|---|---|
| rs4840568_G > A forward | GATCCAAGACTATGA AGAGAGAAGAGAGAG CCCAC (SEQ ID NO.: 3) |
| rs4840568_G > A reverse | GTGGGCTCTCTCTTC TCTCTTCATAGTCTT GGATC (SEQ ID NO.: 4) |
| rs1382568_A > C forward | CCAGACACCACTCAC CCCTCTAGATGTTGG GAT (SEQ ID NO.: 5) |

TABLE 10-continued

List of mutagenesis primers.

| Primer | Sequence |
| --- | --- |
| rs1382568_A > C reverse | ATCCCAACATCTAGA GGGGTGAGTGGTGTC TGG (SEQ ID NO.: 6) |
| rs1382568_A > G forward | CCAGACACCACTCAC CGCTCTAGATGTTGG GAT (SEQ ID NO.: 7) |
| rs1382568_A > G reverse | ATCCCAACATCTAGA GCGGTGAGTGGTGTC TGG (SEQ ID NO.: 8) |
| rs1382568_G > A forward | CCAGACACCACTCAC CACTCTAGATGTTGG GAT (SEQ ID NO.: 9) |
| rs1382568_G > A reverse | ATCCCAACATCTAGA GTGGTGAGTGGTGTC TGG (SEQ ID NO.: 10) |
| rs922483_C > T (SEQ ID NO: 13) forward | CGGGGGTGCTGCTACC TCTGTCTGC (SEQ ID NO.: 11) |
| rs922483_C > T (SEQ ID NO: 13) reverse | GCAGACAGAGGTAGCA GCACCCCCG (SEQ ID NO.: 12) |

Renilla luciferase control reporter vector pRL-TK (Promega, Madison, Wis.; Cat. No. E2241) was used for normalization. The cell line BJAB (a continuous lymphoid cell line with characteristics of B cells (bone marrow-derived), lacking the Epstein-Barr virus genome and derived from three human lymphomas; Klein et al., Proc. Natl. Acad. Sci. USA 71:3283-86 (1974)) or the Daudi cell line (American Type Culture Collection (ATCC) cat. No. CCL-213) was used for transfections. For each transfection, $5 \times 10^6$ cells were transfected with 5 µg of DNA of each vector using an Amaxa® Nucleofector® device (Lonza, Walkersville Inc., Walkersville, Md. (Lonza Group Ltd., Switzerland); Cat. No. AAD-1001). Cell line Nucleofector® Kit L (Lonza, Cat. No. VCA-1005) was used for Daudi cells with Nucleofector® device Program A-030. Cell line Nucleofector® Kit V (Lonza, Cat. No. VCA-1005) was used for BJAB cells with Nucleofector® device Program T-020. All transfections were carried out either in duplicate or triplicate. Cells were incubated at 37° C. for 16 hours following transfection. Following that incubation, cells were harvested and luciferase activity was measured using the Dual-Luciferase® Reporter Assay System (Promega, Madison, Wis.; Cat. No. E1960) according to the manufacturer's instructions.

The effects of each of the SNPs rs4840568, rs1382568, and rs922483 (SEQ ID NO: 13) on BLK-mediated gene expression as measured in the luciferase reporter assay system described above are shown in FIG. 5. The different haplotypes generated by mutagenesis were compared with non-risk (wild-type) haplotype 22-GAC (open bar in each of FIGS. 5A-F) and risk haplotype 22-ACT (hatched bar in each of FIGS. 5A-F).

Figure 5A:
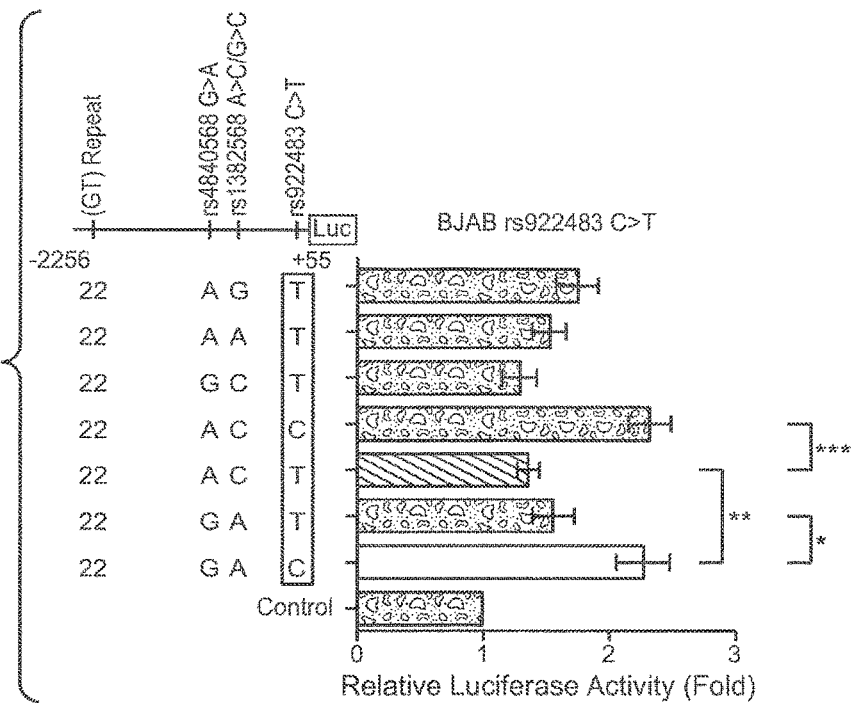
FIGS. 5A-5F show the results of luciferase reporter gene expression assays of the BLK promoter region having various haplotypes as described in Example 2.
Figure 5B:
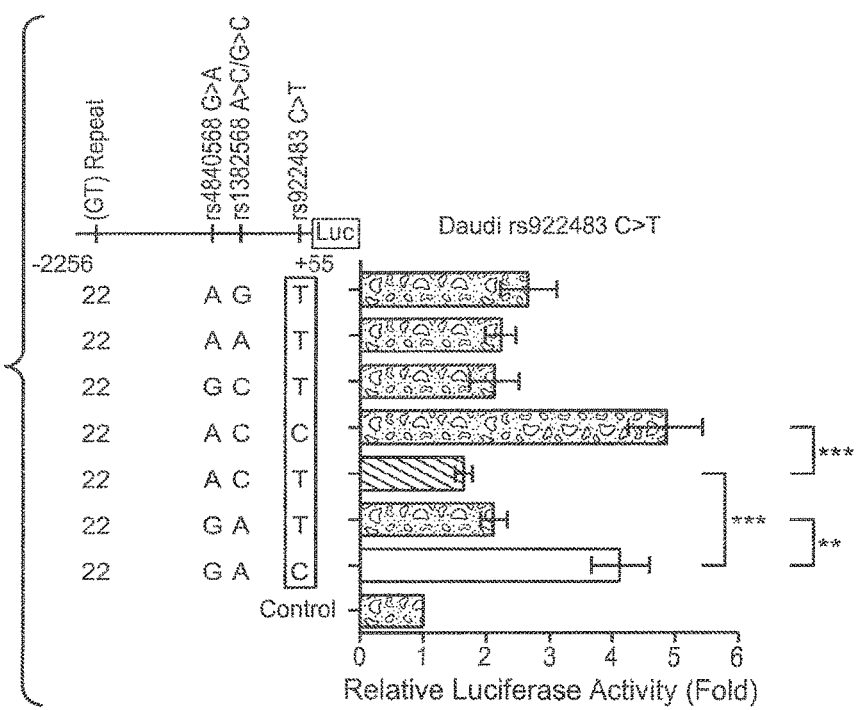

FIGS. 5A and 5B show that SNP rs922483 (C>T) (SEQ ID NO: 13) led to a significant effect on BLK-mediated gene expression in both BJAB (FIG. 5A) and Daudi cells (FIG. 5B). Compared to non-risk haplotype 22-GAC (open bar), haplotype 22-GAT showed reduced transcriptional activity by almost 50% in both cell lines. Haplotypes with T allele showed consistently lower activity than those with C alleles. Five independent experiments were done in BJAB cells and six independent experiments were done in Daudi cells. Data shown represent the mean+/-standard error of the mean (s.e.m.) in triplicate assays; *$p<0.05$, $p<0.01$, *$p<0.001$ (t-test).

Figure 5C:
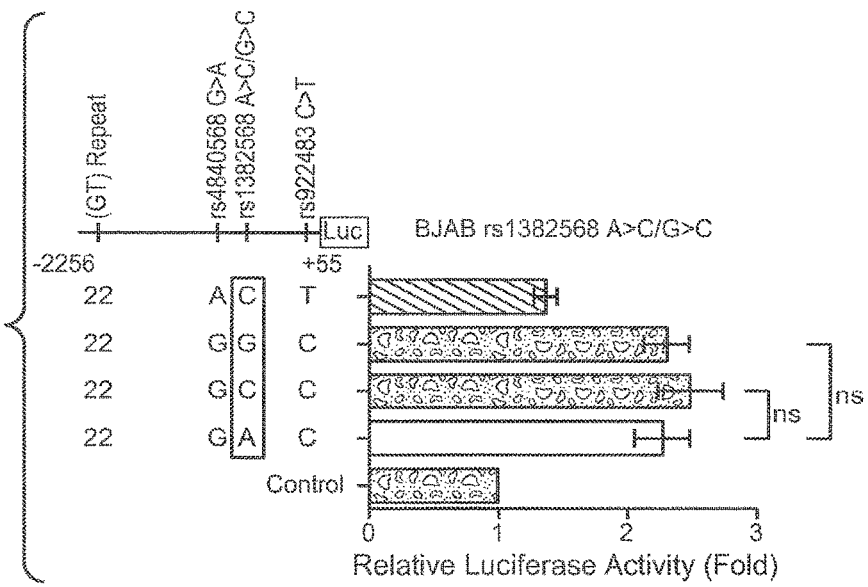
Figure 5D:
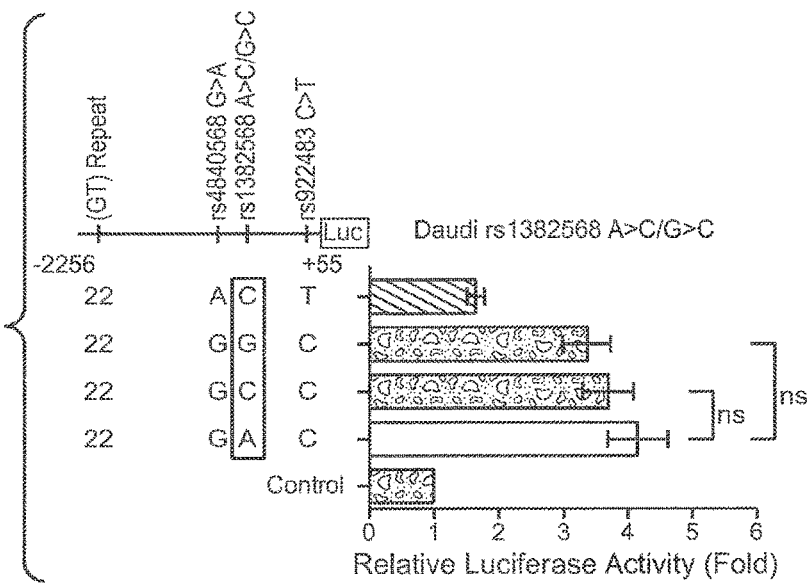

FIGS. 5C and 5D show that SNP rs1382568 (A>C/G>C) did not result in any significant effect on BLK-mediated expression in either cell line. Both haplotypes 22-GCC and 22-GGC (spotted bars) showed a similar level of luciferase activity compared to non-risk haplotype 22-GAC (open bar). Five independent experiments were done in BJAB cells and six independent experiments were done in Daudi cells. Data shown represent the mean+/-s.e.m. in triplicate assays; *$p<0.05$, $p<0.01$, *$p<0.001$, ns=not significant (t-test).

Figure 5E:
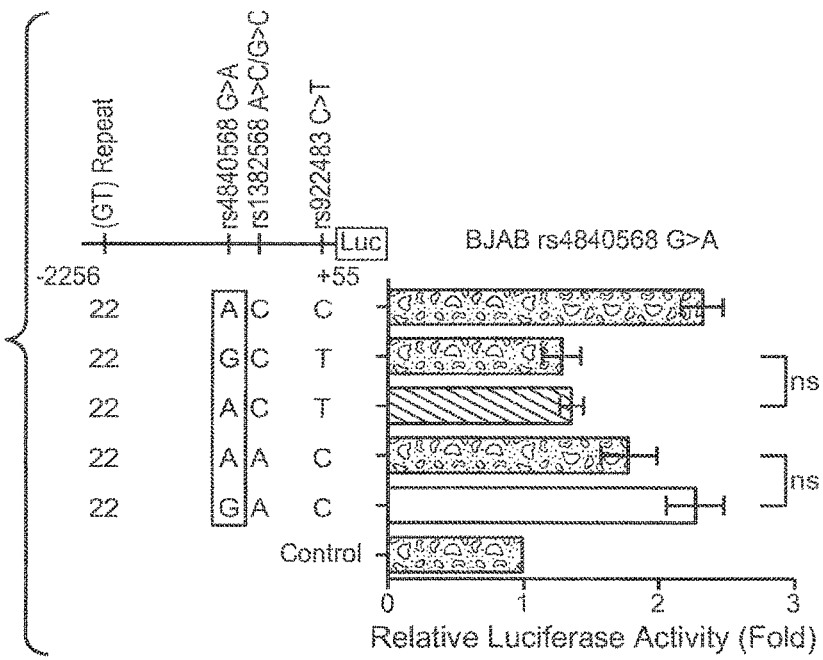
Figure 5F:
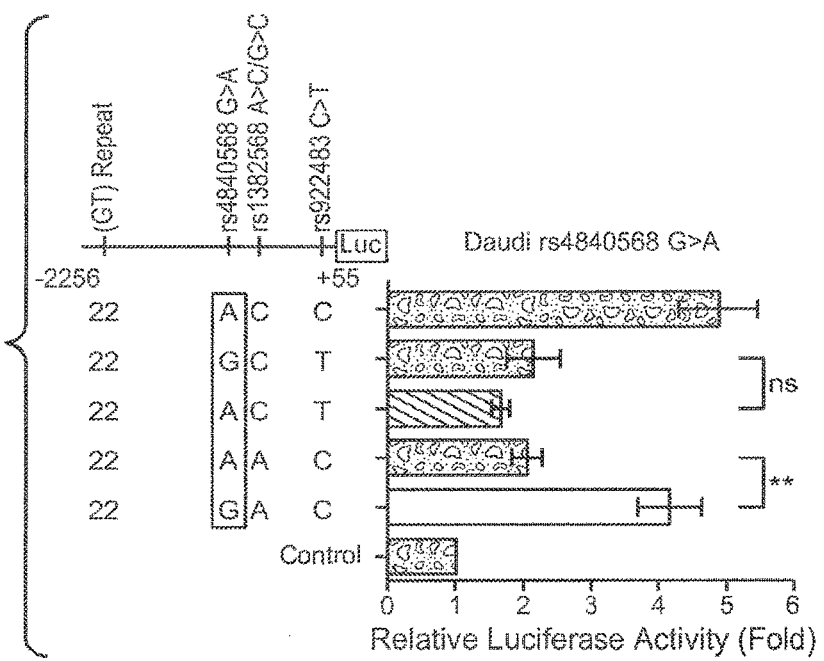

FIGS. 5E and 5F show that SNP rs4840568 (G>A) did not result in a significant effect on BLK-mediated expression in BJAB cells or Daudi cells. The difference between haplotype 22-AAC (spotted bar) and non-risk haplotype 22-GAC (open bar) was not statistically significant in BJAB cells (FIG. 5E), but it was statistically significant in Daudi cells (FIG. 5F). The likelihood of A allele being a causal allele is greatly reduced given the fact that haplotype 22-ACC (spotted bar) did not show any defect in luciferase activity compared to the non-risk haplotype-GAC (open bar) (FIG. 5F). Data shown represent the mean+/-s.e.m. in triplicate assays; *$p<0.05$, $p<0.01$, *$p<0.001$, ns=not significant (t-test).

Figures 6, 7:
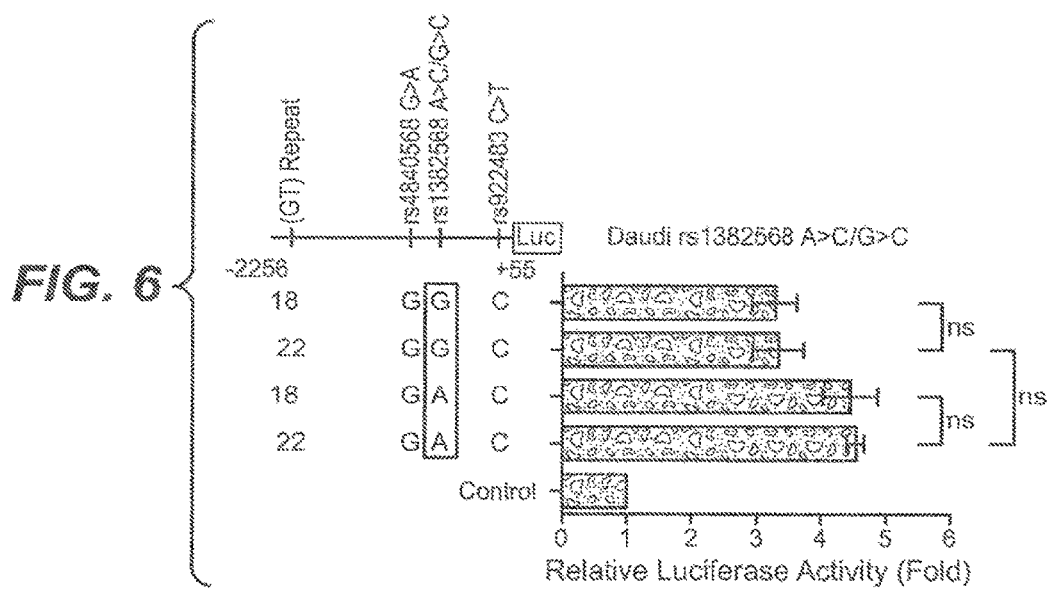
FIG. 6 shows the results of luciferase reporter gene expression assays of the BLK promoter region having either 18 (GT) repeats (SEQ ID NO: 14) or 22 (GT) repeats (SEQ ID NO: 15) and the SNP rs1382568 A>C/G>C in Daudi cells as described in Example 2. Data shown represent the mean+/−standard error of the mean in duplicate assays; ns=not significant (t-test).
FIG. 7 shows the sequence of the SNP, rs922483 (SEQ ID NO: 13), and the location within the SNP of the causal allele for the BLK locus as described in Example 2. The location of the causal allele is shown by bold brackets; the CIT variations are indicated in bold.

It was shown previously that the (GT) repeat in the region upstream of the BLK promoter can function as an enhancer of BLK gene expression (Lin et al., J Biol Chem 270: 25968 (1995)). Therefore, we also tested whether the length of (GT) repeat can affect the transcriptional activity of the BLK promoter. To perform these experiments, genomic DNA samples from individuals that carry both 18 (GT) repeats (SEQ ID NO: 14) or 22 (GT) repeats (SEQ ID NO; 15) were selected for cloning using the strategy described above. Final vectors were sequenced to confirm they contained the correct length of (GT) repeats. As shown in FIG. 6, haplotypes with 18 (GT) repeats (SEQ ID NO: 14) displayed a similar level of transcriptional activity compared to those with 22 (GT) repeats (SEQ ID NO: 15) in the luciferase reporter assay. Data shown represent the mean+1-s.e.m in duplicate assays, ns=not significant (t-test).

In summary, these results of the BLK re-sequencing efforts and the results of the luciferase reporter gene assays indicate that SNP rs922483 (C>T) (FIG. 7, SEQ ID NO: 13) is the causal allele that results in decreased transcription of BLK, a biological effect which is associated with an increased risk of SLE. In addition, the results showed that the T allele of rs922483 (SEQ ID NO: 13) reduced the level of BLK-mediated gene expression by 50%.

It is interesting to note that rs922483 (SEQ ID NO: 13) resides in an evolutionarily conserved region in the first exon of BLK and within a possible human transcription initiation site. A consensus sequence for the human Inr motif has been identified as YYANWYY (IUPAC nucleotide code). Juven-Gershon et al. Dev. Biol. 339:225-229 (2010). In the SNP rs922483 (SEQ ID NO: 13), the second base in the Inr region is altered relative to the consensus motif. Accordingly, the SLE risk haplotype Inr sequence is CTACCTC while the "wild type" haplotype Inr sequence is CCACCTC. We suggest that the modification of the second base in the conserved Inr motif might alter the affinity of the TFIID transcription complex resulting in the observed difference in transcription described above.

What is claimed is:

1. A method of treating a human subject having systemic lupus erythematosus (SLE), the method comprising:
   (a) obtaining a biological sample from the subject;
   (b) detecting in the biological sample the presence of a variation in a SLE risk locus, wherein the SLE risk locus is juxtaposed with another zinc finger 1 gene (JAZF1), and the variation in the JAZF1 locus is a thymine (T) risk allele of a single nucleotide polymorphism (SNP) of rs849142; and
   (c) administering an effective amount of an interferon inhibitor to the subject to treat SLE when the risk allele is detected.

2. The method of claim 1, comprising detecting a further variation in at least one further SLE risk locus, wherein the further SLE risk locus comprises one or more of the group consisting of tumor necrosis factor-alpha-induced protein 3-interacting protein 1 gene (TNIP1) locus, positive regulatory domain-containing protein 1 gene (PRDM1) locus, ubiquitin-like containing plant homeodomain and ring finger domains 1-binding protein 1 gene (UHRF1BP1) locus, and interleukin-10 gene (IL10) locus.

3. The method of claim 1, comprising detecting a further variation in at least one further SLE risk locus, wherein the further SLE risk locus comprises one or more of the group consisting of interferon-induced helicase C domain-containing protein 1 gene (IFIH1) locus, complement factor B gene (CFB) locus, C-type lectin domain family 16 member A gene (CLEC16A) locus, and interleukin-12 beta chain gene (IL12B) locus.

4. The method of claim 2, comprising detecting a still further variation in at least one still further SLE risk locus, wherein the still further SLE risk locus comprises one or more of the group consisting of interferon-induced helicase C domain-containing protein 1 gene (IFIH1) locus, complement factor B gene (CFB) locus, C-type lectin domain family 16 member A gene (CLEC16A) locus, and interleukin-12 beta chain gene (IL12B) locus.

5. The method of claim 1, comprising detecting a further variation in at least one further SLE risk locus, wherein the further SLE risk locus is B lymphoid tyrosine kinase gene (BLK), and wherein the further variation in the BLK locus is a thymine (T) risk allele of a SNP of rs922483.

6. The method of claim 1, wherein the detecting comprises carrying out a process selected from a primer extension assay; an allele-specific primer extension assay; an allele-specific nucleotide incorporation assay; an allele-specific oligonucleotide hybridization assay; a 5' nuclease assay; an assay employing molecular beacons; and an oligonucleotide ligation assay.

7. The method of claim 1, wherein the interferon inhibitor is anti-interferon-alpha.

8. The method of claim 2, wherein the at least one further SLE risk locus comprises the tumor necrosis factor-alpha-induced protein 3-interacting protein 1 gene (TNIP1) locus and the further variation in the TNIP1 locus is a cytosine (C) allele of a SNP at rs7708932.

9. The method of claim 2, wherein the at least one further SLE risk locus comprises the positive regulatory domain-containing protein 1 gene (PRDM1) locus and the further variation in the PRDM1 locus is an adenine (A) allele of a SNP at rs6568431.

10. The method of claim 2, wherein the at least one further SLE risk locus comprises the ubiquitin-like containing plant homeodomain and ring finger domains 1-binding protein 1 gene (UHRF1BP1) UHRF1BP1 locus and the further variation in the UHRF1BP1 locus is a guanine (G) allele of a SNP at rs11755393.

11. The method of claim 2, wherein the at least one further SLE risk locus comprises the interleukin-10 gene (IL10) locus and the further variation in the IL10 locus is an adenine (A) allele of a SNP at rs3024505.

12. The method of claim 4, wherein the at least one still further SLE risk locus comprises the interferon-induced helicase C domain-containing protein 1 gene (IFIH1) locus and the still further variation in the IFIH1 locus is a thymine (T) allele of a SNP at rs1990760.

13. The method of claim 4, wherein the at least one still further SLE risk locus comprises the complement factor B gene (CFB) locus and the still further variation in the CFB locus is a guanine (G) allele of a SNP at rs641153.

14. The method of claim 4, wherein the at least one still further SLE risk locus comprises the C-type lectin domain family 16 member A gene (CLEC16A) CLEC16A locus and the still further variation in the CLEC16A locus is an adenine (A) allele of a SNP at rs12708716.

15. The method of claim 4, wherein the at least one still further SLE risk locus comprises the interleukin-12 beta chain gene (IL12B) locus and the still further variation in the IL12B locus is a guanine (G) allele of a SNP at rs6887695.

16. A method of treating a human subject having systemic lupus erythematosus (SLE), the method comprising:
    (a) obtaining a biological sample from the subject;
    (b) detecting in the biological sample the presence of at least one risk allele of at least one single nucleotide polymorphism (SNP) comprising a thymine (T) risk allele of a SNP at rs849142; and
    (c) administering an effective amount of an interferon inhibitor to the subject to treat SLE when the at least one risk allele is detected,
    wherein the detecting comprises nucleic acid hybridization.

17. The method of claim 16, wherein the at least one risk allele of the at least one SNP further comprises one or more of the group consisting of:
    a cytosine (C) allele of a SNP at rs7708932,
    an adenine (A) allele of a SNP at rs6568431,
    a guanine (G) allele of a SNP at rs11755393,
    an adenine (A) allele of a SNP at rs3024505,
    a thymine (T) allele of a SNP at rs1990760,
    a guanine (G) allele of a SNP at rs641153,
    an adenine (A) allele of a SNP at rs12708716,
    a guanine (G) allele of a SNP at rs6887695, and
    a thymine (T) risk allele of a SNP of rs922483.

18. The method of claim 16, wherein the at least one risk allele of the at least one SNP further comprises one or more of the group consisting of:
    a cytosine (C) allele of a SNP at rs7708932,
    an adenine (A) allele of a SNP at rs6568431,
    a guanine (G) allele of a SNP at rs11755393, and
    an adenine (A) allele of a SNP at rs3024505.

19. The method of claim 16, wherein the at least one risk allele of the at least one SNP further comprises one or more of the group consisting of:
    a thymine (T) allele of a SNP at rs1990760,
    a guanine (G) allele of a SNP at rs641153,
    an adenine (A) allele of a SNP at rs12708716, and
    a guanine (G) allele of a SNP at rs6887695.

20. The method of claim 16, wherein the at least one risk allele of the at least one SNP further comprises a thymine (T) risk allele of a SNP of rs922483.

21. The method of claim 16, wherein the interferon inhibitor is anti-interferon-alpha.

22. The method of claim 16, wherein the nucleic acid hybridization comprises use of a microarray.

* * * * *